United States Patent [19]
Hohmann et al.

[11] Patent Number: 6,087,152
[45] Date of Patent: Jul. 11, 2000

[54] FERMENTATIVE CAROTENOID PRODUCTION

[75] Inventors: Hans-Peter Hohmann, Freiburg, Germany; Luis Pasamontes, Trimbach, Switzerland; Michel Tessier, Mulhouse, France; Adolphus van Loon, Rheinfelden, Switzerland

[73] Assignee: Roche Vitamins Inc., Parsippany, N.J.

[21] Appl. No.: 08/660,645

[22] Filed: Jun. 7, 1996

[30] Foreign Application Priority Data

Jun. 9, 1995 [EP] European Pat. Off. ............. 95108888

[51] Int. Cl.⁷ ............................. C12N 1/20; C07H 21/04
[52] U.S. Cl. ................................ 435/252.31; 435/252.3; 435/252.33; 435/320.1; 435/183; 435/189; 435/232; 435/233; 536/23.1; 536/23.2; 536/23.7
[58] Field of Search .................................. 435/183, 252.3, 435/252.33, 320.1, 252.31, 189, 232, 233; 536/23.1, 23.2, 23.7

[56] References Cited

U.S. PATENT DOCUMENTS

| | | | |
|---|---|---|---|
| 3,891,504 | 6/1975 | Schocheer et al. | 195/28 R |
| 5,304,478 | 4/1994 | Bird et al. | 435/320.1 |

FOREIGN PATENT DOCUMENTS

| | | |
|---|---|---|
| 393690 | 10/1990 | European Pat. Off. . |
| 91/03571 | 3/1991 | WIPO . |
| 91/13078 | 9/1991 | WIPO . |

OTHER PUBLICATIONS

Pasamontes et al. "Isolation and characterization of the cartenoid biosynthesis genes of Flavobacterium sp. strain 1534" Gene 185, 35–41, 1997.

Misawa et al. "Structure and function analysis of a marine bacterial cartenoid biosynthesis gene cluster and astaxanthin biosynthetic pathway propsed at the gene level" J. Bacteriol. 177(22), 6575–6584, Nov. 1995.

Armstrong et al., Mol. Gen. Genet. 216:254–268 (1989).
Misawa et al., J. Bacteriol. 172:6704–6712 (1990).
Armstrong et al., PNAS 87:9975–9979 (1990).
Carattoli et al., J. Biol. Chem. 266:5854–5859 (1991).
Schmidhauser et al., J. Biol. Chem. 269:12060–12066 (1994).
Schmidhauser et al., Mol. Cell. Biol. 10:5064–5070 (1990).
Hoshino et al., Appl. Environ. Microbiol. 59:3150–3153 (1993).
Chamovitz et al., Plant Mol. Biol. 16:967–974 (1991).
Cunningham et al., Plant Cell 6:1107–1121 (1994).
Martinez–Ferez et al., Biochim. Biophys. Acta 1218:145–152 (1994).
Martinez–Ferez et al., Plant Mol. Biol. 18:981–983 (1992).
Bartley et al., J. Biol. Chem. 268:25718–25721 (1993).
Bartley et al., PNAS 88:6532–6536 (1991).
Schmidt A., Gene 91:113–117 (1990).
Fontes et al., EMBO J. 12:1265–1275 (1993).
Romer et al., Biochem. Biophys. Res. Commun. 196:1414–1421 (1993).
Bouvier et al., Plant J., 6:45–54 (1994).
Misawa et al., Biochem. and Biophys. Research Comm., vol. 209, No. 3, 867–876 (1995).
Derwent Abstract No. AN 94–230229.

*Primary Examiner*—Robert A. Wax
*Assistant Examiner*—Nashaat T. Nashed
*Attorney, Agent, or Firm*—George W. Johnston; Dennis P. Tramaloni; Eileen M. Ebel

[57] ABSTRACT

Novel proteins of Flavobacterium sp. R1534 and the DNA sequences which encode these proteins are disclosed which provide an improved biosynthetic pathway from farnesyl pyrophosphate and isopentyl pyrophosphate to various carotenoid precursors and carotenoids, especially β-carotene, lycopene, zeaxanthin and cantaxanthin.

73 Claims, 92 Drawing Sheets

FIG. 7A

```
     GGATCCGCGCCTGGCCGTTCGCGATCAGCAGCCGCCCTTGCGGATCGGTC
  1  --------------------------------------------------  50
     CCTAGGCGCGGACCGGCAAGCGCTAGTCGTCGGCGGGAACGCCTAGCCAG orf-5→D   P   R   L   A   V   R   D   Q   Q   P   P   L   R   I   G   Q AGCATCATCCCCATGAACCGCAGCGCACGACGCAGCGCGCGCCCCAGATC
 51  --------------------------------------------------  100
     TCGTAGTAGGGGTACTTGGCGTCGCGTGCTGCGTCGCGCGCGGGGTCTAG

H   H   P   H   E   P   Q   R   T   T   Q   R   A   P   Q   I

GGGCGCGTCCAGCACGGCATGCGCCATCATCGCGAAGGCCCCCGGCGGCA
101  --------------------------------------------------  150
     CCCGCGCAGGTCGTGCCGTACGCGGTAGTAGCGCTTCCGGGGCCGCCGT

G   R   V   Q   H   G   M   R   H   H   R   E   G   P   R   R   H

TGGGGCGCGTGCCCATTCCGAAGAACTCGCAGCCTGTCCGCTGCGCAAGG
151  --------------------------------------------------  200
     ACCCCGCGCACGGGTAAGGCTTCTTGAGCGTCGGACAGGCGACGCGTTCC

G   A   R   A   H   S   E   E   L   A   A   C   P   L   R   K   V

TCGCGCCAGATCGCGCCGTATTCCGATGCAGTGACGGGCCCGATGCGCGT
201  --------------------------------------------------  250
     AGCGCGGTCTAGCGCGGCATAAGGCTACGTCACTGCCCGGGCTACGCGCA

A   P   D   R   A   V   F   R   C   S   D   G   P   D   A   R

GGGCCCGCCCTGCCCCGCCGCCACCAGCGCATCGCGCACGAACCCTTCCG
251  --------------------------------------------------  300
     CCCGGGCGGGACGGGGCGGCGGTGGTCGCGTAGCGCGTGCTTGGGAAGGC

G   P   A   L   P   R   R   H   Q   R   I   A   H   E   P   F   R
```

```
         AGATGATGTGCTGATCCATGGCCCGTCATTGCAAAACCGATCACCGATCC
301      --------------------------------------------------      350
         TCTACTACACGACTAGGTACCGGGCAGTAACGTTTTGGCTAGTGGCTAGG

D   D   V   L   I   H   G   P   S   L   Q   N   R   S   P   I   L

TGTCGCGTGATGGCATTGTTTGCAATGCCCCGAGGGCTAGGATGGCGCGA
351      --------------------------------------------------      400
         ACAGCGCACTACCGTAACAAACGTTACGGGGCTCCCGATCCTACCGCGCT

S   R   D   G   I   V   C   N   A   P   R   A   R   M   A   R

AGGATCAAGGGGGGGAGAGACATGGAAATCGAGGGACGGGTCTTTGTCGT
401      --------------------------------------------------      450
         TCCTAGTTCCCCCCCTCTCTGTACCTTTAGCTCCCTGCCCAGAAACAGCA

R   I   K   G   G   R   D   M   E   I   E   G   R   V   F   V   V

CACGGGCGCCGCATCGGGTCTGGGGGCGGCCTCGGCGCGGATGCTGGCCC
451      --------------------------------------------------      500
         GTGCCCGCGGCGTAGCCCAGACCCCCGCCGGAGCCGCGCCTACGACCGGG

T   G   A   A   S   G   L   G   A   A   S   A   R   M   L   A   Q

AAGGCGGCGCGAAGGTCGTGCTGGCCGATCTGGCGGAACCGAAGGACGCG
501      --------------------------------------------------      550
         TTCCGCCGCGCTTCCAGCACGACCGGCTAGACCGCCTTGGCTTCCTGCGC

G   G   A   K   V   V   L   A   D   L   A   E   P   K   D   A

CCCGAAGGCGCGGTTCACGCGGCCTGCGACGTGACCGACGCGACCGCTGC
551      --------------------------------------------------      600
         GGGCTTCCGCGCCAAGTGCGCCGGACGCTGCACTGGCTGCGCTGGCGACG

```
     GCAGACGGCCATCGCGCTGGCGACCGACCGCTTCGGCAGGCTGGACGGCC
601  --------------------------------------------------  650
     CGTCTGCCGGTAGCGCGACCGCTGGCTGGCGAAGCCGTCCGACCTGCCGG

Q  T  A  I  A  L  A  T  D  R  F  G  R  L  D  G  L

TTGTGAACTGCGCGGGCATCGCGCCGGCCGAACGGATGCTGGGCCGCGAC
651  --------------------------------------------------  700
     AACACTTGACGCGCCCGTAGCGCGGCCGGCTTGCCTACGACCCGGCGCTG

V  N  C  A  G  I  A  P  A  E  R  M  L  G  R  D

GGGCCGCATGGACTGGACAGCTTTGCCCGTGCGGTCACGATCAACCTGAT
701  --------------------------------------------------  750
     CCCGGCGTACCTGACCTGTCGAAACGGGCACGCCAGTGCTAGTTGGACTA

G  P  H  G  L  D  S  F  A  R  A  V  T  I  N  L  I

CGGCAGCTTCAACATGGCCCGCCTTGCAGCCGAGGCGATGGCCCGGAACG
751  --------------------------------------------------  800
     GCCGTCGAAGTTGTACCGGGCGGAACGTCGGCTCCGCTACCGGGCCTTGC

G  S  F  N  M  A  R  L  A  A  E  A  M  A  R  N  E

AGCCCGTCCGGGGCGAGCGTGGCGTGATCGTCAACACGGCCTCGATCGCG
801  --------------------------------------------------  850
     TCGGGCAGGCCCCGCTCGCACCGCACTAGCAGTTGTGCCGGAGCTAGCGC

P  V  R  G  E  R  G  V  I  V  N  T  A  S  I  A

GCGCAGGACGGACAGATCGGACAGGTCGCCTATGCGGCCAGCAAGGCGGG
851  --------------------------------------------------  900
     CGCGTCCTGCCTGTCTAGCCTGTCCAGCGGATACGCCGGTCGTTCCGCCC

A  Q  D  G  Q  I  G  Q  V  A  Y  A  A  S  K  A  G
```

```
            CGTGGCGGGCATGACGCTGCCGATGGCCCGCGACCTTGCGCGGCACGGCA
901         --------------------------------------------------  950
            GCACCGCCCGTACTGCGACGGCTACCGGGCGCTGGAACGCGCCGTGCCGT

V   A   G   M   T   L   P   M   A   R   D   L   A   R   H   G   I

TCCGCGTCATGACCATCGCGCCCGGCATCTTCCGCACCCCGATGCTGGAG
951         --------------------------------------------------  1000
            AGGCGCAGTACTGGTAGCGCGGGCCGTAGAAGGCGTGGGGCTACGACCTC

R   V   M   T   I   A   P   G   I   F   R   T   P   M   L   E

GGGCTGCCGCAGGACGTTCAGGACAGCCTGGGCGCGGCGGTGCCCTTCCC
1001        --------------------------------------------------  1050
            CCCGACGGCGTCCTGCAAGTCCTGTCGGACCCGCGCCGCCACGGGAAGGG

G   L   P   Q   D   V   Q   D   S   L   G   A   A   V   P   F   P

CTCGCGGCTGGGAGAGCCGTCGGAATACGCGGCGCTGTTGCACCACATCA
1051        --------------------------------------------------  1100
            GAGCGCCGACCCTCTCGGCAGCCTTATGCGCCGCGACAACGTGGTGTAGT

S   R   L   G   E   P   S   E   Y   A   A   L   L   H   H   I   I

TCGCGAACCCCATGCTGAACGGAGAGGTCATCCGCCTCGACGGCGCATTG
1101        --------------------------------------------------  1150
            AGCGCTTGGGGTACGACTTGCCTCTCCAGTAGGCGGAGCTGCCGCGTAAC

A   N   P   M   L   N   G   E   V   I   R   L   D   G   A   L

CGCATGGCCCCCAAGTGAAGGAGCGTTTCATGGACCCCATCGTCATCACC
1151        --------------------------------------------------  1200
            GCGTACCGGGGGTTCACTTCCTCGCAAAGTACCTGGGGTAGCAGTAGTGG

R   M   A   P   K   *           M   D   P   I   V   I   T
                                              orf-1→
```

```
       GGCGCGATGCGCACCCCGATGGGGCATTCCAGGGCGATCTTGCCGCGAT
1201   ------------------------------------------------- 1250
       CCGCGCTACGCGTGGGGCTACCCCCGTAAGGTCCCGCTAGAACGGCGCTA
```

G  A  M  R  T  P  M  G  A  F  Q  G  D  L  A  A  M

```
       GGATGCCCCGACCCTTGGCGCGGACGCGATCCGCGCCGCGCTGAACGGCC
1251   ------------------------------------------------- 1300
       CCTACGGGGCTGGGAACCGCGCCTGCGCTAGGCGCGGCGCGACTTGCCGG
```

D  A  P  T  L  G  A  D  A  I  R  A  A  L  N  G  L

```
       TGTCGCCCGACATGGTGGACGAGGTGCTGATGGGCTGCGTCCTCGCCGCG
1301   ------------------------------------------------- 1351
       ACAGCGGGCTGTACCACCTGCTCCACGACTACCCGACGCAGGAGCGGCGC
```

S  P  D  M  V  D  E  V  L  M  G  C  V  L  A  A

```
       GGCCAGGGTCAGGCACCGGCACGTCAGGCGGCGCTTGGCGCCGGACTGCC
1351   ------------------------------------------------- 1400
       CCGGTCCCAGTCCGTGGCCGTGCAGTCCGCCGCGAACCGCGGCCTGACGG
```

G  Q  G  Q  A  P  A  R  Q  A  A  L  G  A  G  L  P

```
       GCTGTCGACGGGCACGACCACCATCAACGAGATGTGCGGATCGGGCATGA
1401   ------------------------------------------------- 1450
       CGACAGCTGCCCGTGCTGGTGGTAGTTGCTCTACACGCCTAGCCCGTACT
```

L  S  T  G  T  T  T  I  N  E  M  C  G  S  G  M  K

```
       AGGCCGCGATGCTGGGCCATGACCTGATCGCCGCGGGATCGGCGGGCATC
1451   ------------------------------------------------- 1500
       TCCGGCGCTACGACCCGGTACTGGACTAGCGGCGCCCTAGCCGCCCGTAG
```

A  A  M  L  G  H  D  L  I  A  A  G  S  A  G  I

```
             GTCGTCGCCGGCGGGATGGAGAGCATGTCGAACGCCCCCTACCTGCTGCC
     1501    --------------------------------------------------  1550
             CAGCAGCGGCCGCCCTACCTCTCGTACAGCTTGCGGGGGATGGACGACGG

V    V    A    G    G    M    E    S    M    S    N    A    P    Y    L    L    P

CAAGGCGCGGTCGGGGATGCGCATGGGCCATGACCGTGTGCTGGATCACA
     1551    --------------------------------------------------  1600
             GTTCCGCGCCAGCCCCTACGCGTACCCGGTACTGGCACACGACCTAGTGT

K    A    R    S    G    M    R    M    G    H    D    R    V    L    D    H    M

TGTTCCTCGACGGGTTGGAGGACGCCTATGACAAGGGCCGCCTGATGGGC
     1601    --------------------------------------------------  1650
             ACAAGGAGCTGCCCAACCTCCTGCGGATACTGTTCCCGGCGGACTACCCG

F    L    D    G    L    E    D    A    Y    D    K    G    R    L    M    G

ACCTTCGCCGAGGATTGCGCCGGCGATCACGGTTTCACCCGCGAGGCGCA
     1651    --------------------------------------------------  1700
             TGGAAGCGGCTCCTAACGCGGCCGCTAGTGCCAAAGTGGGCGCTCCGCGT

T    F    A    E    D    C    A    G    D    H    G    F    T    R    E    A    Q

GGACGACTATGCGCTGACCAGCCTGGCCCGCGCGCAGGACGCCATCGCCA
     1701    --------------------------------------------------  1750
             CCTGCTGATACGCGACTGGTCGGACCGGGCGCGCGTCCTGCGGTAGCGGT

D    D    Y    A    L    T    S    L    A    R    A    Q    D    A    I    A    S

GCGGTGCCTTCGCCGCCGAGATCGCGCCCGTGACCGTCACGGCACGCAAG
     1751    --------------------------------------------------  1800
             CGCCACGGAAGCGGCGGCTCTAGCGCGGGCACTGGCAGTGCCGTGCGTTC

```
      GTGCAGACCACCGTCGATACCGACGAGATGCCCGGCAAGGCCCGCCCCGA
1801  --------------------------------------------------  1850
      CACGTCTGGTGGCAGCTATGGCTGCTCTACGGGCCGTTCCGGGCGGGGCT

V  Q  T  T  V  D  T  D  E  M  P  G  K  A  R  P  E

GAAGATCCCCCATCTGAAGCCCGCCTTCCGTGACGGTGGCACGGTCACGG
1851  --------------------------------------------------  1900
      CTTCTAGGGGGTAGACTTCGGGCGGAAGGCACTGCCACCGTGCCAGTGCC

K  I  P  H  L  K  P  A  F  R  D  G  G  T  V  T  A

CGGCGAACAGCTCGTCGATCTCGGACGGGGCGGCGGCGCTGGTGATGATG
1901  --------------------------------------------------  1950
      GCCGCTTGTCGAGCAGCTAGAGCCTGCCCCGCCGCCGCGACCACTACTAC

A  N  S  S  S  I  S  D  G  A  A  A  L  V  M  M

CGCCAGTCGCAGGCCGAGAAGCTGGGCCTGACGCCGATCGCGCGGATCAT
1951  --------------------------------------------------  2000
      GCGGTCAGCGTCCGGCTCTTCGACCCGGACTGCGGCTAGCGCGCCTAGTA

R  Q  S  Q  A  E  K  L  G  L  T  P  I  A  R  I  I

CGGTCATGCGACCCATGCCGACCGTCCCGGCCTGTTCCCGACGGCCCCCA
2001  --------------------------------------------------  2050
      GCCAGTACGCTGGGTACGGCTGGCAGGGCCGGACAAGGGCTGCCGGGGGT

G  H  A  T  H  A  D  R  P  G  L  F  P  T  A  P  I

TCGGCGCGATGCGCAAGCTGCTGGACCGCACGGACACCCGCCTTGGCGAT
2051  --------------------------------------------------  2100
      AGCCGCGCTACGCGTTCGACGACCTGGCGTGCCTGTGGGCGGAACCGCTA

G  A  M  R  K  L  L  D  R  T  D  T  R  L  G  D
```

```
       TACGACCTGTTCGAGGTGAACGAGGCATTCGCCGTCGTCGCCATGATCGC
2101   --------------------------------------------------  2150
       ATGCTGGACAAGCTCCACTTGCTCCGTAAGCGGCAGCAGCGGTACTAGCG

Y  D  L  F  E  V  N  E  A  F  A  V  V  A  M  I  A

GATGAAGGAGCTTGGCCTGCCACACGATGCCACGAACATCAACGGCGGGG
2151   --------------------------------------------------  2200
       CTACTTCCTCGAACCGGACGGTGTGCTACGGTGCTTGTAGTTGCCGCCCC

M  K  E  L  G  L  P  H  D  A  T  N  I  N  G  G  A

CCTGCGCGCTTGGGCATCCCATCGGCGCGTCGGGGGCGCGGATCATGGTC
2201   --------------------------------------------------  2250
       GGACGCGCGAACCCGTAGGGTAGCCGCGCAGCCCCCGCGCCTAGTACCAG

C  A  L  G  H  P  I  G  A  S  G  A  R  I  M  V

ACGCTGCTGAACGCGATGGCGGCGCGGGGCGCGACGCGCGGGGCCGCATC
2251   --------------------------------------------------  2300
       TGCGACGACTTGCGCTACCGCCGCGCCCCGCGCTGCGCGCCCCGGCGTAG

T  L  L  N  A  M  A  A  R  G  A  T  R  G  A  A  S

CGTCTGCATCGGCGGGGGCGAGGCGACGGCCATCGCGCTGGAACGGCTGA
2301   --------------------------------------------------  2350
       GCAGACGTAGCCGCCCCCGCTCCGCTGCCGGTAGCGCGACCTTGCCGACT

V  C  I  G  G  G  E  A  T  A  I  A  L  E  R  L  S

GCTAATTCATTTGCGCGAATCCGCGTTTTTCGTGCACGATGGGGGAACCG
2351   --------------------------------------------------  2400
       CGATTAAGTAAACGCGCTTAGGCGCAAAAAGCACGTGCTACCCCCTTGGC

```
      GAAACGGCCACGCCTGTTGTGGTTGCGTCGACCTGTCTTCGGGCCATGCC
2401  -------------------------------------------------- 2450
      CTTTGCCGGTGCGGACAACACCAACGCAGCTGGACAGAAGCCCGGTACGG

CGTGACGCGATGTGGCAGGCGCATGGGGCGTTGCCGATCCGGTCGCATGA
2451  -------------------------------------------------- 2500
      GCACTGCGCTACACCGTCCGCGTACCCCGCAACGGCTAGGCCAGCGTACT

CTGACGCAACGAAGGCACCGATGACGCCCAAGCAGCAATTCCCCCTACGC
2501  -------------------------------------------------- 2550
      GACTGCGTTGCTTCCGTGGCTACTGCGGGTTCGTCGTTAAGGGGGATGCG crtE  -►     M   T   P   K   Q   Q   F   P   L   R GATCTGGTCGAGATCAGGCTGGCGCAGATCTCGGGCCAGTTCGGCGTGGT
2551  -------------------------------------------------- 2600
      CTAGACCAGCTCTAGTCCGACCGCGTCTAGAGCCCGGTCAAGCCGCACCA

D   L   V   E   I   R   L   A   Q   I   S   G   Q   F   G   V   V

CTCGGCCCCGCTCGGCGCGGCCATGAGCGATGCCGCCCTGTCCCCCGGCA
2601  -------------------------------------------------- 2650
      GAGCCGGGGCGAGCCGCGCCGGTACTCGCTACGGCGGGACAGGGGGCCGT

S   A   P   L   G   A   A   M   S   D   A   A   L   S   P   G   K

AACGCTTTCGCGCCGTGCTGATGCTGATGGTCGCCGAAAGCTCGGGCGGG
2651  -------------------------------------------------- 2700
      TTGCGAAAGCGCGGCACGACTACGACTACCAGCGGCTTTCGAGCCCGCCC

R   F   R   A   V   L   M   L   M   V   A   E   S   S   G   G
```

```
         GTCTGCGATGCGATGGTCGATGCCGCCTGCGCGGTCGAGATGGTCCATGC
2701     --------------------------------------------------  2750
         CAGACGCTACGCTACCAGCTACGGCGGACGCGCCAGCTCTACCAGGTACG

V   C   D   A   M   V   D   A   A   C   A   V   E   M   V   H   A

CGCATCGCTGATCTTCGACGACATGCCCTGCATGGACGATGCCAGGACCC
2751     --------------------------------------------------  2800
         GCGTAGCGACTAGAAGCTGCTGTACGGGACGTACCTGCTACGGTCCTGGG

A   S   L   I   F   D   D   M   P   C   M   D   D   A   R   T   R

GTCGCGGTCAGCCCGCCACCCATGTCGCCCATGGCGAGGGGCGCGCGGTG
2801     --------------------------------------------------  2850
         CAGCGCCAGTCGGGCGGTGGGTACAGCGGGTACCGCTCCCCGCGCGCCAC

R   G   Q   P   A   T   H   V   A   H   G   E   G   R   A   V

CTTGCGGGCATCGCCCTGATCACCGAGGCCATGCGGATTTTGGGCGAGGC
2851     --------------------------------------------------  2900
         GAACGCCCGTAGCGGGACTAGTGGCTCCGGTACGCCTAAAACCCGCTCCG

L   A   G   I   A   L   I   T   E   A   M   R   I   L   G   E   A

GCGCGGCGCGACGCCGGATCAGCGCGCAAGGCTGGTCGCATCCATGTCGC
2901     --------------------------------------------------  2950
         CGCGCCGCGCTGCGGCCTAGTCGCGCGTTCCGACCAGCGTAGGTACAGCG

R   G   A   T   P   D   Q   R   A   R   L   V   A   S   M   S   R

GCGCGATGGGACCGGTGGGGCTGTGCGCAGGGCAGGATCTGGACCTGCAC
2951     --------------------------------------------------  3000
         CGCGCTACCCTGGCCACCCCGACACGCGTCCCGTCCTAGACCTGGACGTG

```
         GCCCCCAAGGACGCCGCCGGGATCGAACGTGAACAGGACCTCAAGACCGG
3001     -------------------------------------------------- 3050
         CGGGGGTTCCTGCGGCGGCCCTAGCTTGCACTTGTCCTGGAGTTCTGGCC

A   P   K   D   A   A   G   I   E   R   E   Q   D   L   K   T   G

CGTGCTGTTCGTCGCGGGCCTCGAGATGCTGTCCATTATTAAGGGTCTGG
3051     -------------------------------------------------- 3100
         GCACGACAAGCAGCGCCCGGAGCTCTACGACAGGTAATAATTCCCAGACC

V   L   F   V   A   G   L   E   M   L   S   I   I   K   G   L   D

ACAAGGCCGAGACCGAGCAGCTCATGGCCTTCGGGCGTCAGCTTGGTCGG
3101     -------------------------------------------------- 3150
         TGTTCCGGCTCTGGCTCGTCGAGTACCGGAAGCCCGCAGTCGAACCAGCC

K   A   E   T   E   Q   L   M   A   F   G   R   Q   L   G   R

GTCTTCCAGTCCTATGACGACCTGCTGGACGTGATCGGCGACAAGGCCAG
3151     -------------------------------------------------- 3200
         CAGAAGGTCAGGATACTGCTGGACGACCTGCACTAGCCGCTGTTCCGGTC

V   F   Q   S   Y   D   D   L   L   D   V   I   G   D   K   A   S

CACCGGCAAGGATACGGCGCGCGACACCGCCGCCCCCGGCCCAAAGGGCG
3201     -------------------------------------------------- 3250
         GTGGCCGTTCCTATGCCGCGCGCTGTGGCGGCGGGGCCGGGTTTCCCGC

T   G   K   D   T   A   R   D   T   A   A   P   G   P   K   G   G

GCCTGATGGCGGTCGGACAGATGGGCGACGTGGCGCAGCATTACCGCGCC
3251     -------------------------------------------------- 3300
         CGGACTACCGCCAGCCTGTCTACCCGCTGCACCGCGTCGTAATGGCGCGG

L   M   A   V   G   Q   M   G   D   V   A   Q   H   Y   R   A
```

```
            AGCCGCGCGCAACTGGACGAGCTGATGCGCACCCGGCTGTTCCGCGGGGG
3301        --------------------------------------------------      3350
            TCGGCGCGCGTTGACCTGCTCGACTACGCGTGGGCCGACAAGGCGCCCC

S   R   A   Q   L   D   E   L   M   R   T   R   L   F   R   G   G

GCAGATCGCGGACCTGCTGGCCCGCGTGCTGCCGCATGACATCCGCCGCA
3351        --------------------------------------------------      3400
            CGTCTAGCGCCTGGACGACCGGGCGCACGACGGCGTACTGTAGGCGGCGT

Q   I   A   D   L   L   A   R   V   L   P   H   D   I   R   R   S

GCGCCTAGGCGCGCGGTCGGGTCCACAGGCCGTCGCGGCTGATTTCGCCG
3401        --------------------------------------------------      3450
            CGCGGATCCGCGCGCCAGCCCAGGTGTCCGGCAGCGCCGACTAAAGCGGC

A   *
             *   A   R   P   R   T   W   L   G   D   R   S   I   E   G

CCGCGCAGGCGCGATGCGGCCGCGTCCAAGCCTCCGCGCGCCAGAAGCCC
3451        --------------------------------------------------      3500
            GGCGCGTCCGCGCTACGCCGGCGCAGGTTCGGAGGCGCGCGGTCTTCGGG

G   R   L   R   S   A   A   A   D   L   G   G   R   A   L   L   G

GATCTTGGCAGCCTTCGACGTGCTGATCCGCTGGCGATAGGCCTCGGGGC
3501        --------------------------------------------------      3550
            CTAGAACCGTCGGAAGCTGCACGACTAGGCGACCGCTATCCGGAGCCCCG

I   K   A   A   K   S   T   S   I   R   Q   R   Y   A   E   P

CACCCTGCCGGATGCGCGTCCCGATTGCGCGATAGATACGCAGCGCGGCG
3551        --------------------------------------------------      3600
            GTGGGACGGCCTACGCGCAGGGCTAACGCGCTATCTATGCGTCGCGCCGC

```
       GCGATCGACCACGCGCAGCGCGGCGGCAGATGCGGAAGCCCCTGCCGCGC
3601   --------------------------------------------------  3650
       CGCTAGCTGGTGCGCGTCGCGCCGCCGTCTACGCCTTCGGGGACGGCGCG

A  I  S  W  A  C  R  P  P  L  H  P  L  G  Q  R  A

CGAGGCATAATAGGGCTCGGCCGCGTCAAGCAGGCGGATGATGACGGAAT
3651   --------------------------------------------------  3700
       GCTCCGTATTATCCCGAGCCGGCGCAGTTCGTCCGCCTACTACTGCCTTA

S  A  Y  Y  P  E  A  A  D  L  L  R  I  I  V  S

AGAGCGCGTCCGAAGGCACCGGACCCTCAACCGTCGCCCCGCCTCGGCC
3701   --------------------------------------------------  3750
       TCTCGCGCAGGCTTCCGTGGCCTGGGAGTTGGCAGCGGGGGCGGAGCCGG

Y  L  A  D  S  P  V  P  G  E  V  T  A  G  A  E  A

AGCCAGTCGGCAGGCAGATAGCAGCGCCCGATGGCGGCATCGTCGATCAC
3751   --------------------------------------------------  3800
       TCGGTCAGCCGTCCGTCTATCGTCGCGGGCTACCGCCGTAGCAGCTAGTG

L  W  D  A  P  L  Y  C  R  G  I  A  A  D  D  I  V

GTCGCGAGCGATGTTCGTCAGCTGGAACGCAAGGCCCAGATCGCAGGCGC
3801   --------------------------------------------------  3850
       CAGCGCTCGCTACAAGCAGTCGACCTTGCGTTCCGGGTCTAGCGTCCGCG

D  R  A  I  N  T  L  Q  F  A  L  G  L  D  C  A

GATCCAGCACCGCATCGTCCTGCACGCCCATCACCCGCGCCATCATCACG
3851   --------------------------------------------------  3900
       CTAGGTCGTGGCGTAGCAGGACGTGCGGGTAGTGGGCGCGGTAGTAGTGC

R  D  L  V  A  D  D  Q  V  G  M  V  R  A  M  M  V
```

```
      CCCACGACCCCCGCGACGTGGTAGGAATATTCCAGCACGTCATCCAGGCT
3901  --------------------------------------------------  3950
      GGGTGCTGGGGGCGCTGCACCATCCTTATAAGGTCGTGCAGTAGGTCCGA

G  V  V  G  A  V  H  Y  S  Y  E  L  V  D  D  L  S

GCGGTATTCGCGATCCGCGACATCCATCGCGAAACCCTCGATCAGGTCCA
3951  --------------------------------------------------  4000
      CGCCATAAGCGCTAGGCGCTGTAGGTAGCGCTTTGGGAGCTAGTCCAGGT

R  Y  E  R  D  A  V  D  M  A  F  G  E  I  L  D

TCGGCCAAAGGTCCGGGAAATCATGCCGCCGGGCGACCTGGCGCAGCGCC
4001  --------------------------------------------------  4050
      AGCCGGTTTCCAGGCCCTTTAGTACGGCGGCCCGCTGGACCGCGTCGCGG

M  P  W  L  D  P  F  D  H  R  R  A  V  Q  R  L  A

GCGAAGGGCGGCGACATCGGGCCGTCCTCGTGCAGCGCGGCCAGCGTGTC
4051  --------------------------------------------------  4100
      CGCTTCCCGCCGCTGTAGCCCGGCAGGAGCACGTCGCGCCGGTCGCACAG

A  F  P  P  S  M  P  G  D  E  H  L  A  A  L  T  D

GGCGCGCAGCGCCCCCAGCCGCGCCTGTGGGTCGCCGCCCGCCTCGGGGG
4101  --------------------------------------------------  4150
      CCGCGCGTCGCGGGGGTCGGCGCGGACACCCAGCGGCGGGCGGAGCCCCC

A  R  L  A  G  L  R  A  Q  P  D  G  G  A  E  P

CAGAACCCATCACCTGCCCGTCGATCACGTCATCCGCATGCCTGCACCAG
4151  --------------------------------------------------  4200
      GTCTTGGGTAGTGGACGGGCAGCTAGTGCAGTAGGCGTACGGACGTGGTC

```
             GCATAGAGCATGACCGTATCCTCGCGGATGCCGGGCGGCATCAGCTTGGC
    4201     --------------------------------------------------  4250
             CGTATCTCGTACTGGCATAGGAGCGCCTACGGCCCGCCGTAGTCGAACCG

A   Y   L   M   V   T   D   E   R   I   G   P   P   M   L   K   A

CGCCTGCGCGAAGCTTTGCGAACCCTGCGCGATGGCCGCTTCGGAAGTCG
    4251     --------------------------------------------------  4300
             GCGGACGCGCTTCGAAACGCTTGGGACGCGCTACCGGCGAAGCCTTCAGC

A   Q   A   F   S   Q   S   G   Q   A   I   A   A   E   S   T

CCGTCAGATCGGTCATGCGACGGCCAGGTCCGACAGCATGACCTGCGCCG
    4301     --------------------------------------------------  4350
             GGCAGTCTAGCCAGTACGCTGCCGGTCCAGGCTGTCGTACTGGACGCGGC

*   A   V   A   L   D   S   L   M   V   Q   A
              A   T   L   D   T   M
               ← ← crtB TGGCCTTGGCGCTGCCAACGACACCCGGGATGCCCGCACCCGGATGCGTG
    4351     --------------------------------------------------  4400
             ACCGGAACCGCGACGGTTGCTGTGGGCCCTACGGGCGTGGGCCTACGCAC

T   A   K   A   S   G   V   V   G   P   I   G   A   G   P   H   T

CCCGCCCCCACGATGTAGAAGTTCGGGATCGCGCGGTCGCGGTTATGCGG
    4401     --------------------------------------------------  4450
             GGGCGGGGGTGCTACATCTTCAAGCCCTAGCGCGCCAGCGCCAATACGCC

G   A   G   V   I   Y   F   N   P   I   A   R   D   R   N   H   P

GCGGAACCAGGCGGATTGCGTCAGGATCGGCTCGACCGAGAAGGCGCTGC
    4451     --------------------------------------------------  4500
             CGCCTTGGTCCGCCTAACGCAGTCCTAGCCGAGCTGGCTCTTCCGCGACG

```
        CGTGATGGGCCGACAGTTCGGTGCTGAAATCGGCGGGGCTGAAGATGCGG
4501    --------------------------------------------------  4550
        GCACTACCCGGCTGTCAAGCCACGACTTTAGCCGCCCCGACTTCTACGCC

G   H   H   A   S   L   E   T   S   F   D   A   P   S   F   I   R

CTGACGGTCAGGTGCTTGCGCAGGTCGGGGATGGCGCGGCGCTCCAGTTC
4551    --------------------------------------------------  4600
        GACTGCCAGTCCACGAACGCGTCCAGCCCCTACCGCGCCGCGAGGTCAAG

S   V   T   L   H   K   R   L   D   P   I   A   R   R   E   L   E

CTCGAAGATGCGCTCGGCATAGCCCGGGGCCTCGGCTTCCCAATCGACAT
4601    --------------------------------------------------  4650
        GAGCTTCTACGCGAGCCGTATCGGGCCCCGGAGCCGAAGGGTTAGCTGTA

E   F   I   R   E   A   Y   G   P   A   E   A   E   W   D   V

CGGCGCGGCCCAGATGCGGAACGGGCGCAAGGACGTAATGCGTGGACATC
4651    --------------------------------------------------  4700
        GCCGCGCCGGGTCTACGCCTTGCCCGCGTTCCTGCATTACGCACCTGTAG

D   A   R   G   L   H   P   V   P   A   L   V   Y   H   T   S   M

CCCTCGGGGGCCAGGCTGGGATCGGTCACGCAGGGCGAATGCAGATACAT
4701    --------------------------------------------------  4750
        GGGAGCCCCCGGTCCGACCCTAGCCAGTGCGTCCCGCTTACGTCTATGTA

G   E   P   A   L   S   P   D   T   V   C   P   S   H   L   Y   M

CGAGAAATCGTCCGGCAGGCGTGGCCCGTTGAAGATCTCGTTCACCAGCC
4751    --------------------------------------------------  4800
        GCTCTTTAGCAGGCCGTCCGCACCGGGCAACTTCTAGAGCAAGTGGTCGG

```
        CCTTGTAGCGCGGGCCGAAGATGACGCTGTGGTGGGCCAGGTTCTCGGGG
4801    --------------------------------------------------  4850
        GGAACATCGCGCCCGGCTTCTACTGCGACACCACCCGGTCCAAGAGCCCC

G  K  Y  R  P  G  F  I  V  S  H  H  A  L  N  E  P

CGCTTGGACAGGCCGAAATGCAGCACGAACAGCGACATCGACCAGCGCTG
4851    --------------------------------------------------  4900
        GCGAACCTGTCCGGCTTTACGTCGTGCTTGTCGCTGTAGCTGGTCGCGAC

R  K  S  L  G  F  H  L  V  F  L  S  M  S  W  R  Q

CCGGTTCAGGATCGCGGCCTTGGTGCGCCCGCGGCGGGTATGGCCCAGCA
4901    --------------------------------------------------  4950
        GGCCAAGTCCTAGCGCCGGAACCACGCGGGCGCCGCCCATACCGGGTCGT

R  N  L  I  A  A  K  T  R  G  R  R  T  H  G  L

GGTCGCGATAGCTGTGCATCACGTCGCCGTTGCTGGCCACCGTATCCGCG
4951    --------------------------------------------------  5000
        CCAGCGCTATCGACACGTAGTGCAGCGGCAACGACCGGTGGCATAGGCGC

L  D  R  Y  S  H  M  V  D  G  N  S  A  V  T  D  A

CGCAACTGCCGCCCGTCCAGCAGCGTGACGCCCGTGGCGCGATCGCCCTC
5001    --------------------------------------------------  5050
        GCGTTGACGGCGGGCAGGTCGTCGCACTGCGGGCACCGCGCTAGCGGGAG

R  L  Q  R  G  D  L  L  T  V  G  T  A  R  D  G  E

GGTGTCGATCCGCGTGACGCGGGCATTCAGCAGCAGCGTGCCGCCAAGAC
5051    --------------------------------------------------  5100
        CCACAGCTAGGCGCACTGCGCCCGTAAGTCGTCGTCGCACGGCGGTTCTG

T  D  I  R  T  V  R  A  N  L  L  L  T  G  G  L
```

```
       GCTCGAACAGGGCGACCATGCCCGCGACCAGCTGGTTGGTGCCGCCCTTG
5101   --------------------------------------------------  5150
       CGAGCTTGTCCCGCTGGTACGGGCGCTGGTCGACCAACCACGGCGGGAAC

R   E   F   L   A   V   M   G   A   V   L   Q   N   T   G   G   K

GCGAACCAGACGCCGCCGCGCCGTTCCAGCGCATGGATCAGCGCATAGAT
5151   --------------------------------------------------  5200
       CGCTTGGTCTGCGGCGGCGCGGCAAGGTCGCGTACCTAGTCGCGTATCTA

A   F   W   V   G   G   R   R   E   L   A   H   I   L   A   Y   I

CGAGCTGGTCGAAAACGGGTTCCCGCCGACCAGCAGCGTGTGGAACGAGA
5201   --------------------------------------------------  5250
       GCTCGACCAGCTTTTGCCCAAGGGCGGCTGGTCGTCGCACACCTTGCTCT

S   S   T   S   F   P   N   G   G   V   L   L   T   H   F   S

AGGCCTGCCGCAGATGCGGGTCCTGGATGAAGCGCGCCACCATGCTGTGG
5251   --------------------------------------------------  5300
       TCCGGACGGCGTCTACGCCCAGGACCTACTTCGCGCGGTGGTACGACACC

F   A   Q   R   L   H   P   D   Q   I   F   R   A   V   M   S   H

ACCGAGCGGTATGCCTGCAGGCGCATCAGCGCCGGCGCGGCGTTCAGCAT
5301   --------------------------------------------------  5350
       TGGCTCGCCATACGGACGTCCGCGTAGTCGCGGCCGCGCCGCAAGTCGTA

V   S   R   Y   A   Q   L   R   M   L   A   P   A   A   N   L   M

CTGGCCCAGCTTCAGGAAGGGCGTGGTCCCCAGCTTCAGATACCCCTCGC
5351   --------------------------------------------------  5400
       GACCGGGTCGAAGTCCTTCCCGCACCAGGGGTCGAAGTCTATGGGGAGCG

```
                GATAGACCTCCTCGGCGTAATCGTGGAAGCGGCGATAGCCATCGACATCG
     5401       --------------------------------------------------    5450
                CTATCTGGAGGAGCCGCATTAGCACCTTCGCCGCTATCGGTAGCTGTAGC

R   Y   V   E   E   A   Y   D   H   F   R   R   Y   G   D   V   D

GCGGGATTGAAGGAGGCGACCTGGCGGATCAGCTCGTCGTCGTCGTTCAC
     5451       --------------------------------------------------    5500
                CGCCCTAACTTCCTCCGCTGGACCGCCTAGTCGAGCAGCAGCAGCAAGTG

A   P   N   F   S   A   V   Q   R   I   L   E   D   D   D   N   V

GTATTCGAAGCTGCGGCCGTCCGCCCATGTCAGCCGGTAGAAGGGCGAGA
     5501       --------------------------------------------------    5550
                CATAAGCTTCGACGCCGGCAGGCGGGTACAGTCGGCCATCTTCCCGCTCT

Y   E   F   S   R   G   D   A   W   T   L   R   Y   F   P   S

CCGGCAGCAGCGTCACGTCACGCTCCATCGGTTGGCCGCTGAGGGCCCAC
     5551       --------------------------------------------------    5600
                GGCCGTCGTCGCAGTGCAGTGCGAGGTAGCCAACCGGCGACTCCCGGGTG

V   P   L   L   T   V   D   R   E   M   P   Q   G   S   L   A   W

AGCTCTCGCAGGCTGTCGGGGTCGGTCACGACCGTCGGGCCTGCATCGAA
     5601       --------------------------------------------------    5650
                TCGAGAGCGTCCGACAGCCCCAGCCAGTGCTGGCAGCCCGGACGTAGCTT

L   E   R   L   S   D   P   D   T   V   V   T   P   G   A   D   F

GACGTGGCCCTGATCGTTCCAGACATAGGCGCGGCCGCCGGGCTTGTCGC
     5651       --------------------------------------------------    5700
                CTGCACCGGGACTAGCAAGGTCTGTATCCGCGCCGGCGGCCCGAACAGCG
                 V   H   G   Q   D   N   W   V   Y   A   R   G   G   P   K   D
```

*FIG. 7S*

```
          GGGCCTCGACGATGGTGGTCGCGATGCCGGCCGATTGCAGGCGGATGGCA
    5701  --------------------------------------------------  5750
          CCCGGAGCTGCTACCACCAGCGCTACGGCCGGCTAACGTCCGCCTACCGT

R   A   E   V   I   T   T   A   I   G   A   S   Q   L   R   I   A

AGCGCAAGCCCGCCGAAACCTGCGCCGATGACGATGGCGGAACTCATGCT
    5751  --------------------------------------------------  5800
          TCGCGTTCGGGCGGCTTTGGACGCGGCTACTGCTACCGCCTTGAGTACGA

L   A   L   G   G   F   G   A   G   I   V   I   A   S   S   M ←── crtI
                                                           * A CTCTCCTGCAGCAGGGGGCGTTCGGGCAGGCAGCGCACGGCCTGCGACAG
    5801  --------------------------------------------------  5850
          GAGAGGACGTCGTCCCCCGCAAGCCCGTCCGTCGCGTGCCGGACGCTGTC

R   E   Q   L   L   P   R   E   P   L   C   R   V   A   Q   S   L

CGGAATGGGCGGGCGTCCGGTGACGATGCGAAGCCGGTCGGCCAATGTCA
    5851  --------------------------------------------------  5900
          GCCTTACCCGCCCGCAGGCCACTGCTACGCTTCGGCCAGCCGGTTACAGT

P   I   P   P   R   G   T   V   I   R   L   R   D   A   L   T

GGCGCCCGGCATAGAAGCGCTCGATCAGCGGCTGCGGCAGGCGGTAGAAC
    5901  --------------------------------------------------  5950
          CCGCGGGCCGTATCTTCGCGAGCTAGTCGCCGACGCCGTCCGCCATCTTG

L   R   G   A   Y   F   R   E   I   L   P   Q   P   L   R   Y   F

CGCTGCAGCAGGCGATAGCGACGGTCGGGCGGGCAGCCGCGGAACAGCAT
    5951  --------------------------------------------------  6000
          GCGACGTCGTCCGCTATCGCTGCCAGCCCGCCCGTCGGCGCCTTGTCGTA

```
             CCGGTTCAGCAGCCGCAGGAAGCGGTCGCGATCCGCGCGATCGATGGCCC
     6001    --------------------------------------------------    6050
             GGCCAAGTCGTCGGCGTCCTTCGCCAGCGCTAGGCGCGCTAGCTACCGGG

R   N   L   L   P   L   F   R   D   R   D   A   R   D   I   A

AGCCGCGCACCGCGCGACGGGCGGACGCGGTCGTCAGGTCGCGCGCCGCG
     6051    --------------------------------------------------    6100
             TCGGCGCGTGGCGCGCTGCCCGCCTGCGCCAGCAGTCCAGCGCGCGGCGC

W   G   R   V   A   R   R   A   S   A   T   T   L   D   R   A   A

ATGGCATCCGCGACCTGCGCGGCATAGGGCAGCGAATATCCGGTGACGGG
     6101    --------------------------------------------------    6150
             TACCGTAGGCGCTGGACGCGCCGTATCCCGTCGCTTATAGGCCACTGCCC

I   A   D   A   V   Q   A   A   Y   P   L   S   Y   G   T   V   P

GTGGAACAGCCCTGCCCCCAGCCCAACCGGCACCGCCCCCTGCGCGTGGT
     6151    --------------------------------------------------    6200
             CACCTTGTCGGGACGGGGGTCGGGTTGGCCGTGGCGGGGGACGCGCACCA

H   F   L   G   A   G   L   G   V   P   V   A   G   Q   A   H

CGCGCCAGAAGCCTATGGCGTCATGGGCCAGCGCGATGGGCAGGATGCCC
     6201    --------------------------------------------------    6250
             GCGCGGTCTTCGGATACCGCAGTACCCGGTCGCGCTACCCGTCCTACGGG

D   R   W   F   G   I   A   D   H   A   L   A   I   P   L   I   G

CTTTCGCGCCGCATCTCCTGCCCGGTCCAGCCCCGCCTGGCGGCATAGTC
     6251    --------------------------------------------------    6300
             GAAAGCGCGGCGTAGAGGACGGGCCAGGTCGGGGCGGACCGCCGTATCAG

```
                CAGCGACGCCTGCGCCAGCGCGCCATCGTCCAGATCGCCGCCGTCGCTGT
6301            --------------------------------------------------  6350
                GTCGCTGCGGACGCGGTCGCGCGGTAGCAGGTCTAGCGGCGGCAGCGACA

L    S    A    Q    A    L    A    G    D    D    L    D    G    G    D    S

AGCGCGTATCCTCGATCAGGATGCGGGTGGGACTGAAGGGCAGCAGATAG
6351            --------------------------------------------------  6400
                TCGCGCATAGGAGCTAGTCCTACGCCCACCCTGACTTCCCGTCGTCTATC

Y    R    T    D    E    I    L    I    R    T    P    S    F    P    L    L    Y

ATGAAGCGGTACCCGTCCATCTGCGGAACGGTCGCGTCCATGATCATCGG
6401            --------------------------------------------------  6450
                TACTTCGCCATGGGCAGGTAGACGCCTTGCCAGCGCAGGTACTAGTAGCC

I    F    R    Y    G    D    M    Q    P    V    T    A    D    M    I    M    P

GCGCTCGACGCCATGGGGGGCGTCGGTCTCGATCTCGACGCCCACGAATT
6451            --------------------------------------------------  6500
                CGCGAGCTGCGGTACCCCCCGCAGCCAGAGCTAGAGCTGCGGGTGCTTAA

R    E    V    G    H    P    A    D    T    E    I    E    V    G    V    F

TCTGGAAACCCACGGTCAGGTGCGGGGTCTCGACGGCACCACGGGCGTCG
6501            --------------------------------------------------  6550
                AGACCTTTGGGTGCCAGTCCACGCCCCAGAGCTGCCGTGGTGCCCGCAGC

K    Q    F    G    V    T    L    H    P    T    E    V    A    G    R    A    D

ATCACGCAGGCAGCCTCGATCCGCGAGCCGTCCGTCAGCGTCGCGCCGGT
6551            --------------------------------------------------  6600
                TAGTGCGTCCGTCGGAGCTAGGCGCTCGGCAGGCAGTCGCAGCGCGGCCA

```
      ATCGTCCAGCGTCGCGACATGCGTATTCCACCGCAGATCGACACCCTGCA
6601  -------------------------------------------------- 6650
      TAGCAGGTCGCAGCGCTGTACGCATAAGGTGGCGTCTAGCTGTGGGACGT

D    D   L   T   A   V   H   T   N   W   R   L   D   V   G   Q

GCAGCCCGATCAGCGCGCCCGCCTCGATCGAGCCATAGCCTGTCGTCAGG
6651  -------------------------------------------------- 6700
      CGTCGGGCTAGTCGCGCGGGCGGAGCTAGCTCGGTATCGGACAGCAGTCC

L    L   G   I   L   A   G   A   E   I   S   G   Y   G   T   T   L

CGGCGCGAATGGTCGGGAAACGCGACCTCCTGATCCGTCCATTCGCCGCG
6701  -------------------------------------------------- 6750
      GCCGCGCTTACCAGCCCTTTGCGCTGGAGGACTAGGCAGGTAAGCGGCGC

R    R   S   H   D   P   F   A   V   E   Q   D   T   W   E   G   R

ACGAATGGGCGACAGGCGCGCCAGCCATTCGGGCGAAAGATCCGTGTCGT
6751  -------------------------------------------------- 6800
      TGCTTACCCGCTGTCCGCGCGGTCGGTAAGCCCGCTTTCTAGGCACAGCA

R    I   P   S   L   R   A   L   W   E   P   S   L   D   T   D

GGCAGGACCAGGTGTGCTGGTCCGAGGGGCCGGACCGCGCGTCGAGCATC
6801  -------------------------------------------------- 6850
      CCGTCCTGGTCCACACGACCAGGCTCCCCGGCCTGGCGCGCAGCTCGTAG

H    C   S   W   T   H   Q   D   S   P   G   S   R   A   D   L   M

ACGATGCGCGCATCCGGTCTGCGGTCGCGAACGGCAAGCGCGATCAGCGC
6851  -------------------------------------------------- 6900
      TGCTACGCGCGTAGGCCAGACGCCAGCGCTTGCCGTTCGCGCTAGTCGCG

```
            ACCGGACAGCCCCGCGCCCGCGATCAGCAGATCATGGCTCATGTATTGCG
  6901      --------------------------------------------------  6950
            TGGCCTGTCGGGGCGCGGGCGCTAGTCGTCTAGTACCGAGTACATAACGC

*   T   N   R

G   S   L   G   A   G   A   I   L   L   D   H   S   M
                                                    ←——CrtY

ATCCGCCCCTTCGCGGTCCTTCAGCAGCGCGCCCGAGCGTTTCAGCTCTG
  6951      --------------------------------------------------  7000
            TAGGCGGGGAAGCGCCAGGAAGTCGTCGCGCGGGCTCGCAAAGTCGAGAC

D   A   G   E   R   D   K   L   L   A   G   S   R   K   L   E

CCTTGAGGCTGTCGACCGAGGGCGCCCAGATGAAACCGAAGCTGACGCAG
  7001      --------------------------------------------------  7050
            GGAACTCCGACAGCTGGCTCCCGCGGGTCTACTTTGGCTTCGACTGCGTC

A   K   L   S   D   V   S   P   A   W   I   F   G   F   S   V   C

TTCTCGCGGCCATGGACCGCGTGATGCATCCTGTGTGCCTGGTAGACGCG
  7051      --------------------------------------------------  7100
            AAGAGCGCCGGTACCTGGCGCACTACGTAGGACACACGGACCATCTGCGC

N   E   R   G   H   V   A   H   H   M   R   H   A   Q   Y   V   R

ACGAAGATAGCCGCGCTTGGGGACATAGCGGAACGGCCAGCGCCCATGCA
  7101      --------------------------------------------------  7150
            TGCTTCTATCGGCGCGAACCCCTGTATCGCCTTGCCGGTCGCGGGTACGT

R   L   Y   G   R   K   P   V   Y   R   F   P   W   R   G   H

CCAAGCCGTCATGCAGGAAATAGTAGATCAGCCCGTAGCAGGTGACCCCC
  7151      --------------------------------------------------  7200
            GGTTCGGCAGTACGTCCTTTATCATCTAGTCGGGCATCGTCCACTGGGGG
             V   L   G   D   H   L   F   Y   Y   I   L   G   Y   C   T   V   G
```

*FIG. 7X*

```
           ACCGCCAGCCACCAGGCCAGATCCGACCCCATCGCGCCGATCGCGAACAG
     7201  --------------------------------------------------  7250
           TGGCGGTCGGTGGTCCGGTCTAGGCTGGGGTAGCGCGGCTAGCGCTTGTC

V   A   L   W   W   A   L   D   S   G   M   A   G   I   A   F   L

CACGATCGAGATTACCGCGAAGATGACGCCATAGAGGTCGTTCTTCTCGA
     7251  --------------------------------------------------  7300
           GTGCTAGCTCTAATGGCGCTTCTACTGCGGTATCTCCAGCAAGAAGAGCT

V   I   S   I   V   A   F   I   V   G   Y   L   D   N   K   E

GCGCGTGGTCGTGATCCTCGTCGTGGTGCGATTTATGCCAGCCCCAGCCC
     7301  --------------------------------------------------  7350
           CGCGCACCAGCACTAGGAGCAGCACCACGCTAAATACGGTCGGGGTCGGG

L   A   H   D   H   D   E   D   H   H   S   K   H   W   G   W   G

AGGGGGCCATGCATGATCCACCGATGGACGGAGTAGGCCGTCAGCTCCAT
     7351  --------------------------------------------------  7400
           TCCCCCGGTACGTACTAGGTGGCTACCTGCCTCATCCGGCAGTCGAGGTA

L   P   G   H   M   I   W   R   H   V   S   Y   A   T   L   E   M

CGCGGCGACGGTCAGGATGACGGTCAGGATTGCGGCCCAAGTGCTCATGC
     7401  --------------------------------------------------  7450
           GCGCCGCTGCCAGTCCTACTGCCAGTCCTAACGCCGGGTTCACGAGTACG

A   A   V   T   L   I   V   T   L   I   A   A   W   T   S   M
                                                                ←  ─  CrtZ

CGGCCCCTTGCTTGATATGACAGGGAACAGGCTACGCTGCCGCGCGGTGC
     7451  --------------------------------------------------  7500
           GCCGGGGAACGAACTATACTGTCCCTTGTCCGATGCGACGGCGCGCCACG
```

*FIG. 7Y*

```
       ATGACCAGCCCATCGGGGTGCGACCAAAGGGCATCGCGTGACATCTGCGT
7501   -------------------------------------------------- 7550
       TACTGGTCGGGTAGCCCCACGCTGGTTTCCCGTAGCGCACTGTAGACGCA

TCAGGGCTCATAGGCGGATCATCCGTGACATTCGCCGCCGAACGCGGCAG
7551   -------------------------------------------------- 7600
       AGTCCCGAGTATCCGCCTAGTAGGCACTGTAAGCGGCGGCTTGCGCCGTC

GCGCATCACGCGTTCCGTCGCTGGAAATATTAATGTTTTCCCGAAGATGG
7601   -------------------------------------------------- 7650
       CGCGTAGTGCGCAAGGCAGCGACCTTTATAATTACAAAAGGGCTTCTACC

TCGGGGCGAGAGGATTCGAACCTCCGACCTACGGTACCCAAAACCGTCGC
7651   -------------------------------------------------- 7700
       AGCCCCGCTCTCCTAAGCTTGGAGGCTGGATGCCATGGGTTTTGGCAGCG

GCTACCAGGCTGCGCTACGCCCCGACTGCGGAAGGCTTTAGCCGATTGTT
7701   -------------------------------------------------- 7750
       CGATGGTCCGACGCGATGCGGGGCTGACGCCTTCCGAAATCGGCTAACAA

CCGGCAAGGGAAAGACCTAGTCGCAGGCCAGGACCGCATTGTCGCCCATG
7751   -------------------------------------------------- 7800
       GGCCGTTCCCTTTCTGGATCAGCGTCCGGTCCTGGCGTAACAGCGGGTAC

```
       CCCGGATGCGCCATCGGCTGACCGGGCTTCAGGCCAAGGCGATCCGCCTC
7801   -------------------------------------------------- 7850
       GGGCCTACGCGGTAGCCGACTGGCCCGAAGTCCGGTTCCGCTAGGCGGAG

G   P   H   A   M   P   Q   G   P   K   L   G   L   R   D   A   E

TCCGCCCGCGATTTCGAGGACGAACAGCCGGTCGGGGTCCGGATCGCCGA
7851   -------------------------------------------------- 7900
       AGGCGGGCGCTAAAGCTCCTGCTTGTCGGCCAGCCCCAGGCCTAGCGGCT

G   G   A   I   E   L   V   F   L   R   D   P   D   P   D   G

CCGCCGCGCCCGGAATGGGCGTCTCGTCCAGCGGGCGCGCATTGCGGTGG
7901   -------------------------------------------------- 7950
       GGCGGCGCGGGCCTTACCCGCAGAGCAGGTCGCCCGCGCGTAACGCCACC

V   A   A   G   P   I   P   T   E   D   L   P   R   A   N   R   H

ATGTGGCGGATGACGCCGGTTTCATCCGCAAAGACCATGTCCAGCGGGAT
7951   -------------------------------------------------- 8000
       TACACCGCCTACTGCGGCCAAAGTAGGCGTTTCTGGTACAGGTCGCCCTA

I   H   R   I   V   G   T   E   D   A   F   V   M   D   L   P   I

CAGTGTGTTGCGCATCCAGAAGGACACCGGCTGGGGCGATTCGTAGATGA
8001   -------------------------------------------------- 8050
       GTCACACAACGCGTAGGTCTTCCTGTGGCCGACCCCGCTAAGCATCTACT

L   T   N   R   M   W   F   S   V   P   Q   P   S   E   Y   I

ACAGCATTCCGGTGCCCGCAGGCAGCTCCTTGCGGAACATCAGGCCCTGC
8051   -------------------------------------------------- 8100
       TGTCGTAAGGCCACGGGCGTCCGTCGAGGAACGCCTTGTAGTCCGGGACG
```

*FIG. 7A1*

```
        GCGCGCTCTTCGGGGCTGTCCGCGACCTCGACCCGAAACCCGAGCGTTTC
8101    --------------------------------------------------  8150
        CGCGCGAGAAGCCCCGACAGGCGCTGGAGCTGGGCTTTGGGCTCGCAAAG

A   R   E   E   P   S   D   A   V   E   V   R   F   G   L   T   E

CGCACCGGTATCGACGACAAGACTGCCGGGCGCGCATTCCACCGCCGCCG
8151    --------------------------------------------------  8200
        GCGTGGCCATAGCTGCTGTTCTGACGGCCCGCGCGTAAGGTGGCGGCGGC

A   G   T   D   V   V   L   S   G   P   A   C   E   V   A   A

CGGCGGCGGGCATCAGGACCGCAAGAAGCGCTGCGGCCTTACTCGGCCAC
8201    --------------------------------------------------  8250
        GCCGCCGCCCGTAGTCCTGGCGTTCTTCGCGACGCCGGAATGAGCCGGTG

A   A   A   P   M   L   V   A   L   L   A   A   A   K   S   P   W

ATGGGCAAGATAGGACTGCTCGGCGCCGAGATCCTGCTGACCCTGCGCAT
8251    --------------------------------------------------  8300
        TACCCGTTCTATCCTGACGAGCCGCGGCTCTAGGACGACTGGGACGCGTA

M   P   L   I   P   S   S   P   A   S   I   R   S   V   R   R   M

CCTCGTTCCGGTCATGCAGCGCCAGGTCCCATGCCGCGATCTGCGCGnnC
8301    --------------------------------------------------  8350
        GGAGCAAGGCCAGTACGTCGCGGTCCAGGGTACGGCGCTAGACGCGCnnG

R   T   G   T   M  ←  — orf-16

ATCAGCCCGCGCGGACCCTCGACGACGCGGAGGCAGATCGCCTCGCCGAT
8351    --------------------------------------------------  8400
        TAGTCGGGCGCGCCTGGGAGCTGCTGCGCCTCCGTCTAGCGGAGCGGCTA

```
        CACGAGGTCCGAGAAGCCGGAATGACGGAGCACCTCGATATGGATGAACA
8401    -------------------------------------------------- 8450
        GTGCTCCAGGCTCTTCGGCCTTACTGCCTCGTGGAGCTATACCTACTTGT

CGTCCTCGGGGTGGCCGAAGATGTTGGCGAACCGGGAAAAGGCCCTTGGC
8451    -------------------------------------------------- 8500
        GCAGGAGCCCCACCGGCTTCTACAACCGCTTGGCCCTTTTCCGGGAACCG

CTTGTCGAACCACTTGACGCGGGCCGGACGCAGCGGCAnnCGTCCAGATG
8501    -------------------------------------------------- 8550
        GAACAGCTTGGTGAACTGCGCCCGGCCTGCGTCGCCGTnnGCAGGTCTAC

CTCGATCACCTCGGCATCCAGATCGGCGATnGGGGGGTGnCnGTCGCTTT
8551    -------------------------------------------------- 8600
        GAGCTAGTGGAGCCGTAGGTCTAGCCGCTAnCCCCCACnGnCAGCGAAA

CnnnCGGTTCGATCGACAGGACCTC
8601    ------------------------- 8625
        GnnnGCCAAGCTAGCTGTCCTGGAG
```

*FIG. 7C1*

```
  1  MTPKQQFPLR DLVEIRLAQI SGQFGVVSAP LGAAMSDAAL SPGKRFRAVL

51  MLMVAESSGG VCDAMVDAAC AVEMVHAASL IFDDMPCMDD ARTRRGQPAT

101  HVAHGEGRAV LAGIALITEA MRILGEARGA TPDQRARLVA SMSRAMGPVG

151  LCAGQDLDLH APKDAAGIER EQDLKTGVLF VAGLEMLSII KGLDKAETEQ

201  LMAFGRQLGR VFQSYDDLLD VIGDKASTGK DTARDTAAPG PKGGLMAVGQ

251  MGDVAQHYRA SRAQLDELMR TRLFRGGQIA DLLARVLPHD IRRSA
```

FIG. 8

```
  1  MTDLTATSEA  AIAQGSQSFA  QAAKLMPPGI  REDTVMLYAW  CRHADDVIDG

51  QVMGSAPEAG  GDPQARLGAL  RADTLAALHE  DGPMSPPFAA  LRQVARRHDF

101  PDLWPMDLIE  GFAMDVADRE  YRSLDDVLEY  SYHVAGVVGV  MMARVMGVQD

151  DAVLDRACDL  GLAFQLTNIA  RDVIDDAAIG  RCYLPADWLA  EAGATVEGPV

201  PSDALYSVII  RLLDAAEPYY  ASARQGLPHL  PPRCAWSIAA  ALRIYRAIGT

251  RIRQGGPEAY  RQRISTSKAA  KIGLLARGGL  DAAASRLRGG  EISRDGLWTR

301  PRA
```

*FIG. 9*

1 MSSAIVIGAG FGGLALAIRL QSAGIATTIV EARDKPGGRA YVWNDQGHVF

51 DAGPTVVTDP DSLRELWALS GQPMERDVTL LPVSPFYRLT WADGRSFEYV

101 NDDDELIRQV ASFNPADVDG YRRFHDYAEE VYREGYLKLG TTPFLKLGQM

151 LNAAPALMRL QAYRSVHSMV ARFIQDPHLR QAFSFHTLLV GGNPFSTSSI

201 YALIHALERR GGVWFAKGGT NQLVAGMVAL FERLGGTLLL NARVTRIDTE

251 GDRATGVTLL DGRQLRADTV ASNGDVMHSY RDLLGHTRRG RTKAAILNRQ

301 RWSMSLFVLH FGLSKRPENL AHHSVIFGPR YKGLVNEIFN GPRLPDDFSM

351 YLHSPCVTDP SLAPEGMSTH YVLAPVPHLG RADVDWEAEA PGYAERIFEE

401 LERRAIPDLR KHLTVSRIFS PADFSTELSA HHGSAFSVEP ILTQSAWFRP

451 HNRDRAIPNF YIVGAGTHPG AGIPGVVGSA KATAQVMLSD LAVA

FIG. 10

1 MSHDLLIAGA GLSGALIALA VRDRRPDARI VMLDARSGPS DQHTWSCHDT

51 DLSPEWLARL SPIRRGEWTD QEVAFPDHSR RLTTGYGSIE AGALIGLLQG

101 VDLRWNTHVA TLDDTGATLT DGSRIEAACV IDARGAVETP HLTVGFQKFV

151 GVEIETDAPH GVERPMIMDA TVPQMDGYRF IYLLPFSPTR ILIEDTRYSD

201 GGDLDDGALA QASLDYAARR GWTGQEMRRE RGILPIALAH DAIGFWRDHA

251 QGAVPVGLGA GLFHPVTGYS LPYAAQVADA IAARDLTTAS ARRAVRGWAI

301 DRADRDRFLR LLNRMLFRGC PPDRRYRLLQ RFYRLPQPLI ERFYAGRLTL

351 ADRLRIVTGR PPIPLSQAVR CLPERPLLQE RA

FIG. 11

```
  1 MSTWAAILTV ILTVAAMELT AYSVHRWIMH GPLGWGWHKS HHDEDHDHAL

51 EKNDLYGVIF AVISIVLFAI GAMGSDLAWW LAVGVTCYGL IYYFLHDGLV

101 HGRWPFRYVP KRGYLRRVYQ AHRMHHAVHG RENCVSFGFI WAPSVDSLKA

151 ELKRSGALLK DREGADRNT
```

FIG. 12

```
                                    ┌─► CrtE
#100:  5' tatatactagtaagaggagaaattacatATGACGCCCAAGCAGCAGCAATC  3'

#101:  5' TATATACCCGGGTCAGCCGCGACGGCCTGTGG  3'
              SmaI

┌─►CrtZ
#104:  5' tatatgaattcaagaggagaaattacatATGAGCACTTGGGCCGCAATCC 3'
             EcoRI   RBS          NdeI

105:  5' GTTTCAGCTCTGCCTTGAGGC  3' crtZ ──────►                    ┌─►CrtY
MUT1:  5' GCGAAGGGGCGGATCGCAATACgTGaaaggaggacacotgATGAGCCATGATCTGCTGATCG 3'
                                            PmlI crtY─►
MUT2:  5' GCCCCCTGCTGCAGGAGAGAGCtTGaaaggaggcaattgagATGAGTTCCGCCATCGTCATCG 3'
                                        MunI CrtI ──►                         ┌─►CrtB
MUT3:  5' GGTCATGCTGTCGGACCTGGCCGTCGCtTGaaaggaggatgcaatcATGACCGATCTGACGGCGACTTCC 3'
                                          BamHI
MUT5:  5' ATATATctcaattgcctcctttcaagGCTCTCTCCTGCAGCAGGG  3'
                MunI         └───crtY MUT6:  5' atgattggatcctcctttcaaGCGACGGCCAGGTCCGACAGC  3'
              BamHI      └───crtY

CAR17  5' CAGAACCCATCACCTGCCCGTC    3'

Cat3:  5' CGCGAATTCTCGCCGGCAATAGTTACC  3'
              EcoRI

Cat4:  5' GTCACATGCATGCATGTTACGAGCTCATAAGCATGTGACGTCTTCAACTAACGGGGCAGG 3'
                    SphI      SacI          AatII
```

FIG. 14

```
                    HindIII   AflII    XbaI          EcoRI
CS1: 5'  AGCTTGGATCCTTAAGTACTCTAGAGTTTAAACG        3'
CS2: 3'          ACCTAGGAATTCATGAGATCTCAAATTTGCTTAA 5'

SalI  AvrII      MluI      BamHI       HindIII
MUT7: 5' TCGACCCTAGGCACGTGACGCGTCAATTGGATCCGCATGCAAGCTT 3'
MUT8: 3'     GGGATCCGTGCACTGCGCAGTTAACCTAGGCGTACGTTCGAACTAG 5'
                        PmlI     MunI     SphI 1/2 PmlI
MUT9:  5' gtgtcctcctttcacGTATTGCGATCCGCCCCTTCGCGGTCCTTCAGCAGGCGCCGAGCGTTTCAGCTCTGCCTTGAGGCTG
MUT10: 3' cacaggaggaaagtgCATAACGCTAGGCGGGGAAGCGCCAGGAAGTCGTCCGCGGCTCGCAAAGTCGAGACGGAACTCCGACAGCT  5'
                       RBS    ├── crtZ SalI SpeI
MUT11: 5' TAAGAAACcctccttttA        3'
MUT12: 3' TCTTTCggaggaaaTGATC 5'
                 RBS
```

```
     CTAAATTGTAAGCGTTAATATTTTGTTAAAATTCGCGTTAAATTTTTGTTAAATCAGCTC
  1  ------------------------------------------------------------
 60
     GATTTAACATTCGCAATTATAAAACAATTTTAAGCGCAATTTAAAAACAATTTAGTCGAG

ATTTTTTAACCAATAGGCCGAAATCGGCAAAATCCCTTATAAATCAAAAGAATAGACCGA
 61  ------------------------------------------------------------
120
     TAAAAAATTGGTTATCCGGCTTTAGCCGTTTTAGGGAATATTTAGTTTTCTTATCTGGCT

GATAGGGTTGAGTGTTGTTCCAGTTTGGAACAAGAGTCCACTATTAAAGAACGTGGACTC
121  ------------------------------------------------------------
180
     CTATCCCAACTCACAACAAGGTCAAACCTTGTTCTCAGGTGATAATTTCTTGCACCTGAG

CAACGTCAAAGGGCGAAAAACCGTCTATCAGGGCGATGGCCCACTACGTGAACCATCACC
181  ------------------------------------------------------------
240
     GTTGCAGTTTCCCGCTTTTTGGCAGATAGTCCCGCTACCGGGTGATGCACTTGGTAGTGG

CTAATCAAGTTTTTTGGGGTCGAGGTGCCGTAAAGCACTAAATCGGAACCCTAAAGGGAG
241  ------------------------------------------------------------
300
     GATTAGTTCAAAAAACCCCAGCTCCACGGCATTTCGTGATTTAGCCTTGGGATTTCCCTC

CCCCCGATTTAGAGCTTGACGGGGAAAGCCGGCGAACGTGGCGAGAAAGGAAGGGAAGAA
301  ------------------------------------------------------------
360
     GGGGGCTAAATCTCGAACTGCCCCTTTCGGCCGCTTGCACCGCTCTTTCCTTCCCTTCTT

AGCGAAAGGAGCGGGCGCTAGGGCGCTGGCAAGTGTAGCGGTCACGCTGCGCGTAACCAC
361  ------------------------------------------------------------
420
     TCGCTTTCCTCGCCCGCGATCCCGCGACCGTTCACATCGCCAGTGCGACGCGCATTGGTG

CACACCCGCCGCGCTTAATGCGCCGCTACAGGGCGCGTCCCATTCGCCATTCAGGCTGCG
421  ------------------------------------------------------------
480
     GTGTGGGCGGCGCGAATTACGCGGCGATGTCCCGCGCAGGGTAAGCGGTAAGTCCGACGC

CAACTGTTGGGAAGGGCGATCGGTGCGGGCCTCTTCGCTATTACGCCAGCTGGCGAAAGG
481  ------------------------------------------------------------
540
     GTTGACAACCCTTCCCGCTAGCCACGCCCGGAGAAGCGATAATGCGGTCGACCGCTTTCC

GGGATGTGCTGCAAGGCGATTAAGTTGGGTAACGCCAGGGTTTTCCCAGTCACGACGTTG
541  ------------------------------------------------------------
600
     CCCTACACGACGTTCCGCTAATTCAACCCATTGCGGTCCCAAAAGGGTCAGTGCTGCAAC

TAAAACGACGGCCAGTGAGCGCGCGTAATACGACTCACTATAGGGCGAATTGGAGCTCCA
```

```
601 ------------------------------------------------------------
660     ATTTTGCTGCCGGTCACTCGCGCGCATTATGCTGAGTGATATCCCGCTTAACCTCGAGGT

CCGCGGTGGCGGCCCCTCTAGTGGATCCGCGCCTGGCCGTTCGCGATCAGCAGCCGCCCT
661 ------------------------------------------------------------
720     GGCGCCACCGCCGGCGAGATCACCTAGGCGCGGACCGGCAAGCGCTAGTCGTCGGCGGGA

TGCGGATCGGTCAGCATCATCCCCATGAACCGCAGCGCACGACGCAGCGCGCCCCAGA
721 ------------------------------------------------------------
780     ACGCCTAGCCAGTCGTAGTAGGGGTACTTGGCGTCGCGTGCTGCGTCGCGCGCGGGGTCT

TCGGGCGCGTCCAGCACGGCATGCGCCATCATCGCGAAGGCCCCCGGCGGCATGGGGCGC
781 ------------------------------------------------------------
840     AGCCCGCGCAGGTCGTGCCGTACGCGGTAGTAGCGCTTCCGGGGGCCGCCGTACCCCGCG

GTGCCCATTCCGAAGAACTCGCAGCCTGTCCGCTGCGCAAGGTCGCGCCAGATCGCGCCG
841 ------------------------------------------------------------
900     CACGGGTAAGGCTTCTTGAGCGTCGGACAGGCGACGCGTTCCAGCGCGGTCTAGCGCGGC

TATTCCGATGCAGTGACGGGCCCGATGCGCGTGGGCCCGCCCTGCCCCGCCGCCACCAGC
901 ------------------------------------------------------------
960     ATAAGGCTACGTCACTGCCCGGGCTACGCGCACCCGGGCGGGACGGGGCGGCGGTGGTCG
```

```
     CTAAATTGTAAGCGTTAATATTTTGTTAAAATTCGCGTTAAATTTTTGTTAAATCAGCTC
  1  ------------------------------------------------------------  60
     GATTTAACATTCGCAATTATAAAACAATTTTAAGCGCAATTTAAAAACAATTTAGTCGAG

ATTTTTTAACCAATAGGCCGAAATCGGCAAAATCCCTTATAAATCAAAAGAATAGACCGA
 61  ------------------------------------------------------------ 120
     TAAAAAATTGGTTATCCGGCTTTAGCCGTTTTAGGGAATATTTAGTTTTCTTATCTGGCT

GATAGGGTTGAGTGTTGTTCCAGTTTGGAACAAGAGTCCACTATTAAAGAACGTGGACTC
121  ------------------------------------------------------------ 180
     CTATCCCAACTCACAACAAGGTCAAACCTTGTTCTCAGGTGATAATTTCTTGCACCTGAG

CAACGTCAAAGGGCGAAAAACCGTCTATCAGGGCGATGGCCCACTACGTGAACCATCACC
181  ------------------------------------------------------------ 240
     GTTGCAGTTTCCCGCTTTTTGGCAGATAGTCCCGCTACCGGGTGATGCACTTGGTAGTGG

CTAATCAAGTTTTTTGGGGTCGAGGTGCCGTAAAGCACTAAATCGGAACCCTAAAGGGAG
241  ------------------------------------------------------------ 300
     GATTAGTTCAAAAAACCCCAGCTCCACGGCATTTCGTGATTTAGCCTTGGGATTTCCCTC

CCCCCGATTTAGAGCTTGACGGGGAAAGCCGGCGAACGTGGCGAGAAAGGAAGGGAAGAA
301  ------------------------------------------------------------ 360
     GGGGGCTAAATCTCGAACTGCCCCTTTCGGCCGCTTGCACCGCTCTTTCCTTCCCTTCTT

AGCGAAAGGAGCGGGCGCTAGGGCGCTGGCAAGTGTAGCGGTCACGCTGCGCGTAACCAC
361  ------------------------------------------------------------ 420
     TCGCTTTCCTCGCCCGCGATCCCGCGACCGTTCACATCGCCAGTGCGACGCGCATTGGTG

CACACCCGCCGCGCTTAATGCGCCGCTACAGGGCGCGTCCCATTCGCCATTCAGGCTGCG
421  ------------------------------------------------------------ 480
     GTGTGGGCGGCGCGAATTACGCGGCGATGTCCCGCGCAGGGTAAGCGGTAAGTCCGACGC

CAACTGTTGGGAAGGGCGATCGGTGCGGGCCTCTTCGCTATTACGCCAGCTGGCGAAAGG
481  ------------------------------------------------------------ 540
     GTTGACAACCCTTCCCGCTAGCCACGCCCGGAGAAGCGATAATGCGGTCGACCGCTTTCC

GGGATGTGCTGCAAGGCGATTAAGTTGGGTAACGCCAGGGTTTTCCCAGTCACGACGTTG
541  ------------------------------------------------------------ 600
     CCCTACACGACGTTCCGCTAATTCAACCCATTGCGGTCCCAAAAGGGTCAGTGCTGCAAC

TAAAACGACGGCCAGTGAGCGCGCGTAATACGACTCACTATAGGGCGAATTGGAGCTCCA
601  ------------------------------------------------------------ 660
     ATTTTGCTGCCGGTCACTCGCGCGCATTATGCTGAGTGATATCCCGCTTAACCTCGAGGT

CCGCGGTGGCGGCCCCTCTAGTGGATCCGCGCCTGGCCGTTCGCGATCAGCAGCCGCCCT
661  ------------------------------------------------------------ 720
     GGCGCCACCGCCGGCGAGATCACCTAGGCGCGGACCGGCAAGCGCTAGTCGTCGGCGGGA

TGCGGATCGGTCAGCATCATCCCCATGAACCGCAGCGCACGACGCAGCGCGCGCCCCAGA
721  ------------------------------------------------------------ 780
     ACGCCTAGCCAGTCGTAGTAGGGGTACTTGGCGTCGCGTGCTGCGTCGCGCGCGGGGTCT
```

```
        TCGGGCGCGTCCAGCACGGCATGCGCCATCATCGCGAAGGCCCCCGGCGGCATGGGGCGC
781     ------------------------------------------------------------ 840
        AGCCCGCGCAGGTCGTGCCGTACGCGGTAGTAGCGCTTCCGGGGGCCGCCGTACCCCGCG

GTGCCCATTCCGAAGAACTCGCAGCCTGTCCGCTGCGCAAGGTCGCGCCAGATCGCGCCG
841     ------------------------------------------------------------ 900
        CACGGGTAAGGCTTCTTGAGCGTCGGACAGGCGACGCGTTCCAGCGCGGTCTAGCGCGGC

TATTCCGATGCAGTGACGGGCCCGATGCGCGTGGGCCCGCCCTGCCCCGCCGCCACCAGC
901     ------------------------------------------------------------ 960
        ATAAGGCTACGTCACTGCCCGGGCTACGCGCACCCGGGCGGGACGGGGCGGCGGTGGTCG
```

```
      GCATCGCGCACGAACCCTTCCGAGATGATGTCTGATCCATGGCCCGTCATTGCAAAACC
 961  ------------------------------------------------------------ 1020
      CGTAGCGCGTGCTTGGGAAGGCTCTACTACACGACTAGGTACCGGGCAGTAACGTTTTGG

GATCACCGATCCTGTCGCGTGATGGCATTGTTTGCAATGCCCCGAGGGCTAGGATGGCGC
1021  ------------------------------------------------------------ 1080
      CTAGTGGCTAGGACAGCGCACTACCGTAACAAACGTTACGGGGCTCCCGATCCTACCGCG

GAAGGATCAAGGGGGGAGAGACATGGAAATCGAGGGACGGGTCTTTGTCGTCACGGGCG
1081  ------------------------------------------------------------ 1140
      CTTCCTAGTTCCCCCCCTCTCTGTACCTTTAGCTCCCTGCCCAGAAACAGCAGTGCCCGC

CCGCATCGGGTCTGGGGGCGGCCTCGGCGCGGATGCTGGCCCAAGGCGGCGCGAAGGTCG
1141  ------------------------------------------------------------ 1200
      GGCGTAGCCCAGACCCCCGCCGGAGCCGCGCCTACGACCGGGTTCCGCCGCGCTTCCAGC

TGCTGGCCGATCTGGCGGAACCGAAGGACGCGCCCGAAGGCGCGGTTCACGCGGCCTGCG
1201  ------------------------------------------------------------ 1260
      ACGACCGGCTAGACCGCCTTGGCTTCCTGCGCGGGCTTCCGCGCCAAGTGCGCCGGACGC

ACGTGACCGACGCGACCGCTGCGCAGACGGCCATCGCGCTGGCGACCGACCGCTTCGGCA
1261  ------------------------------------------------------------ 1320
      TGCACTGGCTGCGCTGGCGACGCGTCTGCCGGTAGCGCGACCGCTGGCTGGCGAAGCCGT

GGCTGGACGGCCTTGTGAACTGCGCGGGCATCGCGCCGGCCGAACGGATGCTGGGCCGCG
1321  ------------------------------------------------------------ 1380
      CCGACCTGCCGGAACACTTGACGCGCCCGTAGCGCGGCCGGCTTGCCTACGACCCGGCGC

ACGGGCCGCATGGACTGGACAGCTTTGCCCGTGCGGTCACGATCAACCTGATCGGCAGCT
1381  ------------------------------------------------------------ 1440
      TGCCCGGCGTACCTGACCTGTCGAAACGGGCACGCCAGTGCTAGTTGGACTAGCCGTCGA

TCAACATGGCCCGCCTTGCAGCCGAGGCGATGGCCCGGAACGAGCCCGTCCGGGGCGAGC
1441  ------------------------------------------------------------ 1500
      AGTTGTACCGGGCGGAACGTCGGCTCCGCTACCGGGCCTTGCTCGGGCAGGCCCCGCTCG

GTGGCGTGATCGTCAACACGGCCTCGATCGCGGCGCAGGACGGACAGATCGGACAGGTCG
1501  ------------------------------------------------------------ 1560
      CACCGCACTAGCAGTTGTGCCGGAGCTAGCGCCGCGTCCTGCCTGTCTAGCCTGTCCAGC

CCTATGCGGCCAGCAAGGCGGGCGTGGCGGGCATGACGCTGCCGATGGCCCGCGACCTTG
1561  ------------------------------------------------------------ 1620
      GGATACGCCGGTCGTTCCGCCCGCACCGCCCGTACTGCGACGGCTACCGGGCGCTGGAAC

CGCGGCACGGCATCCGCGTCATGACCATCGCGCCCGGCATCTTCCGCACCCCGATGCTGG
1621  ------------------------------------------------------------ 1680
      GCGCCGTGCCGTAGGCGCAGTACTGGTAGCGCGGGCCGTAGAAGGCGTGGGGCTACGACC

AGGGGCTGCCGCAGGACGTTCAGGACAGCCTGGGCGCGGCGGTGCCCTTCCCCTCGCGGC
1681  ------------------------------------------------------------ 1740
      TCCCCGACGGCGTCCTGCAAGTCCTGTCGGACCCGCGCCGCCACGGGAAGGGGAGCGCCG
```

```
        TGGGAGAGCCGTCGGAATACGCGGCGCTGTTGCACCACATCATCGCGAACCCCATGCTGA
1741    ------------------------------------------------------------  1800
        ACCCTCTCGGCAGCCTTATGCGCCGCGACAACGTGGTGTAGTAGCGCTTGGGGTACGACT

ACGGAGAGGTCATCCGCCTCGACGGCGCATTGCGCATGGCCCCCAAGTGAAGGAGCGTTT
1801    ------------------------------------------------------------  1860
        TGCCTCTCCAGTAGGCGGAGCTGCCGCGTAACGCGTACCGGGGGTTCACTTCCTCGCAAA

CATGGACCCCATCGTCATCACCGGCGCGATGCGCACCCCGATGGGGGCATTCCAGGGCGA
1861    ------------------------------------------------------------  1920
        GTACCTGGGGTAGCAGTAGTGGCCGCGCTACGCGTGGGGCTACCCCCGTAAGGTCCCGCT

TCTTGCCGCGATGGATGCCCCGACCCTTGGCGCGGACGCGATCCGCGCCGCGCTGAACGG
1921    ------------------------------------------------------------  1980
        AGAACGGCGCTACCTACGGGGCTGGGAACCGCGCCTGCGCTAGGCGCGGCGCGACTTGCC
```

```
      CCTGTCGCCCGACATGGTGGACGAGGTGCTGATGGGCTGCGTCCTCGCCGCGGGCCAGGG
1981  ------------------------------------------------------------ 2040
      GGACAGCGGGCTGTACCACCTGCTCCACGACTACCCGACGCAGGAGCGGCGCCCGGTCCC

TCAGGCACCGGCACGTCAGGCGGCGCTTGGCGCCGGACTGCCGCTGTCGACGGGCACGAC
2041  ------------------------------------------------------------ 2100
      AGTCCGTGGCCGTGCAGTCCGCCGCGAACCGCGGCCTGACGGCGACAGCTGCCCGTGCTG

CACCATCAACGAGATGTGCGGATCGGGCATGAAGGCCGCGATGCTGGGCCATGACCTGAT
2101  ------------------------------------------------------------ 2160
      GTGGTAGTTGCTCTACACGCCTAGCCCGTACTTCCGGCGCTACGACCCGGTACTGGACTA

CGCCGCGGGATCGGCGGGCATCGTCGTCGCCGGCGGGATGGAGAGCATGTCGAACGCCCC
2161  ------------------------------------------------------------ 2220
      GCGGCGCCCTAGCCGCCCGTAGCAGCAGCGGCCGCCCTACCTCTCGTACAGCTTGCGGGG

CTACCTGCTGCCCAAGGCGCGGTCGGGGATGCGCATGGGCCATGACCGTGTGCTGGATCA
2221  ------------------------------------------------------------ 2280
      GATGGACGACGGGTTCCGCGCCAGCCCCTACGCGTACCCGGTACTGGCACACGACCTAGT

CATGTTCCTCGACGGGTTGGAGGACGCCTATGACAAGGGCCGCCTGATGGGCACCTTCGC
2281  ------------------------------------------------------------ 2340
      GTACAAGGAGCTGCCCAACCTCCTGCGGATACTGTTCCCGGCGGACTACCCGTGGAAGCG

CGAGGATTGCGCCGGCGATCACGGTTTCACCCGCGAGGCGCAGGACGACTATGCGCTGAC
2341  ------------------------------------------------------------ 2400
      GCTCCTAACGCGGCCGCTAGTGCCAAAGTGGGCGCTCCGCGTCCTGCTGATACGCGACTG

CAGCCTGGCCCGCGCGCAGGACGCCATCGCCAGCGGTGCCTTCGCCGCCGAGATCGCGCC
2401  ------------------------------------------------------------ 2460
      GTCGGACCGGGCGCGCGTCCTGCGGTAGCGGTCGCCACGGAAGCGGCGGCTCTAGCGCGG

CGTGACCGTCACGGCACGCAAGGTGCAGACCACCGTCGATACCGACGAGATGCCCGGCAA
2461  ------------------------------------------------------------ 2529
      GCACTGGCAGTGCCGTGCGTTCCACGTCTGGTGGCAGCTATGGCTGCTCTACGGGCCGTT

GGCCCGCCCCGAGAAGATCCCCCATCTGAAGCCCGCCTTCCGTGACGGTGGCACGGTCAC
2521  ------------------------------------------------------------ 2580
      CCGGGCGGGGCTCTTCTAGGGGGTAGACTTCGGGCGGAAGGCACTGCCACCGTGCCAGTG

GGCGGCGAACAGCTCGTCGATCTCGGACGGGGCGGCGGCGCTGGTGATGATGCGCCAGTC
2581  ------------------------------------------------------------ 2640
      CCGCCGCTTGTCGAGCAGCTAGAGCCTGCCCCGCCGCCGCGACCACTACTACGCGGTCAG

GCAGGCCGAGAAGCTGGGCCTGACGCCGATCGCGCGGATCATCGGTCATGCGACCCATGC
2641  ------------------------------------------------------------ 2700
      CGTCCGGCTCTTCGACCCGGACTGCGGCTAGCGCGCCTAGTAGCCAGTACGCTGGGTACG

CGACCGTCCCGGCCTGTTCCCGACGGCCCCCATCGGCGCGATGCGCAAGCTGCTGGACCG
2701  ------------------------------------------------------------ 2760
      GCTGGCAGGGCCGGACAAGGGCTGCCGGGGGTAGCCGCGCTACGCGTTCGACGACCTGGC
```

```
        CACGGACACCCGCCTTGGCGATTACGACCTGTTCGAGGTGAACGAGGCATTCGCCGTCGT
2761    ------------------------------------------------------------ 2820
        GTGCCTGTGGGCGGAACCGCTAATGCTGGACAAGCTCCACTTGCTCCGTAAGCGGCAGCA

CGCCATGATCGCGATGAAGGAGCTTGGCCTGCCACACGATGCCACGAACATCAACGGCGG
2821    ------------------------------------------------------------ 2880
        GCGGTACTAGCGCTACTTCCTCGAACCGGACGGTGTGCTACGGTGCTTGTAGTTGCCGCC

GGCCTGCGCGCTTGGGCATCCCATCGGCGCGTCGGGGGCGCGGATCATGGTCACGCTGCT
2881    ------------------------------------------------------------ 2940
        CCGGACGCGCGAACCCGTAGGGTAGCCGCGCAGCCCCGCGCCTAGTACCAGTGCGACGA

GAACGCGATGGCGGCGCGGGGCGCGACGCGCGGGGCCGCATCCGTCTGCATCGGCGGGGG
2941    ------------------------------------------------------------ 3000
        CTTGCGCTACCGCCGCGCCCCGCGCTGCGCGCCCCGGCGTAGGCAGACGTAGCCGCCCCC
```

FIG. 24H

```
      CGAGGCGACGGCCATCGCGCTGGAACGGCTGAGCTAATTCATTTGCGCGAATCCGCGTTT
3001  ------------------------------------------------------------  3060
      GCTCCGCTGCCGGTAGCGCGACCTTGCCGACTCGATTAAGTAAACGCGCTTAGGCGCAAA

TTCGTGCACGATGGGGGAACCGGAAACGGCCACGCCTGTTGTGGTTGCGTCGACCTGTCT
3061  ------------------------------------------------------------  3120
      AAGCACGTGCTACCCCCTTGGCCTTTGCCGGTGCGGACAACACCAACGCAGCTGGACAGA

TCGGGCCATGCCCGTGACGCGATGTGGCAGGCGCATGGGCGTTGCCGATCCGGTCGCAT
3121  ------------------------------------------------------------  3180
      AGCCCGGTACGGGCACTGCGCTACACCGTCCGCGTACCCCGCAACGGCTAGGCCAGCGTA

GACTGACGCAACGAAGGCACCGATGACGCCCAAGCAGCAATTCCCCCTACGCGATCTGGT
3181  ------------------------------------------------------------  3240
      CTGACTGCGTTGCTTCCGTGGCTACTGCGGGTTCGTCGTTAAGGGGGATGCGCTAGACCA

CGAGATCAGGCTGGCGCAGATCTCGGGCCAGTTCGGCGTGGTCTCGGCCCCGCTCGGCGC
3241  ------------------------------------------------------------  3300
      GCTCTAGTCCGACCGCGTCTAGAGCCCGGTCAAGCCGCACCAGAGCCGGGGCGAGCCGCG

GGCCATGAGCGATGCCGCCCTGTCCCCCGGCAAACGCTTTCGCGCCGTGCTGATGCTGAT
3301  ------------------------------------------------------------  3360
      CCGGTACTCGCTACGGCGGGACAGGGGCCGTTTGCGAAAGCGCGGCACGACTACGACTA

GGTCGCCGAAAGCTCGGGCGGGGTCTGCGATGCGATGGTCGATGCCGCCTGCGCGGTCGA
3361  ------------------------------------------------------------  3420
      CCAGCGGCTTTCGAGCCCGCCCCAGACGCTACGCTACCAGCTACGGCGGACGCGCCAGCT

GATGGTCCATGCCGCATCGCTGATCTTCGACGACATGCCCTGCATGGACGATGCCAGGAC
3421  ------------------------------------------------------------  3480
      CTACCAGGTACGGCGTAGCGACTAGAAGCTGCTGTACGGGACGTACCTGCTACGGTCCTG

CCGTCGGGGTCAGCCCGCCACCCATGTCGCCCATGGCGAGGGGCGCGCGGTGCTTGCGGG
3481  ------------------------------------------------------------  3540
```

FIG. 24I

```
        GGCAGCGCCAGTCGGGCGGTGGGTACAGCGGGTACCGCTCCCCGCGCGCCACGAACGCCC

CATCGCCCTGATCACCGAGGCCATGCGGATTTTGGGCGAGGCGCGCGGCGCGACGCCGGA
3541    ------------------------------------------------------------ 3600
        GTAGCGGGACTAGTGGCTCCGGTACGCCTAAAACCCGCTCCGCGCGCCGCGCTGCGGCCT

TCAGCGCGCAAGGCTGGTCGCATCCATGTCGCGCGCGATGGGACCGGTGGGGCTGTGCGC
3601    ------------------------------------------------------------ 3660
        AGTCGCGCGTTCCGACCAGCGTAGGTACAGCGCGCGCTACCCTGGCCACCCCGACACGCG

AGGGCAGGATCTGGACCTGCACGCCCCAAGGACGCCGCCGGGATCGAACGTGAACAGGA
3661    ------------------------------------------------------------ 3720
        TCCCGTCCTAGACCTGGACGTGCGGGGGTTCCTGCGGCGGCCCTAGCTTGCACTTGTCCT

CCTCAAGACCGGCGTGCTGTTCGTCGCGGGCCTCGAGATGCTGTCCATTATTAAGGGTCT
3721    ------------------------------------------------------------ 3780
        GGAGTTCTGGCCGCACGACAAGCAGCGCCCGGAGCTCTACGACAGGTAATAATTCCCAGA

GGACAAGGCCGAGACCGAGCAGCTCATGGCCTTCGGGCGTCAGCTTGGTCGGGTCTTCCA
3781    ------------------------------------------------------------ 3840
        CCTGTTCCGGCTCTGGCTCGTCGAGTACCGGAAGCCCGCAGTCGAACCAGCCCAGAAGGT

GTCCTATGACGACCTGCTGGACGTGATCGGCGACAAGGCCAGCACCGGCAAGGATACGGC
3841    ------------------------------------------------------------ 3900
        CAGGATACTGCTGGACGACCTGCACTAGCCGCTGTTCCGGTCGTGGCCGTTCCTATGCCG

GCGCGACACCGCCGCCCCCGGCCCAAAGGGCGGCCTGATGGCGGTCGGACAGATGGGCGA
3901    ------------------------------------------------------------ 3960
        CGCGCTGTGGCGGCGGGGGCCGGGTTTCCCGCCGGACTACCGCCAGCCTGTCTACCCGCT

CGTGGCGCAGCATTACCGCGCCAGCCGCGCGCAACTGGACGAGCTGATGCGCACCCGGCT
3961    ------------------------------------------------------------ 4020
        GCACCGCGTCGTAATGGCGCGGTCGGCGCGCGTTGACCTGCTCGACTACGCGTGGGCCGA
```

```
      GTTCCGCGGGGGCAGATCGCGGACCTGCTGGCCCGCGTGCTGCCGCATGACATCCGCCG
4021  ------------------------------------------------------------ 4080
      CAAGGCGCCCCCGTCTAGCGCCTGGACGACCGGGCGCACGACGGCGTACTGTAGGCGGC

CAGCGCCTAGGCGCGCGGTCGGGTCCACAGGCCGTCGCGGCTGATTTCGCCGCCGCGCAG
4081  ------------------------------------------------------------ 4140
      GTCGCGGATCCGCGCGCCAGCCCAGGTGTCCGGCAGCGCCGACTAAAGCGGCGGCGCCTC

GCGCGATGCGGCCGCGTCCAAGCCTCCGCGCGCCAGAAGCCCGATCTTGGCAGCCTTCGA
4141  ------------------------------------------------------------ 4200
      CGCGCTACGCCGGCGCAGGTTCGGAGGCGCGCGGTCTTCGGGCTAGAACCGTCGGAAGCT

CGTGCTGATCCGCTGGCGATAGGCCTCGGGGCCACCCTGCCGGATGCGCGTCCCGATTGC
4201  ------------------------------------------------------------ 4260
      GCACGACTAGGCGACCGCTATCCGGAGCCCCGGTGGGACGGCCTACGCGCAGGGCTAACG

GCGATAGATACGCAGCGCGGCGGCGATCGACCACGCGCAGCGCGGCGGCAGATGCGGAAG
4261  ------------------------------------------------------------ 4320
      CGCTATCTATGCGTCGCGCCGCCGCTAGCTGGTGCGCGTCGCGCCGCCGTCTACGCCTTC

CCCCTGCCGCGCCGAGGCATAATAGGGCTCGGCCGCGTCAAGCAGGCGGATGATGACGGA
4321  ------------------------------------------------------------ 4380
      GGGGACGGCGCGGCTCCGTATTATCCCGAGCCGGCGCAGTTCGTCCGCCTACTACTGCCT

ATAGAGCGCGTCCGAAGGCACCGGACCCTCAACCGTCGCCCCGCCTCGGCCAGCCAGTC
4381  ------------------------------------------------------------ 4440
      TATCTCGCGCAGGCTTCCGTGGCCTGGGAGTTGGCAGCGGGGGCGGAGCCGGTCGGTCAG

GGCAGGCAGATAGCAGCGCCCGATGGCGGCATCGTCGATCACGTCGCGAGCGATGTTCGT
4441  ------------------------------------------------------------ 4500
      CCGTCCGTCTATCGTCGCGGGCTACCGCCGTAGCAGCTAGTGCAGCGCTCGCTACAAGCA

CAGCTGGAACGCAAGGCCCAGATCGCAGGCGCGATCCAGCACCGCATCGTCCTGCACGCC
4501  ------------------------------------------------------------ 4560
      GTCGACCTTGCGTTCCGGGTCTAGCGTCCGCGCTAGGTCGTGGCGTAGCAGGACGTGCGG

CATCACCCGCGCCATCATCACGCCCACGACCCCGCGACGTGGTAGGAATATTCCAGCAC
4561  ------------------------------------------------------------ 4620
      GTAGTGGGCGCGGTAGTAGTGCGGGTGCTGGGGCGCTGCACCATCCTTATAAGGTCGTG

GTCATCCAGGCTGCGGTATTCGCGATCCGCGACATCCATCGCGAAACCCTCGATCAGGTC
4621  ------------------------------------------------------------ 4680
      CAGTAGGTCCGACGCCATAAGCGCTAGGCGCTGTAGGTAGCGCTTTGGGAGCTAGTCCAG

CATCGGCCAAAGGDCCGGGAAATCATGCCGCCGGGCGACCTGGCGCAGCGCCGCGAAGGG
4681  ------------------------------------------------------------ 4740
      GTAGCCGGTTTCCAGGCCCTTTAGTACGGCGGCCCGCTGGACCGCGTCGCGGCGCTTCCC

CGGCGACATCGGGCCGTCCTCGTGCAGCGCGGCCAGCGTGTCGGCGCGCAGCGCCCCAG
4741  ------------------------------------------------------------ 4800
      GCCGCTGTAGCCCGGCAGGAGCACGTCGCGCCGGTCGCACAGCCGCGCGTCGCGGGGGTC
```

```
        CCGCGCCTGTGGGTCGCCGCCCGCCTCGGGGGCAGAACCCATCACCTGCCCGTCGATCAC
4801    ------------------------------------------------------------  4860
        GGCGCGGACACCCAGCGGCGGGCGGAGCCCCGTCTTGGGTAGTGGACGGGCAGCTAGTG

GTCATCCGCATGCCTGCACCAGGCATAGAGCATGACCGTATCCTCGCGGATGCCGGGCGG
4861    ------------------------------------------------------------  4920
        CAGTAGGCGTACGGACGTGGTCCGTATCTCGTACTGGCATAGGAGCGCCTACGGCCCGCC

CATCAGCTTGGCCGCCTGCGCGAAGCTTTGCGAACCCTGCGCGATGGCCGCTTCGGAAGT
4921    ------------------------------------------------------------  4980
        GTAGTCGAACCGGCGGACGCGCTTCGAAACGCTTGGGACGCGCTACCGGCGAAGCCTTCA
```

```
     GCGCTGCCAACGACACCCGGGATGCCCGCACCCGGATGCGTGCCCGCCCCCACGATGTAG
5041 ------------------------------------------------------------ 5100
     CGCGACGGTTGCTGTGGGCCCTACGGGCGTGGGCCTACGCACGGGCGGGGGTGCTACATC

AAGTTCGGGATCGCGCGGTCGCGGTTATGCGGGCGGAACCAGGCGGATTGCGTCAGGATC
5101 ------------------------------------------------------------ 5160
     TTCAAGCCCTAGCGCGCCAGCGCCAATACGCCCGCCTTGGTCCGCCTAACGCAGTCCTAG

GGCTCGACCGAGAAGGCGCTGCCGTGATGGGCCGACAGTTCGGTGCTGAAATCGGCGGGG
5161 ------------------------------------------------------------ 5220
     CCGAGCTGGCTCTTCCGCGACGGCACTACCCGGCTGTCAAGCCACGACTTTAGCCGCCCC

CTGAAGATGCGGCTGACGGTCAGGTGCTTGCGCAGGTCGGGGATGGCGCGGCGCTCCAGT
5221 ------------------------------------------------------------ 5280
     GACTTCTACGCCGACTGCCAGTCCACGAACGCGTCCAGCCCCTACCGCGCCGCGAGGTCA

TCCTCGAAGATGCGCTCGGCATAGCCCGGGGCCTCGGCTTCCCAATCGACATCGGCGCGG
5281 ------------------------------------------------------------ 5340
     AGGAGCTTCTACGCGAGCCGTATCGGGCCCCGGAGCCGAAGGGTTAGCTGTAGCCGCGCC

CCCAGATGCGGAACGGGCGCAAGGACGTAATGCGTGGACATCCCCTCGGGGCCAGGCTG
5341 ------------------------------------------------------------ 5400
     GGGTCTACGCCTTGCCCGCGTTCCTGCATTACGCACCTGTAGGGGAGCCCCCGGTCCGAC

GGATCGGTCACGCAGGGCGAATGCAGATACATCGAGAAATCGTCCGGCAGGCGTGGCCCG
5401 ------------------------------------------------------------ 5460
     CCTAGCCAGTGCGTCCCGCTTACGTCTATGTAGCTCTTTAGCAGGCCGTCCGCACCGGGC

TTGAAGATCTCGTTCACCAGCCCCTTGTAGCGCGGGCCGAAGATGACGCTGTGGTGGGCC
5461 ------------------------------------------------------------ 5520
     AACTTCTAGAGCAAGTGGTCGGGGAACATCGCGCCCGGCTTCTACTGCGACACCACCCGG

AGGTTCTCGGGGCGCTTGGACAGGCCGAAATGCAGCACGAACAGCGACATCGACCAGCGC
5521 ------------------------------------------------------------ 5580
     TCCAAGAGCCCCGCGAACCTGTCCGGCTTTACGTCGTGCTTGTCGCTGTAGCTGGTCGCG

TGCCGGTTCAGGATCGCGGCCTTGGTGCGCCCGCGGCGGGTATGGCCCAGCAGGTCGCGA
5581 ------------------------------------------------------------ 5640
     ACGGCCAAGTCCTAGCGCCGGAACCACGCGGGCGCCGCCCATACCGGGTCGTCCAGCGCT

TAGCTGTGCATCACGTCGCCGTTGCTGGCCACCGTATCCGCGCGCAACTGCCGCCCGTCC
5641 ------------------------------------------------------------ 5700
     ATCGACACGTAGTGCAGCGGCAACGACCGGTGGCATAGGCGCGCGTTGACGGCGGGCAGG

AGCAGCGTGACGCCCGTGGCGCGATCGCCCTCGGTGTCGATCCGCGTGACGCGGGCATTC
5701 ------------------------------------------------------------ 5760
     TCGTCGCACTGCGGGCACCGCGCTAGCGGGAGCCACAGCTAGGCGCACTGCGCCCGTAAG

AGCAGCAGCGTGCCGCCAAGACGCTCGAACAGGGCGACCATGCCCGCGACCAGCTGGTTG
5761 ------------------------------------------------------------ 5820
     TCGTCGTCGCACGGCGGTTCTGCGAGCTTGTCCCGCTGGTACGGGCGCTGGTCGACCAAC
```

```
         GTGCCGCCCTTGGCGAACCAGACGCCGCCGCGCCGTTCCAGCGCATGGATCAGCGCATAG
5821     ------------------------------------------------------------  5880
         CACGGCGGGAACCGCTTGGTCTGCGGCGGCGCGGCAAGGTCGCGTACCTAGTCGCGTATC

ATCGAGCTGGTCGAAAACGGGTTCCCGCCGACCAGCAGCGTGTGGAACGAGAAGGCCTGC
5881     ------------------------------------------------------------  5940
         TAGCTCGACCAGCTTTTGCCCAAGGGCGGCTGGTCGTCGCACACCTTGCTCTTCCGGACG

CGCAGATGCGGGTCCTGGATGAAGCGCGCCACCATGCTGTGGACCGAGCGGTATGCCTGC
5941     ------------------------------------------------------------  6000
         GCGTCTACGCCCAGGACCTACTTCGCGCGGTGGTACGACACCTGGCTCGCCATACGGACG

AGGCGCATCAGCGCCGGCGCGGCGTTCAGCATCTGGCCCAGCTTCAGGAAGGGCGTGGTC
6001     ------------------------------------------------------------  6060
         TCCGCGTAGTCGCGGCCGCCCCGCAAGTCGTAGACCGGGTCGAAGTCCTTCCCGCACCAG
```

```
      CCCAGCTTCAGATACCCCTCGCGATAGACCTCCTCGGCGTAATCGTGGAAGCGGCGATAG
6061  ------------------------------------------------------------ 6120
      GGGTCGAAGTCTATGGGGAGCGCTATCTGGAGGAGCCGCATTAGCACCTTCGCCGCTATC

CCATCGACATCGGCGGGATTGAAGGAGCCGACCTGGCGGATCAGCTCGTCGTCGTCGTTC
6121  ------------------------------------------------------------ 6180
      GGTAGCTGTAGCCGCCCTAACTTCCTCGGCTGGACCGCCTAGTCGAGCAGCAGCAGCAAG

ACGTATTCGAAGCTGCGGCCGTCCGCCCATGTCAGCCGGTAGAAGGGCGAGACCGGCAGC
6181  ------------------------------------------------------------ 6240
      TGCATAAGCTTCGACGCCGGCAGGCGGGTACAGTCGGCCATCTTCCCGCTCTGGCCGTCG

AGCGTCACGTCACGCTCCATCGGTTGGCCGCTGAGGGCCCCACAGCTCTCGCAGGCGTCG
6241  ------------------------------------------------------------ 6300
      TCGCAGTGCAGTGCGAGGTAGCCAACCGGCGACTCCCGGGTGTCGAGAGCGTCCGACAGC

GGGTCGGTCACGACCGTCGGGCCTGCATCGAAGACGTGGCCCTGATCGTTCCAGACATAG
6301  ------------------------------------------------------------ 6360
      CCCAGCCAGTGCTGGCAGCCCGGACGTAGCTTCTGCACCGGGACTAGCAAGGTCTGTATC

GCGCGGCCGCCGGGCTTGTCGCGGGCCTCGACGATGGTGGTCGCGATGCCGGCCGATTGC
6361  ------------------------------------------------------------ 6420
      CGCGCCGGCGGCCCGAACAGCGCCCGGAGCTGCTACCACCAGCGCTACGGCCGGCTAACG

AGGCGGATGGCAAGCGCAAGCCCGCCGAAACCTGCGCCGATGACGATGGCGGAACTCATG
6421  ------------------------------------------------------------ 6480
      TCCGCCTACCGTTCGCGTTCGGGCGGCTTTGGACGCGGCTACTGCTACCGCCTTGAGTAC

CTCTCTCCTGCAGCAGGGGCGTTCGGGCAGGCAGCGCACGGCCTGCGACAGCGGAATGG
6481  ------------------------------------------------------------ 6540
      GAGAGAGGACGTCGTCCCCCGCAAGCCCGTCCGTCGCGTGCCGGACGCTGTCGCCTTACC

GAGAGAGGACGTCGTCCCCCGCAAGCCCGTCCGTCGCGTGCCGGACGCTGTCGCCTTACC
6541  ------------------------------------------------------------ 6600
      CGCCCGCAGGCCACTGCTACGCTTCGGCCAGCCGGTTACAGTCCGCGGGCCGTATCTTCG

GCTCGATCAGCGGCTGCGGCAGGCGGTAGAACCGCTGCAGCAGGCGATAGCGACGGTCGG
6601  ------------------------------------------------------------ 6660
      CGAGCTAGTCGCCGACGCCGTCCGCCATCTTGGCGACGTCGTCCGCTATCGCTGCCAGCC

GCGGGCAGCCGCGGAACAGCATCCGGTTCAGCAGCCGCAGGAAGCGGTCGCGATCCGCGC
6661  ------------------------------------------------------------ 6720
      CGCCCGTCGGCGCCTTGTCGTAGGCCAAGTCGTCGGCGTCCTTCGCCAGCGCTAGGCGCG

GATCGATGGCCCAGCCGCGCACCGCGCGACGGGCGGACGCGGTCGTCAGGTCGCGCGCCG
6721  ------------------------------------------------------------ 6780
      CTAGCTACCGGGTCGGCGCGTGGCGCGCTGCCCGCCTGCGCCAGCAGTCCAGCGCGCGGC

CGATGGCATCCGCGACCTGCGCGGCATAGGGCAGCGAATATCCGGTGACGGGGTGGAACA
6781  ------------------------------------------------------------ 6840
      GCTACCGTAGGCGCTGGACGCGCCGTATCCCGTCGCTTATAGGCCACTGCCCCACCTTGT
```

```
       GCCCTGCCCCCAGCCCAACCGGCACCGCCCCCTGCGCGTGGTCGCGCCAGAAGCCTATGG
6841   ------------------------------------------------------------ 6900
       CGGGACGGGGGTCGGGTTGGCCGTGGCGGGGACGCGCACCAGCGCGGTCTTCGGATACC

CGTCATGGGCCAGCGCGATGGGCAGGATGCCCCTTTCGCGCCGCATCTCCTGCCCGGTCC
6901   ------------------------------------------------------------ 6960
       GCAGTACCCGGTCGCGCTACCCGTCCTACGGGGAAAGCGCGGCGTAGAGGACGGGCCAGG

AGCCCCGCCTGGCGGCATAGTCCAGCGACGCCTGCGCCAGCGCGCCATCGTCCAGATCGC
6961   ------------------------------------------------------------ 7020
       TCGGGGCGGACCGCCGTATCAGGTCGCTGCGGACGCGGTCGCGCGGTAGCAGGTCTAGCG
```

```
      CGCCGTCGCTGTAGCGCGTATCCTCGATCAGGATGCGGGTGGGACTGAAGGGCAGCAGAT
7021  ------------------------------------------------------------ 7080
      GCGGCAGCGACATCGCGCATAGGAGCTAGTCCTACGCCCACCCTGACTTCCCGTCGTCTA

AGATGAAGCGGTACCCGTCCATCTGCGGAACGGTCGCGTCCATGATCATCGGGCGCTCGA
7081  ------------------------------------------------------------ 7140
      TCTACTTCGCCATGGGCAGGTAGACGCCTTGCCAGCGCAGGTACTAGTAGCCCGCGAGCT

CGCCATGGGGGCGTCGGTCTCGATCTCGACGCCCACGAATTTCTGGAAACCCACGGTCA
7141  ------------------------------------------------------------ 7200
      GCGGTACCCCCGCAGCCAGAGCTAGAGCTGCGGGTGCTTAAAGACCTTTGGGTGCCAGT

GGTGCGGGGTCTCGACGGCACCACGGGCGTCGATCACGCAGGCAGCCTCGATCCGCGAGC
7201  ------------------------------------------------------------ 7260
      CCACGCCCCAGAGCTGCCGTGGTGCCCGCAGCTAGTGCGTCCGTCGGAGCTAGGCGCTCG

CGTCCGTCAGCGTCGCGCCGGTATCGTCCAGCGTCGCGACATGCGTATTCCACCGCAGAT
7261  ------------------------------------------------------------ 7320
      GCAGGCAGTCGCAGCGCGGCCATAGCAGGTCGCAGCGCTGTACGCATAAGGTGGCGTCTA

CGACACCCTGCAGCAGCCCGATCAGCGCGCCCGCCTCGATCGAGCCATAGCCTGTCGTCA
7321  ------------------------------------------------------------ 7380
      GCTGTGGGACGTCGTCGGGCTAGTCGCGCGGGCGGAGCTAGCTCGGTATCGGACAGCAGT

GGCGGCGCGAATGGTCGGGAAACGCGACCTCCTGATCCGTCCATTCGCCGCGACGAATGG
7381  ------------------------------------------------------------ 7440
      CCGCCGCGCTTACCAGCCCTTTGCGCTGGAGGACTAGGCAGGTAAGCGGCGCTGCTTACC

GCGACAGGCGCGCCAGCCATTCGGGCGAAAGATCCGTGTCGTGGCAGGACCAGGTGTGCT
7441  ------------------------------------------------------------ 7500
      CGCTGTCCGCGCGGTCGGTAAGCCCGCTTTCTAGGCACAGCACCGTCCTGGTCCACACGA

GGTCCGAGGGGCCGGACCGCGCGTCGAGCATCACGATGCGCGCATCCGGTCTGCGGTCGC
7501  ------------------------------------------------------------ 7560
      CCAGGCTCCCCGGCCTGGCGCGCAGCTCGTAGTGCTACGCGCGTAGGCCAGACGCCAGCG

GAACGGCAAGCGCGATCAGCGCACCGGACAGCCCCGCGCCCGCGATCAGCAGATCATGGC
7561  ------------------------------------------------------------ 7620
      CTTGCCGTTCGCGCTAGTCGCGTGGCCTGTCGGGGCGCGGGCGCTAGTCGTCTAGTACCG

TCATGTATTGCGATCCGCCCCTTCGCGGTCCTTCAGCAGCGCGCCCCAGCGTTTCAGCTC
7621  ------------------------------------------------------------ 7680
      AGTACATAACGCTAGGCGGGGAAGCGCCAGGAAGTCGTCGCGCGGGCTCGCAAAGTCGAG

TGCCTTGAGGCTGTCGACCGAGGGCGCCCAGATGAAACCGAAGCTGACGCAGTTCTCGCG
7681  ------------------------------------------------------------ 7740
      ACGGAACTCCGACAGCTGGCTCCCGCGGGTCTACTTTGGCTTCGACTGCGTCAAGAGCGC

GCCATGGACCGCGTGATGCATCCTGTGTGCCTGGTAGACGCGACGAAGATAGCCGCGCTT
7741  ------------------------------------------------------------ 7800
      CGGTACCTGGCGCACTACGTAGGACACACGGACCATCTGCGCTGCTTCTATCGGCGCGAA
```

```
            GGGGACATAGCGGAACGGCCAGCGCCCATGCACCAAGCCGTCATGCAGGAAATAGTAGAT
    7801    ------------------------------------------------------------ 7860
            CCCCTGTATCGCCTTGCCGGTCGCGGGTACGTGGTTCGGCAGTACGTCCTTTATCATCTA

CAGCCCGTAGCAGGTGACCCCCACCGCCAGCCACCAGGCCAGATCCGACCCCATCGCGCC
    7861    ------------------------------------------------------------ 7920
            GTCGGGCATCGTCCACTGGGGGTGGCGGTCGGTGGTCCGGTCTAGGCTGGGGTAGCGCGG

GATCGCGAACAGCACGATCGAGATTACCGCGAAGATGACGCCATAGAGGTCGTTCTTCTC
    7921    ------------------------------------------------------------ 7980
            CTAGCGCTTGTCGTGCTAGCTCTAATGGCGCTTCTACTGCGGTATCTCCAGCAAGAAGAG
```

```
     GAGCGCGTGGTCGTGATCCTCGTCGTGGTGCGATTTATGCCAGCCCCAGCCCAGGGGGCC
7981 ------------------------------------------------------------ 8040
     CTCGCGCACCAGCACTAGGAGCAGCACCACGCTAAATACGGTCGGGGTCGGGTCCCCGG

ATGCATGATCCACCGATGGACGGAGTAGGCCGTCAGCTCCATCGCGGCGACGGTCAGGAT
8041 ------------------------------------------------------------ 8100
     TACGTACTAGGTGGCTACCTGCCTCATCCGGCAGTCGAGGTAGCGCCGCTGCCAGTCCTA

GACGGTCAGGATTGCGGCCCAAGTGCTCATGCCGGCCCCTTGCTTGATATGACAGGGAAC
8101 ------------------------------------------------------------ 8160
     CTGCCAGTCCTAACGCCGGGTTCACGAGTACGGCCGGGGAACGAACTATACTGTCCCTTG

AGGCTACGCTGCCGCGCGGTGCATGACCAGCCCATCGGGGTGCGACCAAAGGGCATCGCG
8161 ------------------------------------------------------------ 8220
     TCCGATGCGACGGCGCGCCACGTACTGGTCGGGTAGCCCCACGCTGGTTTCCCGTAGCGC

TGACATCTGCGTTCAGGGCTCATAGGCGGATCATCCGTGACATTCGCCGCCGAACGCGGC
8221 ------------------------------------------------------------ 8280
     ACTGTAGACGCAAGTCCCGAGTATCCGCCTAGTAGGCACTGTAAGCGGCGGCTTGCGCCG

AGGCGCATCACGCGTTCCGTCGCTGGAAATATTAATGTTTTCCCGAAGATGGTCGGGGCG
8281 ------------------------------------------------------------ 8340
     TCCGCGTAGTGCGCAAGGCAGCGACCTTTATAATTACAAAAGGGCTTCTACCAGCCCCGC

AGAGGATTCGAACCTCCGACCTACGGTACCCAAAACCGTCGCGCTACCAGGCTGCGCTAC
8341 ------------------------------------------------------------ 8400
     TCTCCTAAGCTTGGAGGCTGGATGCCATGGGTTTTGGCAGCGCGATGGTCCGACGCGATG

GCCCCGACTGCGGAAGGCTTTAGCCGATTGTTCCGGCAAGGGAAAGACCTAGTCGCAGGC
8401 ------------------------------------------------------------ 8460
     CGGGGCTGACGCCTTCCGAAATCGGCTAACAAGGCCGTTCCCTTTCTGGATCAGCGTCCG

CAGGACCGCATTGTCGCCCATGCCCGGATGCGCCATCGGCTGACCGGGCTTCAGGCCAAG
8461 ------------------------------------------------------------ 8520
     GTCCTGGCGTAACAGCGGGTACGGGCCTACGCGGTAGCCGACTGGCCCGAAGTCCGGTTC

GCGATCCGCCTCTCCGCCCGCGATTTCGAGGACGAACAGCCGGTCGGGGTCCGGATCGCC
8521 ------------------------------------------------------------ 8580
     CGCTAGGCGGAGAGGCGGGCGCTAAAGCTCCTGCTTGTCGGCCAGCCCCAGGCCTAGCGG

GACCGCCGCGCCCGGAATGGGCGTCTCGTCCAGCGGGCGCGCATTGCGGTGGATGTGGCG
8581 ------------------------------------------------------------ 8640
     CTGGCGGCGCGGGCCTTACCCGCAGAGCAGGTCGCCCGCGCGTAACGCCACCTACACCGC

GATGACGCCGGTTTCATCCGCAAAGACCATGTCCAGCGGGATCAGTGTGTTGCGCATCCA
8641 ------------------------------------------------------------ 8700
     CTACTGCGGCCAAAGTAGGCGTTTCTGGTACAGGTCGCCCTAGTCACACAACGCGTAGGT

GAAGGACACCGGCTGGGGCGATTCGTAGATGAACAGCATTCCGGTGCCCGCAGGCAGCTC
8701 ------------------------------------------------------------ 8760
     GAACGCCTTGTAGTCCGGGACGCGCGCGAGAAGCCCCGACAGGCGCTGGAGCTGGGCTTT
```

```
       CCCGAGCGTTTCCGCACCGGTATCGACGACAAGACTGCCGGGCGCGCATTCCACCGCCGC
8821   ------------------------------------------------------------ 8820
       GGGCTCGCAAAGGCGTGGCCATAGCTGCTGTTCTGACGGCCCGCGCGTAAGGTGGCGGCG

CGCGGCGGCGGGCATCAGGACCGCAAGAAGCGCTGCGGCCTTACTCGGCCACATGGGCAA
8881   ------------------------------------------------------------ 8940
       GCGCCGCCGCCCGTAGTCCTGGCGTTCTTCGCGACGCCGGAATGAGCCGGTGTACCCGTT
```

```
        ATACCGTCGACCTCGAGGGGGGCCCGGTACCCAGCTTTTGTTCCCTTTAGTGAGGGTTA
9001    ------------------------------------------------------------  9060
        TATGGCAGCTGGAGCTCCCCCCGGGCCATGGGTCGAAAACAAGGGAAATCACTCCCAAT

ATTGCGCGCTTGGCGTAATCATGGTCATAGCTGTTTCCTGTGTGAAATTGTTATCCGCTC
9061    ------------------------------------------------------------  9120
        TAACGCGCGAACCGCATTAGTACCAGTATCGACAAAGGACACACTTTAACAATAGGCGAG

ACAATTCCACACAACATACGAGCCGGAAGCATAAAGTGTAAAGCCTGGGGTGCCTAATGA
9121    ------------------------------------------------------------  9180
        TGTTAAGGTGTGTTGTATGCTCGGCCTTCGTATTTCACATTTCGGACCCCACGGATTACT

GTGAGCTAACTCACATTAATTGCGTTGCGCTCACTGCCCGCTTTCCAGTCGGGAAACCTG
9181    ------------------------------------------------------------  9240
        CACTCGATTGAGTGTAATTAACGCAACGCGAGTGACGGGCGAAAGGTCAGCCCTTTGGAC

TCGTGCCAGCTGCATTAATGAATCGGCCAACGCGCGGGGAGAGGCGGTTTGCGTATTGGG
9241    ------------------------------------------------------------  9300
        AGCACGGTCGACGTAATTACTTAGCCGGTTGCGCGCCCCTCTCCGCCAAACGCATAACCC

CGCTCTTCCGCTTCCTCGCTCACTGACTCGCTGCGCTCGGTCGTTCGGCTGCGGCGAGCG
9301    ------------------------------------------------------------  9360
        GCGAGAAGGCGAAGGAGCGAGTGACTGAGCGACGCGAGCCAGCAAGCCGACGCCGCTCGC

GTATCAGCTCACTCAAAGGCGGTAATACGGTTATCCACAGAATCAGGGGATAACGCAGGA
9361    ------------------------------------------------------------  9420
        CATAGTCGAGTGAGTTTCCGCCATTATGCCAATAGGTGTCTTAGTCCCCTATTGCGTCCT

AAGAACATGTGAGCAAAAGGCCAGCAAAAGGCCAGGAACCGTAAAAAGGCCGCGTTGCTG
9421    ------------------------------------------------------------  9480
        TTCTTGTACACTCGTTTTCCGGTCGTTTTCCGGTCCTTGGCATTTTTCCGGCGCAACGAC

GCGTTTTTCCATAGGCTCCGCCCCCCTGACGAGCATCACAAAAATCGACGCTCAAGTCAG
9481    ------------------------------------------------------------  9540
        CGCAAAAAGGTATCCGAGGCGGGGGGACTGCTCGTAGTGTTTTTAGCTGCGAGTTCAGTC

AGGTGGCGAAACCCGACAGGACTATAAAGATACCAGGCGTTTCCCCCTGGAAGCTCCCTC
9541    ------------------------------------------------------------  9600
        TCCACCGCTTTGGGCTGTCCTGATATTTCTATGGTCCGCAAAGGGGACCTTCGAGGGAG

GTGCGCTCTCCTGTTCCGACCCTGCCGCTTACCGGATACCTGTCCGCCTTTCTCCCTTCG
9601    ------------------------------------------------------------  9660
        CACGCGAGAGGACAAGGCTGGGACGGCGAATGGCCTATGGACAGGCGGAAAGAGGGAAGC

GGAAGCGTGGCGCTTTCTCATAGCTCACGCTGTAGGTATCTCAGTTCGGTGTAGGTCGTT
9661    ------------------------------------------------------------  9720
        CCTTCGCACCGCGAAAGAGTATCGAGTGCGACATCCATAGAGTCAAGCCACATCCAGCAA

CGCTCCAAGCTGGGCTGTGTGCACGAACCCCCCGTTCAGCCCGACCGCTGCGCCTTATCC
9721    ------------------------------------------------------------  9780
        GCGAGGTTCGACCCGACACACGTGCTTGGGGGGCAAGTCGGGCTGGCGACGCGGAATAGG
```

```
        GGTAACTATCGTCTTGAGTCCAACCCGGTAAGACACGACTTATCGCCACTGGCAGCAGCC
9781    ------------------------------------------------------------ 9840
        CCATTGATAGCAGAACTCAGGTTGGGCCATTCTGTGCTGAATAGCGGTGACCGTCGTCGG

ACTGGTAACAGGATTAGCAGAGCGAGGTATGTAGGCGGTGCTACAGAGTTCTTGAAGTGG
9841    ------------------------------------------------------------ 9900
        TGACCATTGTCCTAATCGTCTCGCTCCATACATCCGCCACGATGTCTCAAGAACTTCACC

TGGCCTAACTACGGCTACACTAGAAGGACAGTATTTGGTATCTGCGCTCTGCTGAAGCCA
9901    ------------------------------------------------------------ 9960
        ACCGGATTGATGCCGATGTGATCTTCCTGTCATAAACCATAGACGCGAGACGACTTCGGT
```

```
        GTTACCTTCGGAAAAAGAGTTGGTAGCTCTTGATCCGGCAAACAAACCACCGCTGGTAGC
  9961  ------------------------------------------------------------
 10020
        CAATGGAAGCCTTTTTCTCAACCATCGAGAACTAGGCCGTTTGTTTGGTGGCGACCATCG

GGTGGTTTTTTTGTTTGCAAGCAGCAGATTACGCGCAGAAAAAAAGGATCTCAAGAAGAT
 10021  ------------------------------------------------------------
 10080
        CCACCAAAAAAACAAACGTTCGTCGTCTAATGCGCGTCTTTTTTTCCTAGAGTTCTTCTA

CCTTTGATCTTTTCTACGGGGTCTGACGCTCAGTGGAACGAAAACTCACGTTAAGGGATT
 10081  ------------------------------------------------------------
 10140
        GGAAACTAGAAAAGATGCCCCAGACTGCGAGTCACCTTGCTTTTGAGTGCAATTCCCTAA

TTGGTCATGAGATTATCAAAAGGATCTTCACCTAGATCCTTTTAAATTAAAAATGAAGT
 10141  ------------------------------------------------------------
 10200
        AACCAGTACTCTAATAGTTTTTCCTAGAAGTGGATCTAGGAAAATTTAATTTTTACTTCA

TTTAAATCAATCTAAAGTATATATGAGTAAACTTGGTCTGACAGTTACCAATGCTTAATC
 10201  ------------------------------------------------------------
 10260
        AAATTTAGTTAGATTTCATATATACTCATTTGAACCAGACTGTCAATGGTTACGAATTAG

AGTGAGGCACCTATCTCAGCGATCTGTCTATTTCGTTCATCCATAGTTGCCTGACTCCCC
 10261  ------------------------------------------------------------
 10320
        TCACTCCGTGGATAGAGTCGCTAGACAGATAAAGCAAGTAGGTATCAACGGACTGAGGGG

GTCGTGTAGATAACTACGATACGGGAGGGCTTACCATCTGGCCCCAGTGCTGCAATGATA
 10321  ------------------------------------------------------------
 10380
        CAGCACATCTATTGATGCTATGCCCTCCCGAATGGTAGACCGGGGTCACGACGTTACTAT

CCGCGAGACCCACGCTCACCGGCTCCAGATTTATCAGCAATAAACCAGCCAGCCGGAAGG
 10381  ------------------------------------------------------------
 10440
        GGCGCTCTGGGTGCGAGTGGCCGAGGTCTAAATAGTCGTTATTTGGTCGGTCGGCCTTCC

GCCGAGCGCAGAAGTGGTCCTGCAACTTTATCCGCCTCCATCCAGTCTATTAATTGTTGC
 10441  ------------------------------------------------------------
 10500
        CGGCTCGCGTCTTCACCAGGACGTTGAAATAGGCGGAGGTAGGTCAGATAATTAACAACG

CGGGAAGCTAGAGTAAGTAGTTCGCCAGTTAATAGTTTGCGCAACGTTGTTGCCATTGCT
 10501  ------------------------------------------------------------
 10560
        GCCCTTCGATCTCATTCATCAAGCGGTCAATTATCAAACGCGTTGCAACAACGGTAACGA

ACAGGCATCGTGGTGTCACGCTCGTCGTTTGGTATGGCTTCATTCAGCTCCGGTTCCCAA
```

```
10561 ------------------------------------------------------------
10620
      TGTCCGTAGCACCACAGTGCGAGCAGCAAACCATACCGAAGTAAGTCGAGGCCAAGGGTT

CGATCAAGGCGAGTTACATGATCCCCATGTTGTGCAAAAAAGCGGTTAGCTCCTTCGGT
10621 ------------------------------------------------------------
10680
      GCTAGTTCCGCTCAATGTACTAGGGGGTACAACACGTTTTTTCGCCAATCGAGGAAGCCA

CCTCCGATCGTTGTCAGAAGTAAGTTGGCCGCAGTGTTATCACTCATGGTTATGGCAGCA
10681 ------------------------------------------------------------
10740
      GGAGGCTAGCAACAGTCTTCATTCAACCGGCGTCACAATAGTGAGTACCAATACCGTCGT

CTGCATAATTCTCTTACTGTCATGCCATCCGTAAGATGCTTTTCTGTGACTGGTGAGTAC
10741 ------------------------------------------------------------
10800
      GACGTATTAAGAGAATGACAGTACGGTAGGCATTCTACGAAAAGACACTGACCACTCATG

TCAACCAAGTCATTCTGAGAATAGTGTATGCGGCGACCGAGTTGCTCTTGCCCGGCGTCA
10801 ------------------------------------------------------------
10850
      AGTTGGTTCAGTAAGACTCTTATCACATACGCCGCTGGCTCAACGAGAACGGGCCGCAGT

ATACGGGATAATACCGCGCCACATAGCAGAACTTTAAAAGTGCTCATCATTGGAAAACGT
10861 ------------------------------------------------------------
10920
      TATGCCCTATTATGGCGCGGTGTATCGTCTTGAAATTTTCACGAGTAGTAACCTTTTGCA

TCTTCGGGGCGAAAACTCTCAAGGATCTTACCGCTGTTGAGATCCAGTTCGATGTAACCC
10921 ------------------------------------------------------------
10980
      AGAAGCCCCGCTTTTGAGAGTTCCTAGAATGGCGACAACTCTAGGTCAAGCTACATTGGG
```

*FIG. 24X*

```
        ACTCGTGCACCCAACTGATCTTCAGCATCTTTTACTTTCACCAGCGTTTCTGGGTGAGCA
10981   ------------------------------------------------------------
11040
        TGAGCACGTGGGTTGACTAGAAGTCGTAGAAAATGAAAGTGGTCGCAAAGACCCACTCGT

AAAACAGGAAGGCAAAATGCCGCAAAAAGGGAATAAGGGCGACACGGAAATGTTGAATA
11041   ------------------------------------------------------------
11100
        TTTTGTCCTTCCGTTTTACGGCGTTTTTCCCTTATTCCCGCTGTGCCTTTACAACTTAT

CTCATACTCTTCCTTTTTCAATATTATTGAAGCATTTATCAGGGTTATTGTCTCATGAGC
11101   ------------------------------------------------------------
11160
        GAGTATGAGAAGGAAAAAGTTATAATAACTTCGTAAATAGTCCCAATAACAGAGTACTCG

GGATACATATTTGAATGTATTTAGAAAAATAAACAAATAGGGGTTCCGCGCACATTTCCC
11161   ------------------------------------------------------------
11220
        CCTATGTATAAACTTACATAAATCTTTTTATTTGTTTATCCCCAAGGCGCGTGTAAAGGG

CGAAAAGTGCCAC
11221   ------------- 11233
        GCTTTTCACGGTG
```

… # FERMENTATIVE CAROTENOID PRODUCTION

BACKGROUND OF THE INVENTION

Over 600 different carotenoids have been described from carotenogenic organisms found among bacteria, yeast, fungi and plants. Currently only two of them, β-carotene and astaxanthin are commercially produced in microorganisms and used in the food and feed industry. β-carotene is obtained from algae and astaxanthin is produced in Pfaffia strains which have been generated by classical mutation. However, fermentation in Pfaffia has the disadvantage of long fermentation cycles and recovery from algae is cumbersome. Therefore, it is desiderable to develop production systems which have better industrial applicability, e.g., can be manipulated for increased titers and/or reduced fermentation times.

Two such systems using the biosynthetic genes form *Erwinia herbicola* and *Erwinia uredovora* have already been described in WO 91/13078 and EP 393 690, respectively. Furthermore, three β-carotene ketolase genes (β-carotene β-4-oxygenase) of the marine bacteria *Agrobacterium aurantiacum* and Alcaligenes strain PC-1 (crtW) [Misawa, 1995, Biochem. Biophys. Res. Com. 209, 867–876] [Misawa, 1995, J. Bacteriology 177, 6575–6584] and from the green algae *Haematococcus pluvialis* (bkt) [Lotan, 1995, FEBS Letters 364, 125–128][Kajiwara, 1995, Plant Mol. Biol. 29, 343–352] have been cloned. *E. coli* carrying either the carotenogenic genes (crtE, crtB, crtY and crtI) of *E. herbicola* [Hundle, 1994, MGG 245, 406–416] or of *E. uredovora* and complemented with the crtW gene of *A. aurantiacum* [Misawa, 1995] or the bkt gene of *H. pluvialis* [Lotan, 1995][Kajiwara, 1995] resulted in the accumulation of canthaxanthin (β,β-carotene-4,4'-dione), originating from the conversion of β-carotene, via the intermediate echinenone (β,β-carotene-4-one).

Introduction of the above mentioned genes (crtW or bkt) into *E. coli* cells harbouring besides the carotenoid biosynthesis genes mentioned above also the crtZ gene of *E. uredovora* [Kajiwara, 1995][Misawa, 1995], resulted in both cases in the accumulation of astaxanthin (3,3'-dihydroxy-β, β-carotene-4,4'-dione). The results obtained with the bkt gene are in contrast to the observation made by others [Lotan, 1995], who using the same experimental set-up, but introducing the *H. pluvialis* bkt gene in a zeaxanthin (β,β-carotene-3,3'-diol) synthesising *E. coli* host harbouring the carotenoid biosynthesis genes of *E. hericola*, a close relative of the above mentioned *E. uredovora* strain, did not observe astaxanthin production.

However, functionally active combinations of the carotenoid biosynthesising genes of the present invention with the known crtW genes have not been shown so far and even more importantly there is a continuing need in even more optimized fermentation systems for industrial application.

SUMMARY OF THE INVENTION

Novel proteins of Flavobacterium sp. R1534 and the DNA sequences which encode these proteins have been discovered which provide an improved biosynthetic pathway from farnesyl pyrophosphate and isopentyl pyrophosphate to various carotenoids, especially β-carotene, lycopene, zeaxanthin and cantaxanthin.

BRIEF DESCRIPTION OF THE FIGURES

FIGS. 7A to 7C1: Nucleotide sequence of the Flavobacterium sp. R1534 carotenoid biosynthesis cluster and its flanking regions. The nucleotide sequence is numbered from the first nucleotide shown (see BamHI site of FIG. 6). The deduced amino acid sequence of the ORF's (orf-5, orf-1, crtE, [SEQ ID NO: 1] crtB, [SEQ ID NO: 3] crtI [SEQ ID NO: 5] crtY, [SEQ ID NO: 7] crtZ [SEQ ID NO: 9] and orf-16) are shown with the single-letter amino acid code. Arrow (→) indicate the direction of the transcription; asterisks, stop codons.

FIG. 8: Amino acid sequence of the GGPP synthase (crtE) of Flavobacterium sp. R1534 [SEQ ID NO: 1] with a MW of 31331 Da.

FIG. 9: Amino acid sequence of the prephytoene synthetase (crtB) of Flavobacterium sp. R1534 [SEQ ID NO: 3] with a MW of 32615 Da.

FIG. 10: Amino acid sequence of the phytoene desaturase (crtI) of Flavobacterium sp. R1534 [SEQ ID NO: 5] with a MW of 54411 Da.

FIG. 11: Amino acid sequence of the lycopene cyclase (crtY) of Flavobacterium sp. R1534 [SEQ ID NO: 7] with a MW of 42368 Da.

FIG. 12: Amino acid sequence of the β-carotene hydroxylase (crtZ) of Flavobacterium sp. R1534 [SEQ ID NO: 9] with a MW of 19282 Da.

FIG. 14: Primers used for PCR reactions (SEQ ID NO: 28 through SEQ ID NO: 39). The underlined sequence is the recognition site of the indicated restriction enzyme. Small caps indicate nucleotides introduced by mutagenesis. Boxes show the artificial RBS which is recognized in *B. subtilis*. Small caps in bold show the location of the original adenine creating the translation start site (ATG) of the following gene (see original operon). All the ATG's of the original Flavobacter carotenoid biosynthetic genes had to be destroyed to not interfere with the rebuild transcription start site. Arrows indicate start and ends of the indicated Flavobacterium R1534 WT carotenoid genes.

FIG. 15: Linkers used for the different constructions (SEQ ID NO: 40 through SEQ ID NO: 47). The underlined sequence is the recognition site of the indicated restriction enzyme. Small caps indicate nucleotides introduced by synthetic primers. Boxes show the artificial RBS which is recognized in *B. subtilis*. Arrow indicate start and ends of the indicated Flavobacterium carotenoid genes.

FIG. 21: Norhern blot analysis of *B. subtilis* strain BS1012::ZYIB-EINV4.

FIGS. 24A–24Y: Complete nucleotide sequence of plasmid pZea4.

FIG. 25: Synthetic crtW gene of Alcaligenes PC-1. The translated protein sequence is shown above the double stranded DNA sequence. The twelve oligonucleotides (crtW1–crtW12) used for the PCR synthesis are underlined.

DETAILED DESCRIPTION OF THE INVENTION

Figure 1:
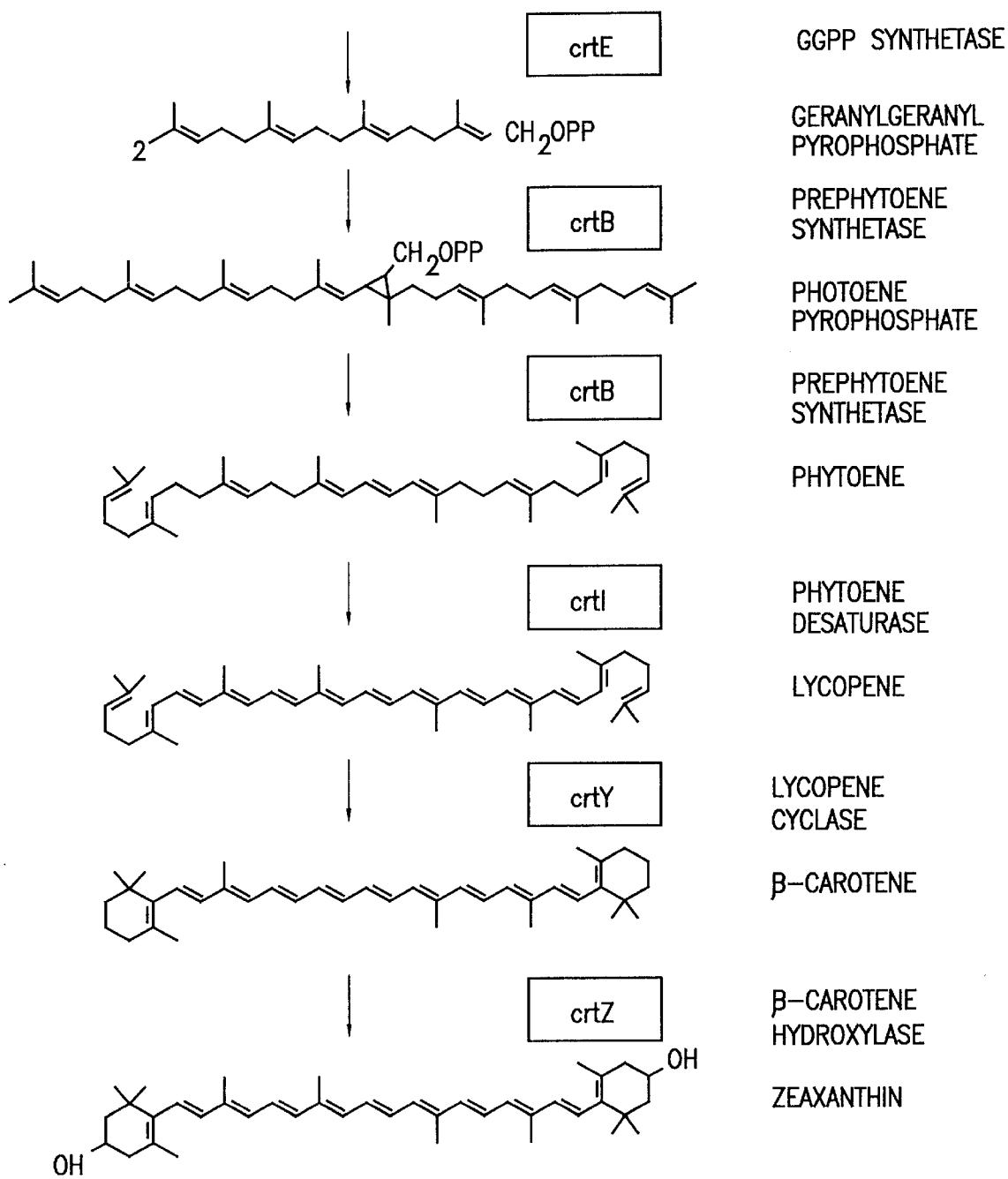
FIG. 1: The biosynthesis pathway for the formation or carotenoids of Flavobacterium sp. R1534 is illustrated explaining the enzymatic activities which are encoded by DNA sequences of the present invention.

Novel proteins of Flavobacterium sp. R1534 and the DNA sequences which encode these proteins have been discovered which provide an improved biosynthetic pathway from farnesyl pyrophosphate and isopentyl pyrophosphate to various carotenoid precursors and carotenoids, especially β-carotene, lycopene, zeaxanthin and cantaxanthin.

One aspect of the invention is the geranylgeranyl pyrophosphate (GGPP) synthase of Flavobacterium sp. R1534 and a polynucleotide comprising a DNA sequence which encodes said GGPP synthase (crtE), said synthase and polynucleotide being substantially free of other proteins and polynucleotides, respectively, of Flavobacterium sp. R1534. Also encompassed by this aspect of the present invention is a polynucleotide comprising a DNA sequence which is substantially homologous to said DNA sequence. Said GGPP synthase catalyzes the condensation of farnesyl pyrophosphate and isopentyl pyrophosphate to obtain geranylgeranyl pyrophosphate, a carotenoid precursor. The preferred GGPP synthase has the amino acid sequence of FIG. 8 [SEQ ID NO: 1], and the preferred DNA sequence encodes said amino acid sequence. The especially preferred DNA sequence is bases 2521–3408 shown in FIG. 7 [SEQ ID NO: 2].

This aspect of the present invention also includes a vector comprising the aforesaid polynucleotide, preferably in the form of an expression vector. Furthermore this aspect of the present invention also includes a recombinant cell comprising a host cell which is transformed by the aforesaid polynucleotide or vector which contains such a polynucleotide. Preferably said host cell is a prokaryotic cell and more preferably said host cell is *E. coli* or a Bacillus strain. However, said host cell may also be a eukaryotic cell, preferably a yeast cell or a fungal cell.

Finally this aspect of the present invention also comprises a process for the preparation of geranylgeranyl pyrophosphate by culturing said recombinant cell of the invention in the presence of farnesyl pyrophosphate and isopentyl pyrophosphate in a culture medium under suitable culture conditions whereby said GGPP synthase is expressed by said cell and catalyzes the condensation of farnesyl pyrophosphate and isopentyl pyrophosphate to geranylgeranyl pyrophosphate, and isolating the geranylgeranyl pyrophosphate from such cells or the culture medium.

A further aspect of the present invention is the prephytoene synthase of Flavobacterium sp. R1534 and a polynucleotide comprising a DNA sequence which encodes said prephytoene synthase of Flavobacterium sp. R1534 (crtB), said synthase and polynucleotide being substantially free of other proteins and polynucleotides, respectively, of Flavobacterium sp. R1534. Also encompassed by this aspect of the present invention is a polynucleotide comprising a DNA sequence which is substantially homologous to said DNA sequence. Said prephytoene synthase catalyzes the condensation of two geranylgeranyl pyrophosphates to the carotenoid, prephytoene, and then catalyzes the rearrangement of the cyclopropyl ring of prephytoene to produce phytoene. The preferred prephytoene synthase has the amino acid sequence of FIG. 9 [SEQ ID NO: 3], and the preferred DNA sequence is one which encodes said amino acid sequence. The especially preferred DNA sequence is bases 4316–3405 shown in FIG. 7 [SEQ ID NO: 4].

This aspect of the present invention also includes a vector comprising the aforesaid polynucleotide, preferably in the form of an expression vector. Furthermore this aspect of the present invention also includes a recombinant cell comprising a host cell which is transformed by the aforesaid polynucleotide or vector which contains such a polynucleotide. Preferably said host cell is a prokaryotic cell and more preferably said host cell is *E. coli* or a Bacillus strain. However, said host cell may also be a eukaryotic cell, preferably a yeast cell or a fungal cell.

Finally this aspect of the present invention also comprises a process for the preparation of phytoene by culturing said recombinant cell of the invention in the presence of geranylgeranyl pyrophosphate in a culture medium under suitable culture conditions whereby said prephytoene synthase is expressed by said cell and catalyzes the condensation of two geranylgeranyl pyrophosphates to the carotenoid, prephytoene, and then catalyzes the rearrangement of the cyclopropyl ring of said prephytoene to produce phytoene, and isolating the phytoene from such cells or the culture medium.

A further aspect of the present invention is the phytoene desaturase of Flavobacterium sp. R1534 and a polynucleotide comprising a DNA sequence which encodes said phytoene desaturase of Flavobacterium sp. R1534 (crtI), said desaturase and polynucleotide being substantially free of other proteins and polynucleotides, respectively, of Flavobacterium sp. R1534. Also encompassed by this aspect of the present invention is a polynucleotide comprising a DNA sequence which is substantially homologous to said DNA sequence. Said phytoene desaturase catalyzes the desaturation of phytoene in four steps to obtain lycopene. The preferred prephytoene desaturase has the amino acid sequence of FIG. 10 [SEQ ID NO: 5], and the preferred DNA sequence is one which encodes said amino acid sequence. The especially preferred DNA sequence is bases 4313–5797 shown in FIG. 7 [SEQ ID NO: 6].

This aspect of the present invention also includes a vector comprising the aforesaid polynucleotide, preferably in the form of an expression vector. Furthermore this aspect of the present invention also includes a recombinant cell comprising a host cell which is transformed by the aforesaid polynucleotide or vector which contains such a polynucleotide. Preferably said host cell is a prokaryotic cell and more preferably said host cell is *E. coli* or a Bacillus strain. However, said host cell may also be a eukaryotic cell, preferably a yeast cell or a fungal cell.

Finally this aspect of the present invention also comprises a process for the preparation of lycopene by culturing said cell of the invention in the presence of phytoene in a culture medium under suitable culture conditions whereby said phytoene desaturase is expressed by said cell and catalyzes the desaturation of phytoene in four steps to obtain lycopene, and isolating the lycopene from such cells or the culture medium.

A still further aspect of the present invention is the lycopene cyclase of Flavobacterium sp. R1534 and a polynucleotide comprising a DNA sequence which encodes the lycopene cyclase of Flavobacterium sp. R1534 (crtY), said cyclase and polynucleotide being substantially free of other proteins and polynucleotides, respectively, of Flavobacterium sp. R1534. Also encompassed by this aspect of the present invention is a polynucleotide comprising a DNA sequence which is substantially homologous to said DNA sequence. Said lycopene cyclase catalyzes the closure of rings at both ends of lycopene to produce β-carotene. The preferred lycopene cyclase has the amino acid sequence of FIG. 11 [SEQ ID NO: 7], and the preferred DNA sequence is one which encodes said amino acid sequence. The especially preferred DNA sequence is bases 5794–6942 shown in FIG. 7 [SEQ ID NO: 8].

This aspect of the present invention also includes a vector comprising the aforesaid polynucleotide, preferably in the form of an expression vector. Furthermore this aspect of the present invention also includes a recombinant cell comprising a host cell which is transformed by the aforesaid polynucleotide or vector which contains such a polynucleotide. Preferably said host cell is a prokaryotic cell and more preferably said host cell is *E. coli* or a Bacillus strain. However, said host cell may also be a eukaryotic cell, preferably a yeast cell or a fungal cell.

Finally this aspect of the present invention also comprises a process for the preparation of β-carotene by culturing said recombinant cell of the invention in the presence of lycopene in a culture medium under suitable culture conditions whereby said lycopene cyclase is expressed by said cell and catalyzes the closure of rings at both ends of lycopene to produce β-carotene, and isolating the β-carotene from such cells or the culture medium.

A still further aspect of the present invention is the β-carotene hydroxylase of Flavobacterium sp. R1534 and a polynucleotide comprising a DNA sequence which encodes said β-carotene hydroxylase of Flavobacterium sp. R1534 (crtZ), said hydroxylase and polynucleotide being substantially free of other proteins and polynucleotides, respectively, of Flavobacterium sp. R1534. Also encompassed by this aspect of the present invention is a polynucleotide comprising a DNA sequence which is substantially homologous to said DNA sequence. Said β-carotene hydroxylase catalyzes the hydroxylation of β-carotene to produce the xanthophyll, zeaxanthin. The preferred β-carotene hydroxylase has the amino acid sequence of FIG. 12 [SEQ ID NO: 9], and the preferred DNA sequence is one which encodes said amino acid sequence. The especially preferred DNA sequence is a DNA sequence comprising bases 6939–7448 shown in FIG. 7 [SEQ ID NO: 10].

This aspect of the present invention also includes a vector comprising the aforesaid polynucleotide, preferably in the form of an expression vector. Furthermore this aspect of the present invention also includes a recombinant cell comprising a host cell which is transformed by the aforesaid polynucleotide or vector which contains such a DNA sequence. Preferably said host cell is a prokaryotic cell and more preferably said host cell is *E. coli* or a Bacillus strain. However, said host cell may also be a eukaryotic cell, preferably a yeast cell or a fungal cell.

Finally this aspect of the present invention also comprises a process for the preparation of zeaxanthin by culturing said recombinant cell of the invention in the presence of β-carotene in a culture medium under suitable culture conditions whereby said β-carotene hydroxylase is expressed by said cell and catalyzes the hydroxylation of β-carotene to produce the xanthophyll, zeaxanthin, and isolating the zeaxanthin from such cells or the culture medium. It is contemplated, and in fact preferred, that the aforementioned DNA sequences, crtE, crtB, crtI crtY and crtZ, which terms refer to the above-described genes of Flavobacterium sp. R1534 encompassed by the invention herein described, are incorporated into a polynucleotide of the invention whereby two or more of said DNA sequences which encode enzymes catalyzing contiguious steps in the process shown in FIG. 1 are contained in said polynucleotide, said polynucleotide being substantially free of other polynucleotides of Flavobacterium sp. R1534. Examples of preferred polynucleotides which encode enzymes which catalyze such contiguous steps are polynucleotides which comprise crtE and crtB (conversion of farnesyl pyrophosphate and isopentyl pyrophosphate to phytoene), crtE, crtB, and crtI (conversion of farnesyl pyrophosphate and isopentyl pyrophosphate to lycopene), crtB and crtI (conversion of geranylgeranyl pyrophosphate to lycopene) and the like.

The present invention also comprises a vector comprising a polynucleotide of the invention which contains said DNA sequences, preferably in the form of an expression vector. Furthermore the present invention also comprises a recombinant cell comprising a host cell which is transformed by a polynucleotide of the invention or vector which contains such a polynucleotide. Preferably said host cell is a prokaryotic cell and more preferably said host cell is *E. coli* or a Bacillus strain. However, said host cell may also be a eukaryotic cell, preferably a yeast cell or a fungal cell.

Finally the present invention also comprises a process for the preparation of a desired carotenoid by culturing a recombinant cell of the invention in the presence of a starting material in a culture medium under suitable culture conditions and isolating the desired carotenoid from such cells or the culture medium wherein the cell utilizes the polynucleotide of the invention which contains said DNA sequences to express the enzymes which catalyze the reactions necessary to produce the desired carotenoid from the starting material. Where an enzyme catalyzes two sequential steps and it is preferred to produce the product of the second step, a higher copy number of the DNA sequence encoding the enzyme may be used to further production of the product of the second of the two steps in comparison to the first product. The present invention further comprises a process for the preparation of a food or feed composition which process comprises mixing a nutritionally effective amount of the carotenoid isolated from the aforementioned recombinant cells or culture medium with said food or feed.

One preferred embodiment of the present invention is a polynucleotide which comprises the following DNA sequences: crtE or a DNA sequence which is substantially homologous thereto, crtB or a DNA sequence which is substantially homologous thereto, and crtI or a sequence which is substantially homologous thereto, said polynucleotide being substantially free of other polynucleotides of Flavobacterium sp. R1534. This polynucleotide encodes enzymes which catalyze the conversion of farnesyl pyrophosphate and isopentyl pyrophosphate to lycopene. It is particularly preferred that this embodiment of the invention is a polynucleotide which contains crtE, crtB, and crtI.

It is especially preferred that this polynucleotide of the invention comprises DNA sequences which encode the amino acid sequences of FIGS. 8, 9 and 10, and it is most preferred that this polynucleotide of the invention contain as the three DNA sequences crtE, crtB and crtI, bases 521–3408, 4316–3405 and 4313–5797, respectively, shown in FIG. 7.

This embodiment of the present invention also comprises a vector, recombinant cell, process of making a carotenoid and process of making a food or feed stuff containing a carotenoid, as described hereinbefore, wherein the polynucleotide is a polynucleotide of this embodiment and the carotenoid is lycopene.

Another preferred embodiment of the present invention is a polynucleotide comprising the following DNA sequences: crtE or a DNA sequence which is substantially homologous thereto, crtB or a DNA sequence which is substantially homologous thereto, crtI or a DNA sequence which is substantially homologous thereto, and crtY or a DNA sequence which is substantially homologous thereto, said polynucleotide being substantially free of other polynucleotides of Flavobacterium sp. R1534. This polynucleotide encodes enzymes which catalyze the conversion of farnesyl pyrophosphate and isopentyl pyrophosphate to β-carotene. It is especially preferred that this embodiment of the invention is a polynucleotide which contains the following DNA sequences: crtE, crtB, crtI, and crtY.

It is especially preferred that this polynucleotide of the invention comprises DNA sequences which encode the amino acid sequences of FIGS. 8, 9, 10 and 11, and it is most preferred that this polynucleotide of the invention contain as the four DNA sequences crtE, crtB, crtI and crtY, bases 2521–3408, 4316–3405, 4313–5797 and 5794–6942, respectively, shown in FIG. 7.

This embodiment of the present invention also comprises a vector, recombinant cell, process of making a carotenoid and process of making a food or feed stuff containing the carotenoid, as described hereinbefore, wherein the polynucleotide is a polynucleotide of this embodiment and the carotenoid is β-carotene.

Further, the polynucleotide of the present embodiment which contains crtE, crtB, crtI and crtY, or corresponding DNA sequences which are substantially homologous, may additionally contain a DNA sequence which encodes the β-carotene β4-oxygenase of Alcaligenes strain PC-1 (crt W) [Misawa, supra] or a DNA sequence which is substantially homologous to said β-carotene β4-oxygenase. Because the crtW subsequence encodes an enzyme which catalyzes the conversion of β-carotene to echinenone, this DNA sequence encodes enzymes which catalyze the conversion of farnesyl pyrophosphate and isopentyl pyrophosphate to echinenone, and with the further catalysis of echinenone by the enzyme encoded by crtW, to cantaxanthin. Such a polynucleotide preferably contains crtE, crtB, crtI, crtY and crt W. It is most preferred that this polynucleotide of the invention contain as the four subsequences crtE, crtB, crtI and crtY, bases 2521–3408, 4316–3405, 4313–5797 and 5794–6942, respectively, shown in FIG. 7.

This embodiment of the present invention in which the polynucleotide contains crtE, crtB, crtI, crtY and crt W, or DNA sequences which are substantially homologous thereto, also comprises a vector, recombinant cell, process of making a carotenoid and process of making a food or feed stuff containing the carotenoid, as described hereinbefore, wherein the polynucleotide is the polynucleotide of this embodiment and the carotenoid is echinenone and also cantaxanthin.

It is also contemplated that, instead of being transformed by one expression vector comprising crtE, crtB, crtI, crtY and crt W, a recombinant cell of the invention which expresses the aforesaid enzymes which catalyze the conversion of farnesyl pyrophosphate and isopentyl pyrophosphate to echinenone, and with the further catalysis of echinenone by the enzyme encoded by crtW, to cantaxanthin, may be obtained by transforming a host cell with two expression vectors, one of which comprises crte, crtB, crtI, crtY, but not crtW, and the second of which comprises crtW. The preferred expression vector which contains a polynucleotide comprising crtE, crtB, crtI and crtY is as described above.

Another preferred embodiment of the present invention is a polynucleotide comprising the following DNA sequences: crtE or a DNA sequence which is substantially homologous thereto, crtB or a DNA sequence which is substantially homologous thereto, crtI or a DNA sequence which is substantially homologous thereto, crtY or a DNA sequence which is substantially homologous thereto, and crtZ or a DNA sequence which is substantially homologous thereto, said polynucleotide being substantially free of other polynucleotides of Flavobacterium sp. R1534. This polynucleotide encodes enzymes which catalyze the conversion of farnesyl pyrophosphate and isopentyl pyrophosphate to cryptoxanthin, and with further catalysis of cryptoxanthin by the enzyme encoded by crtZ, to zeaxanthin. Such a polynucleotide preferably contains crtE, crtB, crtI, crtY and crt Z. It is most preferred that this polynucleotide of the invention contain as the five subsequences crtE, crtB, crtI, crtY and crtZ, bases 2521–3408, 4316–3405, 4313–5797, 5794–6942 and 6939–7448, respectively, shown in FIG. 7.

This embodiment of the present invention in which the polynucleotide contains crtE, crtB, crtI, crtY and crt Z, or DNA sequences which are substantially homologous thereto, also comprises a vector, recombinant cell, process of making a carotenoid and process of making a food or feed stuff containing the carotenoid, as described hereinbefore, wherein the polynucleotide is the polynucleotide of this embodiment and the carotenoid is cryptoxanthin and also zeaxanthin.

Further, the polynucleotide of the present embodiment which contains crtE, crtB, crtI, crtY and crtZ, or corresponding DNA sequences which are substantially homologous, may additionally contain a DNA sequence which encodes the β-carotene β4-oxygenase of Alcaligenes strain PC-1 (crt W) [Misawa, supra] or a DNA sequence which is substantially homologous to said β-carotene β4-oxygenase. Because the crtW DNA sequence encodes a enzyme which catalyzes the conversion of zeaxanthin to adonixanthin, this polynucleotide encodes enzymes which catalyze the conversion of farnesyl pyrophosphate and isopentyl pyrophosphate to adonixanthin, and with the further catalysis of adonixanthin by the enzyme encoded by crtW, to astaxanthin. Such a polynucleotide preferably contains crtE, crtB, crtI, crtY, crtZ and crt W. It is most preferred that this polynucleotide of the invention contain as the five subsequences crtE, crtB, crtI, crtY and crtZ, bases 2521–3408, 4316–3405, 4313–5797, 5794–6942 and 6939–7448, respectively, shown in FIG. 7.

This embodiment of the present invention in which the polynucleotide contains crtE, crtB, crtI, crtY, crtZ and crt W, or DNA sequences which are substantially homologous thereto, also comprises a vector, recombinant cell, process of making a carotenoid and process of making a food or feed stuff containing the carotenoid, as described hereinbefore, wherein the polynucleotide is the polynucleotide of this embodiment and the carotenoid is adonixanthin and also astaxanthin.

It is also contemplated that, instead of being transformed by one expression vector comprising crtE, crtB, crtI, crty, crtZ and crt W, a recombinant cell of the invention which expresses the aforesaid enzymes which catalyze the conversion of farnesyl pyrophosphate and isopentyl pyrophosphate to adonixanthin, and with the further catalysis of adonixanthin by the enzyme encoded by crtW, to astaxanthin, may be obtained by transforming a host cell with two expression vectors, one of which comprises crtE, crtB, crtI, crtY, and crtZ, but not crtW, and the second of which comprises crtW. The preferred expression vector which contains a polynucleotide comprising crtE, crtB, crtI, crtY, and crtZ is as described above.

The expression "a DNA sequence which is substantially homologous" refers with respect to the crtE encoding DNA sequence to a DNA sequence which encodes an amino acid sequence which shows more than 45%, preferably more than 60% and more preferably more than 75% and most preferably more than 90% identical amino acids when compared to the amino acid sequence of crtE of Flavobacterium sp. 1534 and is the amino acid sequence of a polypeptide which shows the same type of enzymatic activity as the enzyme encoded by crtE of Flavobacterium sp. 1534. In analogy with respect to crtB this means more than 60%, preferably more than 70%, more preferably more than 80% and most preferably more than 90%; with respect to crtI this means more than 70%, preferably more than 80% and most preferably more than 90%; with respect to crtY this means 55%, preferably 70%, more preferably 80% and most preferably 90%; with respect to crtZ this means more than 60%, preferably 70%, more preferably 80% and most preferably 90%; with respect to crt W this also means more than 60%, preferably 70%, more preferably 80% and most preferably 90%. Sequences which are substantially homologous to crtW are known, e.g., in form of the β-carotene β4-oxygenase of Agrobacterium aurantiacum or the green algae Haematococous pluvialis (bkt).

The expression "said polynucleotide being substantially free of other polynucleotides of Flavobacterium sp. R1534" is meant to preclude the present invention from encompassing the polynucleotides as they exist in Flavobacterium sp. R1534, itself. The polynucleotides herein described which are combinations of two or more DNA sequences of Flavobacterium sp. R1534 are also "substantially free of other polynucleotides of Flavobacterium sp. R1534" in any circumstance where a polynucleotide containing only a single such DNA sequence would be "substantially free of other polynucleotides of Flavobacterium sp. R1534."

DNA sequences in the form of genomic DNA, cDNA or synthetic DNA can be prepared as known in the art [see, e.g., Sambrook et al., *Molecular Cloning*, Cold Spring Habor Laboratory Press 1989] or, e.g., as specifically described in Examples 1, 2 or 7.

The cloning of the DNA sequences of the present invention from such genomic DNA can than be effected, e.g., by using the well known polymerase chain reaction (PCR) method. The principles of this method are outlined, e.g., in *PCR Protocols: A guide to Methods and Applications*, Academic Press, Inc. (1990). PCR is an in vitro method for producing large amounts of a specific DNA of defined length and sequence from a mixture of different DNA sequences. Thereby, PCR is based on the enzymatic amplification of the specific DNA fragment of interest which is flanked by two oligonucleotide primers which are specific for this sequence and which hybridize to the opposite strand of the target sequence. The primers are oriented with their 3' ends pointing toward each other. Repeated cycles of heat denaturation of the template, annealing of the primers to their complementary sequences and extension of the annealed primers with a DNA polymerase result in the amplification of the segment between the PCR primers. Since the extension product of each primer can serve as a template for the other, each cycle essentially doubles the amount of the DNA fragment produced in the previous cycle.

By utilizing the thermostable Taq DNA polymerase, isolated from the thermophilic bacteria *Thermus aquaticus*, it has been possible to avoid denaturation of the polymerase which had necessitated the addition of enzyme after each heat denaturation step. This development has led to the automation of PCR by a variety of simple temperature-cycling devices. In addition, the specificity of the amplification reaction is increased by allowing the use of higher temperatures for primer annealing and extension. The increased specificity improves the overall yield of amplified products by minimizing the competition by non-target fragments for enzyme and primers. In this way the specific sequence of interest is highly amplified and can be easily separated from the non-specific sequences by methods known in the art, e.g., by separation on an agarose gel, and cloned by methods known in the art using vectors as described, e.g., by Holten and Graham in *Nucleic Acid Res.* 19, 1156 (1991), Kovalic et. al. in *Nucleic Acid Res.* 19, 4560 (1991), Marchuk et al. in *Nucleic Acid Res.* 19, 1154 (1991) or Mead et al. in *Bio/Technology* 9, 657–663 (1991).

The oligonucleotide primers used in the PCR procedure can be prepared as known in the art and described, e.g., in Sambrook et al., supra. Amplified DNA sequences can then be used to screen DNA libraries by methods known in the art (Sambrook et al., supra) or as specifically described in Examples 1 and 2. Once complete DNA sequences of the present invention have been obtained, they can be used as a guideline to define new PCR primers for the cloning of substantially homologous DNA sequences from other sources.

In addition, the DNA sequences of the invention and such homologous DNA sequences can be integrated into expression vectors by methods known in the art and described, e.g., in Sambrook et al., supra to express or overexpress the encoded polypeptide(s) in appropriate host systems. The expression vector into which the polynucleotides of the invention are integrated is not critical. Conventional expression vectors may be selected based upon the size of the polynucleotide of the invention to be inserted into the vector and the host cell to be transformed by the vector. Such conventional expression vectors contain a regulatory sequence for the synthesis of mRNA derived from the polynucleotide of the invention being expressed and possible marker genes. Conventional regulatory sequences generally contain, but are not limited to, one or more of the following: a signal sequence, an origin of replication, one or more marker genes, an enhancer element, a promoter, and a transcription termination sequence.

Suitable vectors which can be used for expression in *E. coli* are known, e.g., the vectors described by Sambrook et al., supra or by Fiers et al. in "Procd. 8th Int. Biotechnology Symposium" [Soc. Franc. de Microbiol., Paris (Durand et al., eds.), pp. 680–697 (1988)] or by Bujard et al. in *Methods in Enzymology*, eds. Wu and Grossmann, Academic Press, Inc. Vol. 155, 416–433 (1987) and Stüber et al. in *Immunological Methods*, eds. Lefkovits and Pernis, Academic Press, Inc., Vol. IV, 121–152 (1990). Vectors which could be used for expression in Bacilli are known in the art and described, e.g., in EP 405 370, EP 635 572, *Proc. Nat. Acad. Sci. USA* 81, 439 (1984) by Yansura and Henner, *Meth. Enzym.* 185, 199–228 (1990) or EP 207 459. Vectors which can be used for expression in fungi are known in the art and described, e.g., in EP 420 358. Vectors which can be used for expression in yeast are known in the art and are described, e.g., in EP 183 070, EP 183 071, EP 248 227 and EP 263 311.

The polynucleotides of the invention themselves, or expression vectors containing them, can be used to transform suitable host cells to get overexpression of the encoded enzyme or enzymes. The transformation of host cells to obtain a cell of the invention may be performed by any conventional means. Appropriate host cells are for example bacteria, e.g., *E. coli*, Bacilli as, e.g., *Bacillus subtilis* or Flavobacter strains. *E. coli* which could be used are *E. coli* K12 strains, e.g., M15 [described as DZ 291 by Villarejo et al. in *J. Bacteriol.* 120, 466–474 (1974)], HB 101 [ATCC No. 33694] or *E. coli* SG13009 [Gottesman et al., *J. Bacteriol.* 148, 265–273 (1981)]. Suitable eukaryotic host cells are, for example, fungi, like Aspergilli, e.g., *Aspergillus niger* [ATCC 9142] or yeasts, like Saccharomyces, e.g., *Saccharomyces cerevisiae* or Pichia, like pastoris, all available from ATCC.

Once the polynucleotides of the invention have been expressed in an appropriate host cell in a suitable medium, thereby causing the catalysis of the starting materials to the desired carotenoids, the carotenoids can be isolated either from the medium, in the case they are secreted into the medium, or from the host organism and, if necessary separated from other carotenoids that may be present in case one specific carotenoid is desired, by methods known in the art (see, e.g., *Carotenoids Vol IA: Isolation and Analysis*, G. Britton, S. Liaaen-Jensen, H. Pfander; 1995, Birkhäuser Verlag, Basel)

The carotenoids produced in accordance with the present invention can be used in a process for the preparation of food or feeds. A man skilled in the art is familiar with such processes. Such compound foods or feeds can further comprise additives or components generally used for such purpose and known in the state of the art.

After the invention has been described in general hereinbefore, the following examples are intended to illustrate details of the invention, without thereby limiting it in any matter.

EXAMPLE 1

Materials and General Methods Used

Bacterial strains and plasmids: Flavobacterium sp. R1534 WT was the DNA source for the genes cloned. Partial genomic libraries of Flavobacterium sp. R1534 WT DNA were constructed into the pBluescriptII+(KS) or (SK) vector (Stratagene, La Jolla, USA) and transformed into *E. coli* XL-1 blue (Stratagene) or JM109.

Media and growth conditions: Transformed *E. coli* were grown in Luria broth (LB) at 37° C. with 100 mg Ampicillin (Amp)/ml for selection. Flavobacterium sp. R1534 WT was grown at 27° C. in medium containing 1% glucose, 1% tryptone (Difco Laboratories), 1% yeast extract (Difco), 0.5% $MgSO_4$ $7H_2O$ and 3% NaCl.

Colony screening: Screening of the *E. coli* transformants was done by PCR basically according to the method described by Zon et al. [Zon et al., *BioTechniques*, 696–698 (1989)] using the following primers:

Primer #7: 5'-CCTGGATGACGTGCTGGAATATTCC-3' [SEQ ID NO: 12]

Primer #8: 5'-CAAGGCCCAGATCGCAGGCG-3' [SEQ ID NO: 13]

Genomic DNA: A 50 ml overnight culture of Flavobacterium sp. R1534 was centrifuged at 10,000 g for 10 minutes. The pellet was washed briefly with 10 ml of lysis buffer (50 mM EDTA, 0.1M NaCl pH7.5), resuspended in 4 ml of the same buffer supplemented with 10 mg of lysozyme and incubated at 37° C. for 15 minutes. After addition of 0.3 ml of N-Lauroyl sarcosine (20%) the incubation at 37° C. was continued for another 15 minutes before the extraction of the DNA with phenol, phenol/chloroform and chloroform. The DNA was ethanol precipitated at room temperature for 20 minutes in the presence of 0.3 M sodium acetate (pH 5.2), followed by centrifugation at 10,000 g for 15 minutes. The pellet was rinsed with 70% ethanol, dried and resuspended in 1 ml of TE (10 mM Tris, 1 mM EDTA, pH 8.0).

All genomic DNA used in the southern blot analysis and cloning experiments was dialysed against $H_2O$ for 48 hours, using collodium bags (Sartorius, Germany), ethanol precipitated in the presence of 0.3 M sodium acetate and resuspended in $H_2O$.

Probe labelling: DNA probes were labeled with (a-$^{32}$P) dGTP (Amersham) by random-priming according to [Sambrook et al., s.a.].

Figure 6:
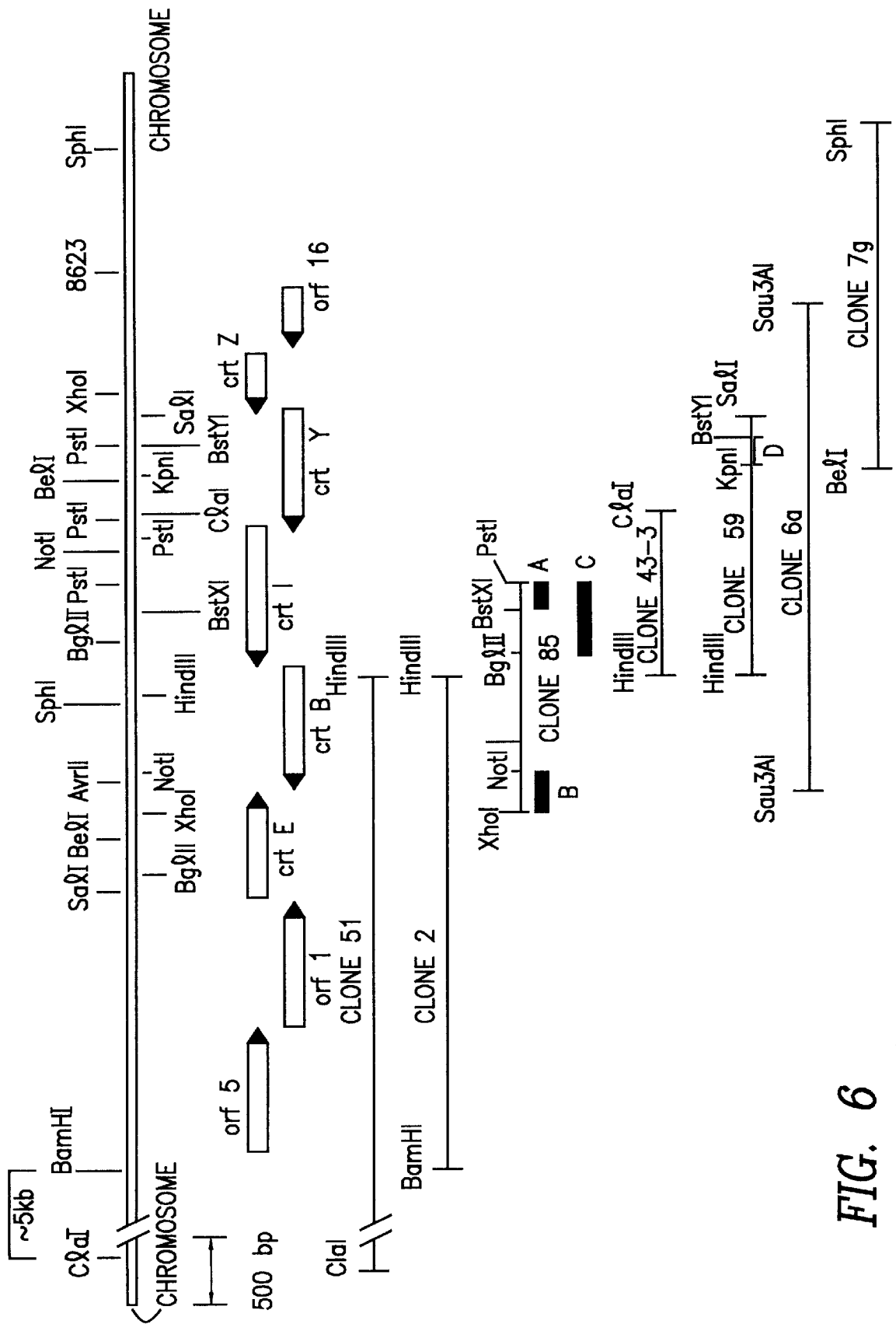
FIG. 6: Physical map of the organization of the carotenoid biosynthesis cluster in Flavobacterium sp. R1534, deduced from the genomic clones obtained. The location of the probes used for the screening are shown as bars on the respective clones.

Probes used to screen the mini-libraries: Probe 46F is a 119 bp fragment obtained by PCR using primer #7 and #8 and Flavobacterium sp. R1534 genomic DNA as template. This probe was proposed to be a fragment of the Flavobacterium sp. R1534 phytoene synthase (crtB) gene, since it shows significant homology to the phytoene synthase genes from other species (e.g. *E. uredovora, E. hericola*). Probe A is a BstXI-PstI fragment of 184 bp originating from the right arm of the insert of clone 85. Probe B is a 397 bp XhoI-NotI fragment obtained from the left end of the insert of clone 85. Probe C is a 536 bp BglII-PstI fragment from the right end of the insert of clone 85. Probe D is a 376 bp KpnI-BstYI fragment isolated from the insert of clone 59. The localization of the individual probes is shown in FIG. 6.

Oligonucleotide synthesis: The oligonucleotides used for PCR reactions or for sequencing were synthesized with an Applied Biosystems 392 DNA synthesizer.

Southern blot analysis: For hybridization experiments Flavobacterium sp. R1534 genomic DNA (3 mg) was digested with the appropiate restriction enzymes and electrophoresed on a 0.75% agarose gel. The transfer to Zeta-Probe blotting membranes (BIO-RAD), was done as described [Sourthern, E. M., *J. Mol. Biol.* 98, 503 (1975)]. Prehybridization and hybridization was in 7% SDS, 1% BSA (fraction V; Boehringer), 0.5M $Na_2HPO_4$, pH 7.2 at 65° C. After hybridization the membranes were washed twice for 5 minutes in 2× SSC, 1% SDS at room temperature and twice for 15 minutes in 0.1% SSC, 0.1% SDS at 65° C.

DNA sequence analysis: The sequence was determined by the dideoxy chain termination technique [Sanger et al., *Proc. Natl. Acad. Sci. USA* 74, 5463–5467 (1977)] using the Sequenase Kit (United States Biochemical). Both strands were completely sequenced and the sequence analyzed using the GCG sequence analysis software package (Version 8.0) by Genetics Computer, Inc. [Devereux et al., *Nucleic Acids. Res.* 12, 387–395 (1984)].

Analysis of carotenoids: *E. coli* XL-1 or JM109 cells (200–400 ml) carrying different plasmid constructs were grown for the times indicated in the text, usually 24 to 60 hours, in LB suplemented with 100 µg Ampicillin/ml, in shake flasks at 37° C. and 220 rpm.

The carotenoids present in the microorganisms were extracted with an adequate volume of acetone using a rotation homogenizer (Polytron, Kinematica AG, CH-Luzern). The homogenate was the filtered through the sintered glass of a suction filter into a round bottom flask. The filtrate was evaporated by means of a rotation evaporator at 50° C. using a water-jet vacuum. For the zeaxanthin detection the residue was dissolved in n-hexane/acetone (86:14) before analysis with a normalphase HPLC as described in [Weber, S. in *Analytical Methods for Vitamins and Carotenoids in Feed*, Keller, H. E., Editor, 83–85 (1988)]. For the detection of β-carotene and lycopene the evaporated extract was dissolved in n-hexane/acetone (99:1) and analysed by HPLC as described in [Hengartner et al., *Helv. Chim. Acta* 75, 1848–1865 (1992)].

EXAMPLE 2

Cloning of the Flavobacterium sp. R1534 Carotenoid Biosynthetic Genes.

Figure 2:
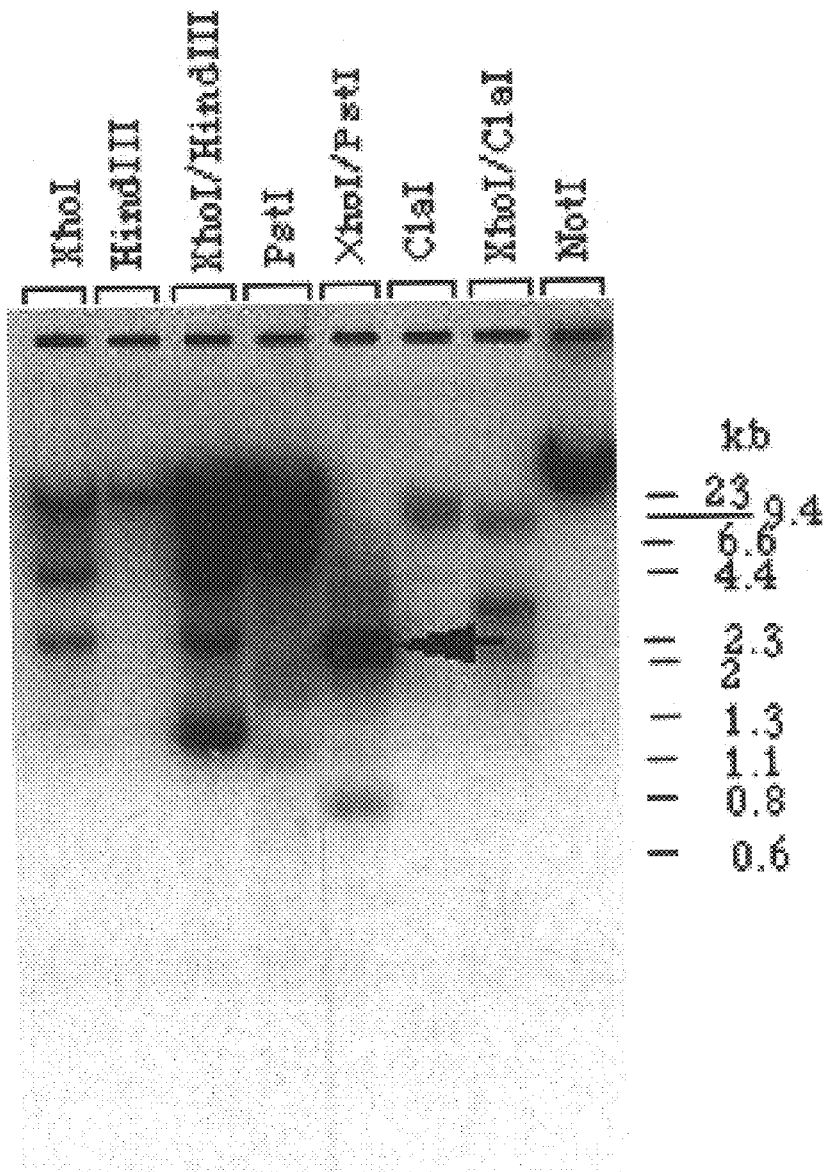
FIG. 2: Southern blot of genomic Flavobacterium sp. R1534 DNA digested with the restriction enzymes shown on top of each lane and hybridized with Probe 46F. The arrow indicated the isolated 2.4 kb XhoI/PstI fragment.
Figures 3A, 3B:
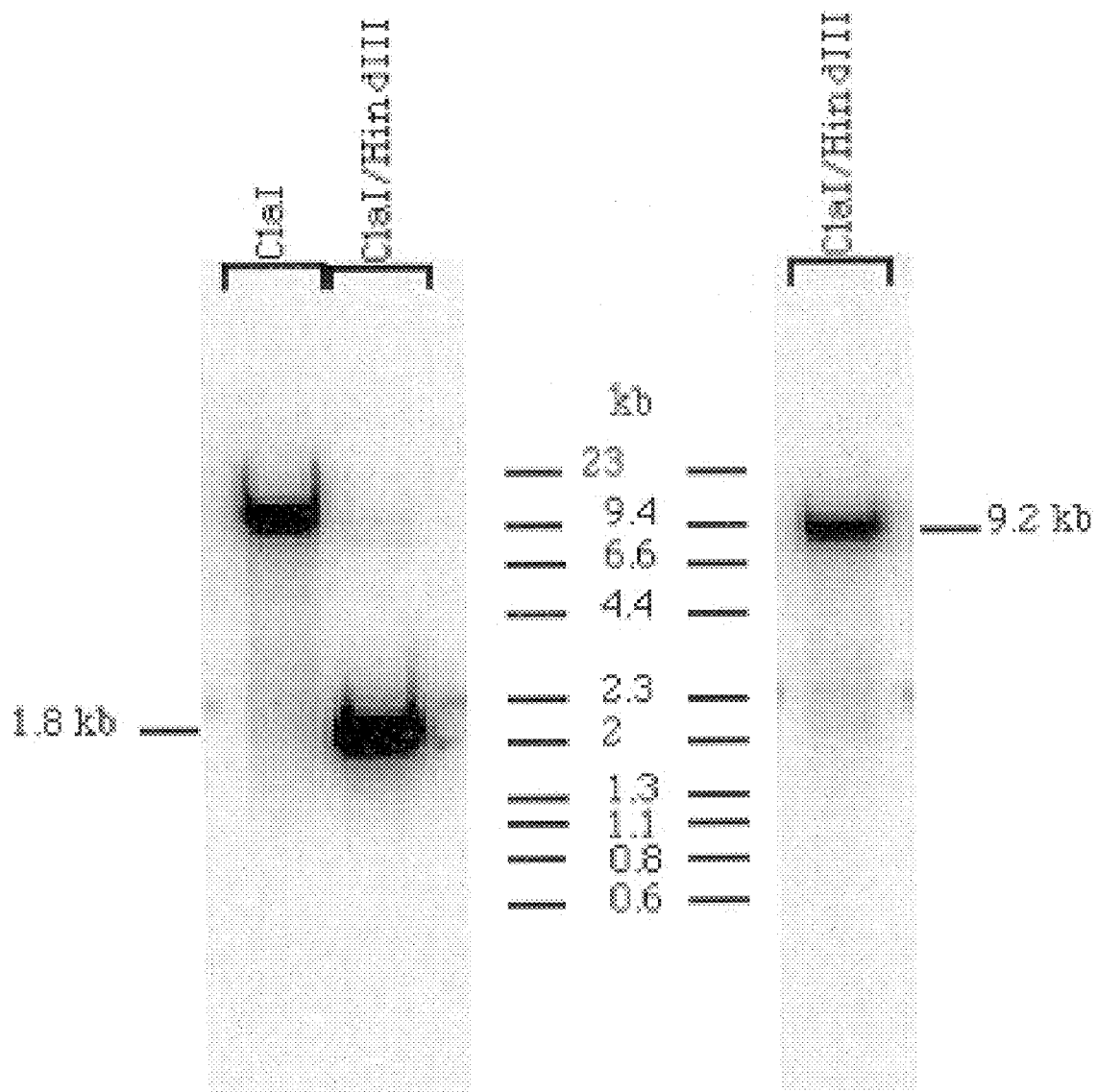
FIG. 3: Southern blot of genomic Flavobacterium sp. R1534 DNA digested with ClaI or double digested with ClaI and HindIII. Blots shown in Panel A and B were hybridized to probe A or probe B, respectively (see examples). Both ClaI/HindIII fragments of 1.8 kb and 9.2 kb are indicated.

To identify and isolate DNA fragments carrying the genes of the carotenoid biosynthesis pathway, we used the DNA fragment 46F (see methods) to probe a Southern Blot carrying chromosomal DNA of Flavobacterium sp. R1534 digested with different restriction enzymes FIG. 2. The 2.4 kb XhoI/PstI fragment hybridizing to the probe seemed the most appropiate one to start with. Genomic Flavobacterium sp. R1534 DNA was digested with XhoI/PstI and run on a 1% agarose gel. According to a comigrating DNA marker, the region of about 2.4 kb was cut out of the gel and the DNA isolated. A XhoI/PstI mini library of Flavobacterium sp. R1534 genomic DNA was constructed into XhoI-PstI sites of pBluescriptIISK(+). One hundred *E. coli* XL1 transformants were subsequentely screened by PCR with primer #7 and primer #8, the same primers previously used to obtain the 119 bp fragment (46F). One positive transformant, named clone 85, was found. Sequencing of the insert revealed sequences not only homologous to the phytoene synthase (crtB) but also to the phytoene desaturase (crtI) of both Erwinia species herbicola and uredovora. Left and right hand genomic sequences of clone 85 were obtained by the same approach using probe A and probe B. Flavobacterium sp. R1534 genomic DNA was double digested with ClaI and Hind III and subjected to Southern analysis with probe A and probe B. With probe A a ClaI/HindIII fragment of aprox. 1.8 kb was identified (FIG. 3A), isolated and subcloned into the ClaI/HindIII sites of pBluescriptIIKS(+). Screening of the *E. coli* XL1 transformants with probe A gave 6 positive clones. The insert of one of these positives, clone 43-3, was sequenced and showed homology to the N-terminus of crtI genes and to the C-terminus of crtY genes of both Erwinia species mentioned above. With probe B an approx. 9.2 kb ClaI/HindIII fragment was detected (FIG. 3B), isolated and subcloned into pBluescriptIIKS(+).

A screening of the transformants gave one positive, clone 51. Sequencing of the 5' and 3' of the insert, revealed that only the region close to the HindIII site showed relevant homology to genes of the carotenoid biosynthesis of the Erwinia species mentioned above (e.g. crtB gene and crtE gene). The sequence around the ClaI site showed no homology to known genes of the carotenoid biosynthesis pathway. Based on this information and to facilitate further sequencing and construction work, the 4.2 kb BamHI/HindIII fragment of clone 51 was subcloned into the respective sites of pBluescriptIIKS(+) resulting in clone 2. Sequencing of the insert of this clone confirmed the presence of genes homologous to Erwinia sp. crtB and crtE genes. These genes were located within 1.8 kb from the HindIII site. The remaining 2.4 kb of this insert had no homology to known carotenoid biosynthesis genes.

Figure 4:
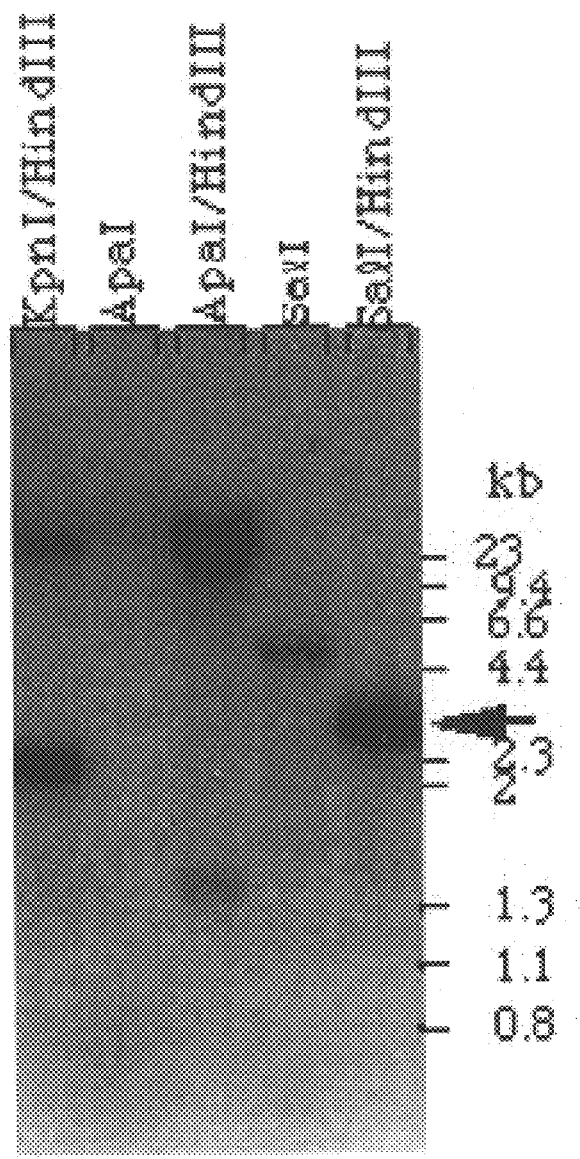
FIG. 4: Southern blot of genomic Flavobacterium sp. R1534 DNA digested with the restriction enzymes shown on top of each lane and hybridized to probe C. The isolated 2.8 kb SalI/HindIII fragment is shown by the arrow.

Additional genomic sequences downstream of the ClaI site were detected using probe C to hybridize to Flavobacterium sp. R1534 genomic DNA digested with different restriction enzymes (see FIG. 4).

Figure 5:
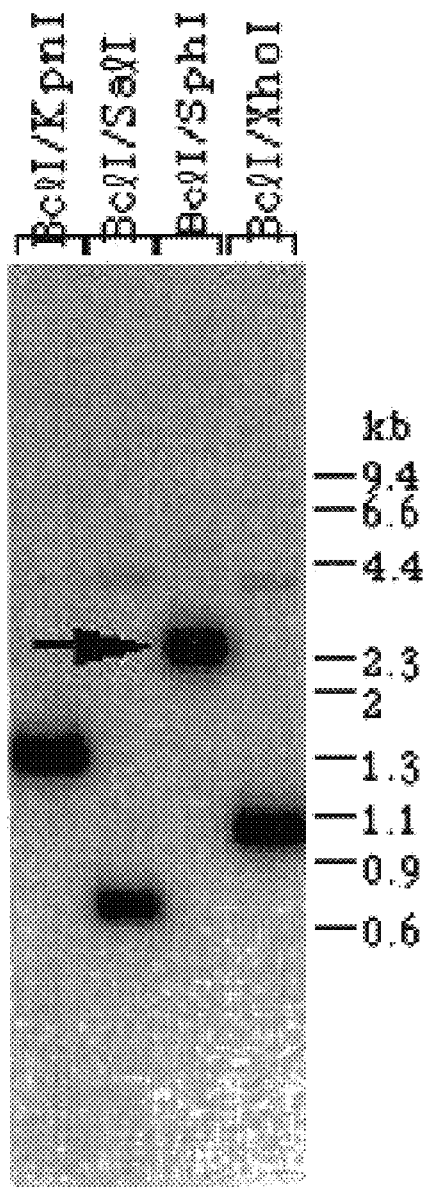
FIG. 5: Southern blot of genomic Flavobacterium sp. R1534 DNA digested with the restriction enzymes shown on top of each lane and hybridized to probe D. The isolated BclI/SphI fragment of approx. 3 kb is shown by the arrow.

A SalI/HindIII fragment of 2.8 kb identified by Southern analysis was isolated and subcloned into the HindIII/XhoI sites of pBluescriptIIKS(+). Screening of the *E. coli* XL1 transformants with probe A gave one positive clone named clone 59. The insert of this clone confirmed the sequence of clone 43-3 and contained in addition sequences homologous to the N-terminus of the crtY gene from other known lycopene cyclases. To obtain the putative missing crtZ gene a Sau3AI partial digestion library of Flavobacterium sp. R1534 was constructed into the BamHI site of pBluescriptIIKS(+). Screening of this library with probe D gave several positive clones. One transformant designated, clone 6a, had an insert of 4.9 kb. Sequencing of the insert revealed besides the already known sequences coding for crtB, crtI and crtY also the missing crtZ gene. Clone 7g was isolated from a mini library carrying BclI/SphI fragments of R1534 (FIG. 5) and screened with probe D. The insert size of clone 7g is approx. 3 kb.

The six independent inserts of the clones described above covering approx. 14 kb of the Flavobacterium sp. R1534 genome are compiled in FIG. 6.

The determined sequence spanning from the BamHI site (position 1) to base pair 8625 is shown FIG. 7.

Putative Protein Coding Regions of the Cloned R1534 Sequence.

Computer analysis using the CodonPreference program of the GCG package, which recognizes protein coding regions by virtue of the similarity of their codon usage to a given codon frequency table, revealed eight open reading frames (ORFs) encoding putative proteins: a partial ORF from 1 to 1165 (ORF-5) coding for a polypeptide larger than 41382 Da; an ORF coding for a polypeptide with a molecular weight of 40081 Da from 1180 to 2352 (ORF-1); an ORF coding for a polypeptide with a molecular weight of 31331 Da from 2521 to 3405 (crtE); an ORF coding for a polypeptide with a molecular weight of 32615 Da from 4316 to 3408 (crtB); an ORF coding for a polypeptide with a molecular weight of 54411 Da from 5797 to 4316 (crtI); an ORF coding for a polypeptide with a molecular weight of 42368 Da from 6942 to 5797 (crtY); an ORF coding for a polypeptide with a molecular weight of 19282 Da from 7448 to 6942 (crtZ); and an ORF coding for a polypeptide with a molecular weight of 19368 Da from 8315 to 7770 (ORF-16); ORF-1 and crtE have the opposite transcriptional orientation from the others (FIG. 6). The translation start sites of the ORFs crtI, crtY and crtZ could clearly be determined based on the appropiately located sequences homologous to the Shine/Delgano (S/D) [Shine and Dalgarno, *Proc. Natl. Acad. Sci. USA* 71, 1342–1346 (1974)] consensus sequence AGG-6-9N-ATG (FIG. 10) and the homology to the N-terminal sequences of the respective enzymes of *E. hericola* and *E. uredovora*. The translation of the ORF crtB could potentially start from three closely spaced codons ATG (4316), ATG (4241) and ATG (4211). The first one, although not having the best S/D sequence of the three, gives a translation product with the highest homology to the N-terminus of the *E. herbicola* and *E. uredovora* crtB protein, and is therefore the most likely translation start site. The translation of ORF crtE could potentially start from five different start codons found within 150 bp : ATG (2389), ATG (2446), ATG (2473), ATG (2497) and ATG (2521). We believe that based on the following observations, the ATG (2521) is the most likely transcription start site of crtE: this ATG start codon is preceeded by the best consensus S/D sequence of all five putative start sites mentioned; and the putative N-terminal amino acid sequence of the protein encoded has the highest homology to the N-terminus of the crtE enzymes of *E. hericola* and *E. uredovora*;

Characteristics of the crt Translational Initiation Sites and Gene Products.

The translational start sites of the five carotenoid biosynthesis genes are shown below and the possible ribosome binding sites are underlined. The genes crtZ, crtY, crtI and crtB are grouped so tightly that the TGA stop codon of the anterior gene overlaps the ATG of the following gene. Only three of the five genes (crtI, crtY and crtZ) fit with the consensus for optimal S/D sequences. The boxed TGA sequence shows the stop condon of the anterior gene.

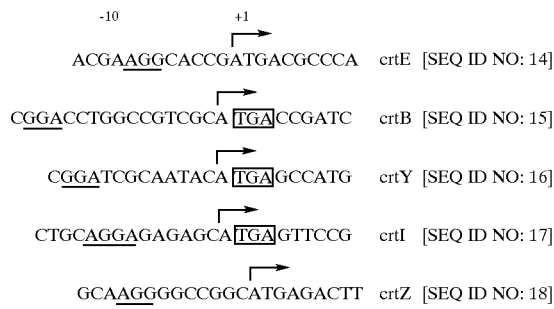

Amino Acid Sequences of Individual crt Genes of Flavobacterium sp. R1534.

All five ORFs of Flavobacterium sp. R1534 having homology to known carotenoid biosynthesis genes of other species are clustered in approx. 5.2 kb of the sequence (FIG. 7).

GGDP Synthase (crtE)

The amino acid (aa) sequence of the geranylgeranyl pyrophosphate synthase (crtE gene product) consists of 295 aa and is shown in FIG. 8. This enzyme condenses farnesyl pyrophosphate and isopentenyl pyrophosphate in a 1'–4.

Phytoene Synthase (crtB)

This enzyme catalyzes two enzymatic steps. First it condenses in a head to head reaction two geranylgeranyl pyrophosphates (C20) to the C40 carotenoid prephytoene. Second it rearanges the cyclopropylring of prephytoene to phytoene. The 303 aa encoded by the crtB gene of Flavobacterium sp. R1534 is shown in FIG. 9.

Phytoene Desaturase (crtI)

The phytoene desaturase of Flavobacterium sp. R1534 consisting of 494 aa, shown in FIG. 10, performs like the crtI enzyme of *E. hericola* and *E. uredovora*, four desaturation steps, converting the non-coloured carotenoid phytoene to the red coloured lycopene.

Lycopene Cyclase (crtY)

The crtY gene product of Flavobacterium sp. R1534 is sufficient to introduce the b-ionone rings at both sides of lycopene to obtain β-carotene. The lycopene cyclase of Flavobacterium sp. R1534 consists of 382 aa (FIG. 11).

β-carotene hydroxylase (crtZ)

The gene product of crtZ consisting of 169 aa (FIG. 12) and hydroxylates β-carotene to the xanthophyll, zeaxanthin.

Putative Enzymatic Functions of the ORF's (orf-1, orf-5 and orf-16)

The orf-1 has at the aa level over 40% identity to acetoacetyl-CoA thiolases of different organisms (e.g., *Candida tropicalis*, human, rat). This gene is therefore most likely a putative acetoacetyl-CoA thiolase (acetyl-CoA acetyltransferase), which condenses two molecules of acetyl-CoA to Acetoacetyl-CoA. Condensation of acetoacetyl-CoA with a third acetyl-CoA by the HMG-CoA synthase forms β-hydroxy-β-methylglutaryl-CoA (HMG-CoA). This compound is part of the mevalonate pathway which produces besides sterols also numerous kinds of isoprenoids with diverse cellular functions. In bacteria and plants, the isoprenoid pathway is also able to synthesize some unique products like carotenoids, growth regulators (e.g. in plants gibberellins and abcissic acid) and sencodary metabolites like phytoalexins [Riou et al., *Gene* 148, 293–297 (1994)].

The orf-5 has a low homology of approx. 30%, to the amino acid sequence of polyketide synthases from different streptomyces (e.g. *S. violaceoruber, S. cinnamonensis*). These antibiotic synthesizing enzymes (polyketide synthases), have been classified into two groups. Type-I polyketide synthases are large multifunctional proteins, whereas type-II polyketide synthases are multiprotein complexes composed of several individual proteins involved in the subreactions of the polyketide synthesis [Bibb, et al., Gene 142, 31–39 (1994)].

The putative protein encoded by the orf-16 has at the aa level an identity of 42% when compared to the soluble hydrogenase subunit of Anabaena cylindrica.

Functional Assignment of the ORF's (crtE, crtB, crtI, crtY and crtZ) to Enzymatic Activities of the Carotenoid Biosynthesis Pathway.

Figure 13:
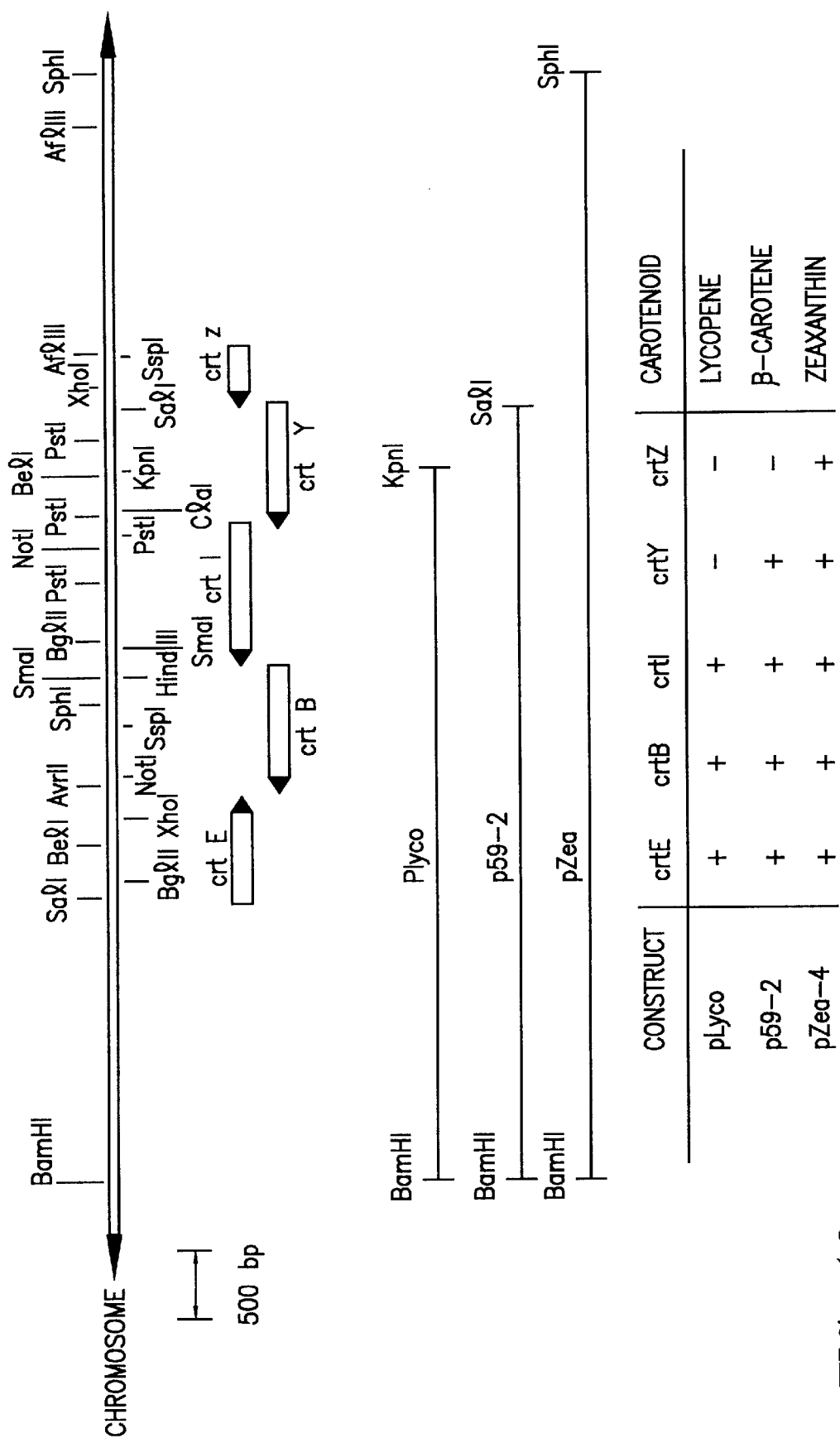
FIG. 13: Recombinant plasmids containing deletions of the Flavobacterium sp. R1534 carotenoid biosynthesis gene cluster.

The biochemical assignment of the gene products of the different ORF's were revealed by analyzing carotenoid accumulation in *E. coli* host strains that were transformed with deleted variants of the Flavobacterium sp. gene cluster and thus expressed not all of the crt genes (FIG. 13).

Three different plasmid were constructed: pLyco, p59-2 and pZea4. Plasmid p59-2 was obtained by subcloning the HindIII/BamHI fragment of clone 2 into the HindIII/BamHI sites of clone 59. p59-2 carries the ORF's of the crtE, crtB, crtI and crtY gene and should lead to the production of b-carotene. pLyco was obtained by deleting the KpnI/KpnI fragment, coding for approx. one half (N-terminus) of the crtY gene, from the p59-2 plasmid. *E. coli* cells transformed with pLyco, and therefore having a truncated non-functional crtY gene, should produce lycopene, the precursor of β-carotene. pZea4 was constructed by ligation of the AscI-SpeI fragment of p59-2, containing the crtE, crtB, crtI and most of the crtY gene with the AscI/XbaI fragment of clone 6a, containing the sequences to complete the crtY gene and the crtZ gene. pZea4 [for complete sequence see FIG. 24; nucleotides 1 to 683 result from pBluescriptIIKS(+), nucleotides 684 to 8961 from Flavobacterium R1534 WT genome, nucleotides 8962 to 11233 from pBluescriptIIKS (+)] has therefore all five ORF's of the zeaxanthin biosynthesis pathway. Plasmid pZea4 has been deposited on May 25, 1995 at the DSM-Deutsche Sammiung von Mikroorganismen und Zellkulturen GmbH (Germany) under accession No. DSM 10012. *E. coli* cells transformed with this latter plasmid should therefore produce zeaxanthin. For the detection of the carotenoid produced, transformants were grown for 48 hours in shake flasks and then subjected to carotenoid analysis as described in the methods section. FIG. 13 summarizes the different inserts of the plasmids described above, and the main carotenoid detected in the cells.

As expected the pLyco carrying *E. coli* cells produced lycopene, those carrying p59-2 produced β-carotene (all-E, 9-Z,13-Z) and the cells having the pZea4 construct produced zeaxanthin. This confirms that all the necessary genes of Flavobacterium sp. R1534 for the synthesis of zeaxanthin or their precursors (phytoene, lycopene and β-carotene) were cloned.

EXAMPLE 3

Materials and Methods Used for Expression of Carotenoid Synthesizing Enzymes Bacterial strains and plasmids: The vectors pBluescriptI-IKS (+) or (−) (Stratagene, La Jolla, USA) and pUC18 [Vieira and Messing, Gene 19, 259–268 (1982); Norrander et al., Gene 26, 101–106 (1983)] were used for cloning in different *E. coli* strains, like XL-1 blue (Stratagene), TG1 or JM109. In all *B. subtilis* transformations, strain 1012 was used. Plasmids pHP13 [Haima et al., *Mol. Gen. Genet.* 209, 335–342 (1987)] and p602/22 [LeGrice, S. F. J. in *Gene Expression Technology*, Goeddel, D. V., Editor, 201–214 (1990)] are Gram (+)/(−) shuttle vectors able to replicate in *B. subtilis* and *E. coli* cells. Plasmid p205 contains the vegI promoter cloned into the SmaI site of pUC18. Plasmid pXI12 is an integration vector for the constitutive expression of genes in *B. subtilis* [Haiker et al., in *7th Int. Symposium on the Genetics of Industrial Microorganisms*, Jun. 26–Jul. 1, 1994. Mongreal, Quebec, Canada (1994)]. Plasmid pBEST501 [Itaya et al., *Nucleic Acids Res.* 17 (11), 4410 (1989)] contains the neomycin resistance gene cassette originating from the plasmid pUB110 (GenBank entry: M19465) of *S. aureus* [McKenzie et al., *Plasmid* 1 5, 93–103 (1986); McKenzie et al., *Plasmid* 17, 83–84 (1987)]. This neomycin gene has been shown to work as a selection marker when present in a single copy in the genome of *B. subtilis*. Plasmid pC194 (ATCC 37034)(GenBank entry: L08860) originates from *S. aureus* [Horinouchi and Weisblaum, *J. Bacteriol.* 150, 815–825 (1982)] and contains the chloramphenicol acetyltransferase gene.

Media and growth conditions: *E. coli* were grown in Luria broth (LB) at 37° C. with 100 mg Ampicillin (Amp)/ml for selection. *B. subtilis* cells were grown in VY-medium supplemented with either erythromycin (1 µg/ml), neomycin (5–180 mg/ml) or chloramphenicol (10–80 µg/ml).

Transformation: *E. coli* transformations were done by electroporation using the Gene-pulser device of BIO-RAD (Hercules, Calif., USA) with the following parameters (200 Ω, 250 µFD, 2.5 V). *B.subtilis* transformations were done basically according to the standard procedure method 2.8 described by [Cutting and Vander Horn in *Molecular Biological Methods for Bacillus*, Harwood, C. R. and Cutting, S. M., Editor, John Wiley & Sons: Chichester, England. 61–74 (1990)].

Colony screening: Bacterial colony screening was done as described by [Zon et al., supra].

Oligonucleotide synthesis: The oligonucleotides used for PCR reactions or for sequencing were synthesized with an Applied Biosystems 392 DNA synthesizer.

PCR reactions: The PCR reactions were performed using either the UlTma DNA polymerase (Perkin Elmer Cetus) or the Pfu Vent polymerase (New England Biolabs) according to the manufacturers instructions. A typical 50 ml PCR reaction contained: 100 ng of template DNA, 10 pM of each of the primers, all four dNTP's (final conc. 300 µM), $MgCl_2$ (when UlTma polymerase was used; final conc. 2 mM), 1× UlTma reaction buffer or 1× Pfu buffer (supplied by the manufacturer). All components of the reaction with the exception of the DNA polymerase were incubated at 95° C. for 2 min. followed by the cycles indicated in the respective section (see below). In all reactions a hot start was made, by adding the polymerase in the first round of the cycle during the 72° C. elongation step. At the end of the PCR reaction an aliquot was analysed on 1% agarose gel, before extracting once with phenol/chloroform. The amplified fragment in the aqueous phase was precipitated with ¹/₁₀ of a 3M NaAcetate solution and two volumes of Ethanol. After centrifugation for 5 min. at 12000 rpm, the pellet was resuspended in an adequate volume of $H_2O$, typically 40 µl, before digestion with the indicated restriction enzymes was performed. After the digestion the mixture was separated on a 1% low melting point agarose. The PCR product of the expected size were excised from the agarose and purified using the glass beads method (GENECLEAN KIT, Bio 101, Vista Calif., USA) when the fragments were above 400 bp or directly spun out of the gel when the fragments were shorter than 400 bp, as described by [Heery et al., *TIBS* 6 (6), 173 (1990)].

Oligos Used for Gene Amplification and Site Directed Mutagenesis:

All PCR reactions performed to allow the construction of the different plasmids are described below. All the primers used are summarized in FIG. 14.

Primers #100 and #101 were used in a PCR reaction to amplify the complete crtE gene having a SpeI restriction site and an artificial ribosomal binding site (RBS) upstream of the transcription start site of this gene. At the 3' end of the amplified fragment, two unique restriction sites were introduced, an AvrII and a SmaI site, to facilitate the further cloning steps. The PCR reaction was done with UlTma polymerase using the following conditions for the amplification: 5 cycles with the profile: 95° C., 1 min./60° C., 45 sec./72° C., 1 min. and 20 cycles with the profile: 95° C., 1 min./72° C., 1 min.. Plasmid pBIIKS(+)-clone2 served as template DNA. The final PCR product was digested with SpeI and SmaI and isolated using the GENECLEAN KIT. The size of the fragment was approx. 910 bp.

Primers #104 and #105 were used in a PCR reaction to amplify the crtZ gene from the translation start till the SalI restriction site, located in the coding sequence of this gene. At the 5' end of the crtZ gene an EcoRI, a synthetic RBS and a NdeI site was introduced. The PCR conditions were as described above. Plasmid pBIIKS(+)-clone 6a served as template DNA and the final PCR product was digested with EcoRI and SalI. Isolation of the fragment of approx. 480 bp was done with the GENECLEAN KIT.

Primers MUT1 and MUT5 were used to amplify the complete crtY gene. At the 5' end, the last 23 nucleotides of the crtZ gene including the SalI site are present, followed by an artificial RBS preceding the translation start site of the crtY gene. The artificial RBS created includes a PmlI restriction site. The 3' end of the amplified fragment contains 22 nucleotides of the crtI gene, preceded by an newly created artifial RBS which contains a MunI restriction site. The conditions used for the PCR reaction were as described above using the following cycling profile: 5 rounds of 95° C., 45 sec./60° C., 45 sec./72° C., 75 sec. followed by 22 cycles with the profile: 95° C., 45 sec./66° C., 45 sec./720C, 75 sec. Plasmid pXI12-ZYIB-EINV4 served as template for the Pfu Vent polymerase. The PCR product of 1225 bp was made blunt and cloned into the SmaI site of pUC18, using the Sure-Clone Kit (Pharmacia) according to the manufacturer.

Primers MUT2 and MUT6 were used to amplify the complete crtI gene. At the 5' the last 23 nucleotides of the crtY gene are present, followed by an artificial RBS which precedes the translation start site of the crtI gene. The new RBS created, includes a MunI restriction site. The 3' end of the amplified fragment contains the artificial RBS upstream of the crtB gene including a BamHI restriction site. The conditions used for the PCR reaction were basically as described above including the following cycling profile: 5 rounds of 95° C., 30 sec./60° C., 30 sec./72° C., 75 sec., followed by 25 cycles with the profile: 95° C., 30 sec./66° C., 30 sec./72° C., 75 sec. Plasmid pXI12-ZYIB-EINV4 served as template for the Pfu Vent polymerase. For the further cloning steps the PCR product of 1541 bp was digested with MunI and BamHI.

Primers MUT3 and CAR17 were used to amplify the N-terminus of the crtB gene. At the 5' the last 28 nucleotides of the crtI gene are present followed by an artificial RBS, preceding the translation start site of the crtB gene. This new created RBS, includes a BamHI restriction site. The amplified fragment, named PCR-F contains also the HindIII restriction site located at the N-terminus of the crtB gene.

The conditions used for the PCR reaction were as described elsewhere in the text, including the following cycling profile: 5 rounds of 95° C., 30 sec./58° C., 30 sec./72° C., 20 sec. followed by 25 cycles with the profile: 95° C., 30 sec./60° C., 30 sec./72° C., 20 sec. Plasmid pXI12-ZYIB-EINV4 served as template for the Pfu Vent polymerase. The PCR product of approx. 160 bp was digested with BamHI and HindIII.

Oligos Used to Amplify the Chloramphenicol Resistance Gene (cat):

Primers CAT3 and CAT4 were used to amplify the chloramphenicol resistance gene of pC194 (ATCC 37034) [Horinouchi and Weisblum, supra] a R-plasmid found in *S. aureus*. The conditions used for the PCR reaction were as described previously including the following cycling profile: 5 rounds of 95° C., 60 sec./50° C., 60 sec./72° C., 2 min. followed by 20 cycles with the profile: 95° C., 60 sec./60° C., 60 sec./72° C., 2 min.. Plasmid pC198 served as template for the Pfu Vent polymerase. The PCR product of approx. 1050 bp was digested with EcoRI and AatII.

Oligos used to generate linkers: Linkers were obtained by adding 90 ng of each of the two corresponding primers into an Eppendorf tube. The mixture was dried in a speed vac and the pellet resuspended in 1x Ligation buffer (Boehringer, Mannheim, Germany). The solution was incubated at 50° C. for 3 min. before cooling down to RT, to allow the primers to hybridize properly. The linker were now ready to be ligated into the appropriate sites. All the oligos used to generate linkers are shown in FIG. 15.

Primers CS1 and CS2 were used to form a linker containing the following restrictions sites HindIII, AflII, ScaI, XbaI, PmeI and EcoRI.

Primers MUT7 and MUT8 were used to form a linker containing the restriction sites SalI, AvrII, PmlI, MluI, MunI, BamHI, SphI and HindIII.

Primers MUT9 and MUT10 were used to introduce an artificial RBS upstream of crtY.

Primers MUT11 and MUT12 were used to introduce an artificial RBS upstream of crtE.

Isolation of RNA: Total RNA was prepared from log phase growing *B. subtilis* according to the method described by [Maes and Messens, *Nucleic Acids Res.* 20 (16), 4374 (1992)].

Northern Blot analysis: For hybridization experiments up to 30 mg of *B. subtilis* RNA was electrophoreses on a 1% agarose gel made up in 1x MOPS and 0.66 M formaldehyde. Transfer to Zeta-Probe blotting membranes (BIO-RAD), UV cross-linking, pre-hybridization and hybridization was done as described elsewhere in [Farrell, J. R. E., *RNA Methodologies. A laboratory Guide for isolation and characterization*. San Diego, USA: Academic Press (1993)]. The washing conditions used were: 2x20 min. in 2xSSPE/0.1% SDS followed by 1x20 min. in 0.1% SSPE/0.1% SDS at 65° C. Northern blots were then analyzed either by a Phosphorimager (Molecular Dynamics) or by autoradiography on X-ray films from Kodak.

Isolation of genomic DNA: *B. subtilis* genomic DNA was isolated from 25 ml overnight cultures according to the standard procedure method 2.6 described by Cutting, F. M. and Vander Horn, P. B., "Genetic Analysis" (pp. 61–74) in *Molecular Biological Methods for Bacillus*, Harwood and Cutting, Ed., (1990) John Wiley & Sons, Chichester, England.

Southern blot analysis: For hybridization experiments *B. subtilis* genomic DNA (3 mg) was digested with the appropriate restriction enzymes and electrophoresed on a 0.75% agarose gel. The transfer to Zeta-Probe blotting membranes (BIO-RAD), was done as described [Southern, E. M., supra]. Prehybridization and hybridization was in 7% SDS, 1% BSA (fraction V; Boehringer), 0.5M $Na_2HPO_4$, pH 7.2 at 65° C. After hybridization the membranes were washed twice for 5 min. in 2× SSC, 1% SDS at room temperature and twice for 15 min. in 0.1% SSC, 0.1% SDS at 65° C. Southern blots were then analyzed either by a Phosphorimager (Molecular Dynamics) or by autoradiography on X-ray films from Kodak.

DNA sequence analysis: The sequence was determined by the dideoxy chain termination technique [Sanger et al., s.a.] using the Sequenase Kit Version 1.0 (United States Biochemical). Sequence analysis were done using the GCG sequence analysis software package (Version 8.0) by Genetics Computer, Inc. [Devereux et al., supra].

Gene amplification in *B. subtilis*: To amplify the copy number of the SFCO in *B. subtilis* transformants, a single colony was inoculated in 15 ml VY-medium supplemented with 1.5 % glucose and 0.02 mg chloramphenicol or neomycin/ml, dependend on the antibiotic resistance gene present in the amplifiable structure (see results and discussion). The next day 750 ml of this culture were used to inoculate 13 ml VY-medium containing 1.5% glucose supplemented with (60, 80, 120 and 150 μg/ml) for the cat resistant mutants, or 160 μg/ml and 180 μg/ml for the neomycin resistant mutants). The cultures were grown overnight and the next day 50 μl of different dilutions (1:20, 1:400, 1:8000, 1:160,000) were plated on VY agar plates with the appropriate antibiotic concentration. Large single colonies were then further analyzed to determine the number of copies and the amount of carotenoids produced.

Analysis of carotenoids: *E. coli* or *B. subtilis* transformants (200–400 ml) were grown for the times indicated in the text, usually 24 to 72 hours, in LB-medium or VY-medium, respectively, supplemented with antibiotics, in shake flasks at 37° C. and 220 rpm.

The carotenoids produced by the microorganisms were extracted with an adequate volume of acetone using a rotation homogenizer (Polytron, Kinematica AG, CH-Luzern). The homogenate was the filtered through the sintered glass of a suction filter into a round bottom flask. The filtrate was evaporated by means of a rotation evaporator at 50° C. using a water-jet vacuum. For the zeaxanthin detection the residue was dissolved in n-hexane/acetone (86:14) before analysis with a normalphase HPLC as described in [Weber, S., supra]. For the detection of b-carotene and is lycopene the evaporated extract was dissolved in n-hexane/acetone (99:1) and analysed by HPLC as described in Hengartner et al., supra].

EXAMPLE 4

Carotenoid Production in *E. coli*

The biochemical assignment of the gene products of the different open reading frames (ORF's) of the carotenoid biosynthesis cluster of Flavobacterium sp. were revealed by analyzing the carotenoid accumulation in *E. coli* host strains, transformed with plasmids carrying deletions of the Flavobacterium sp. gene cluster, and thus lacking some of the crt gene products. Similar functional assays in *E. coli* have been described by other authors [Misawa et al., supra; Perry et al., *J. Bacteriol.*, 168, 607–612 (1986); Hundle, et al., *Molecular and General Genetics* 254 (4), 406–416 (1994)]. Three different plasmid pLyco, pBIIKS(+)-clone59-2 and pZea4 were constructed from the three genomic isolates pBIIKS(+)-clone2, pBIIKS(+)-clone59 and pBIIKS(+)-clone6a (see FIG. 16).

Figure 16A:
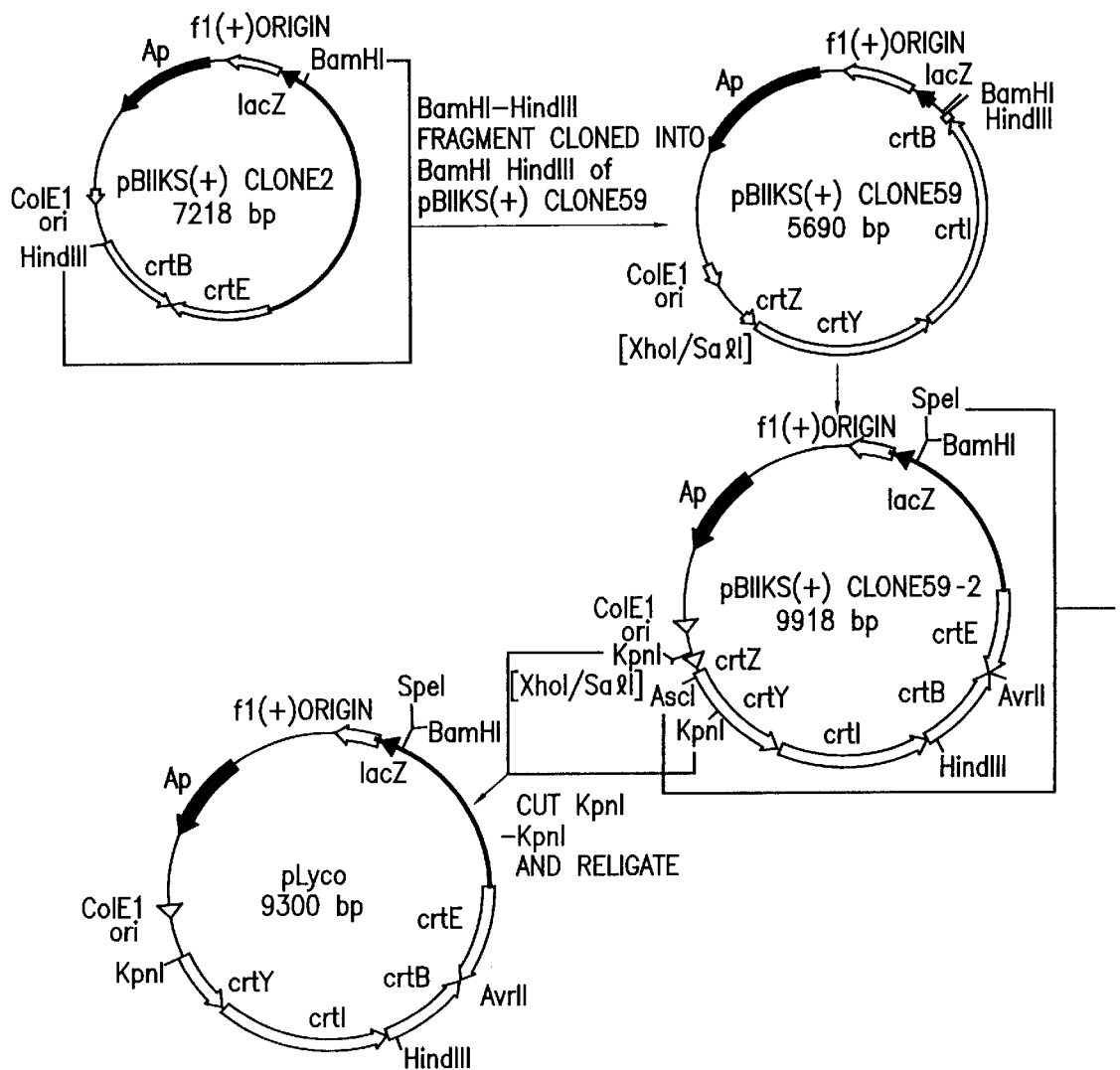
FIGS. 16A and 16B: Construction of plasmids pBIIKS (+)-clone59-2, pLyco and pZea4.
Figure 16B:
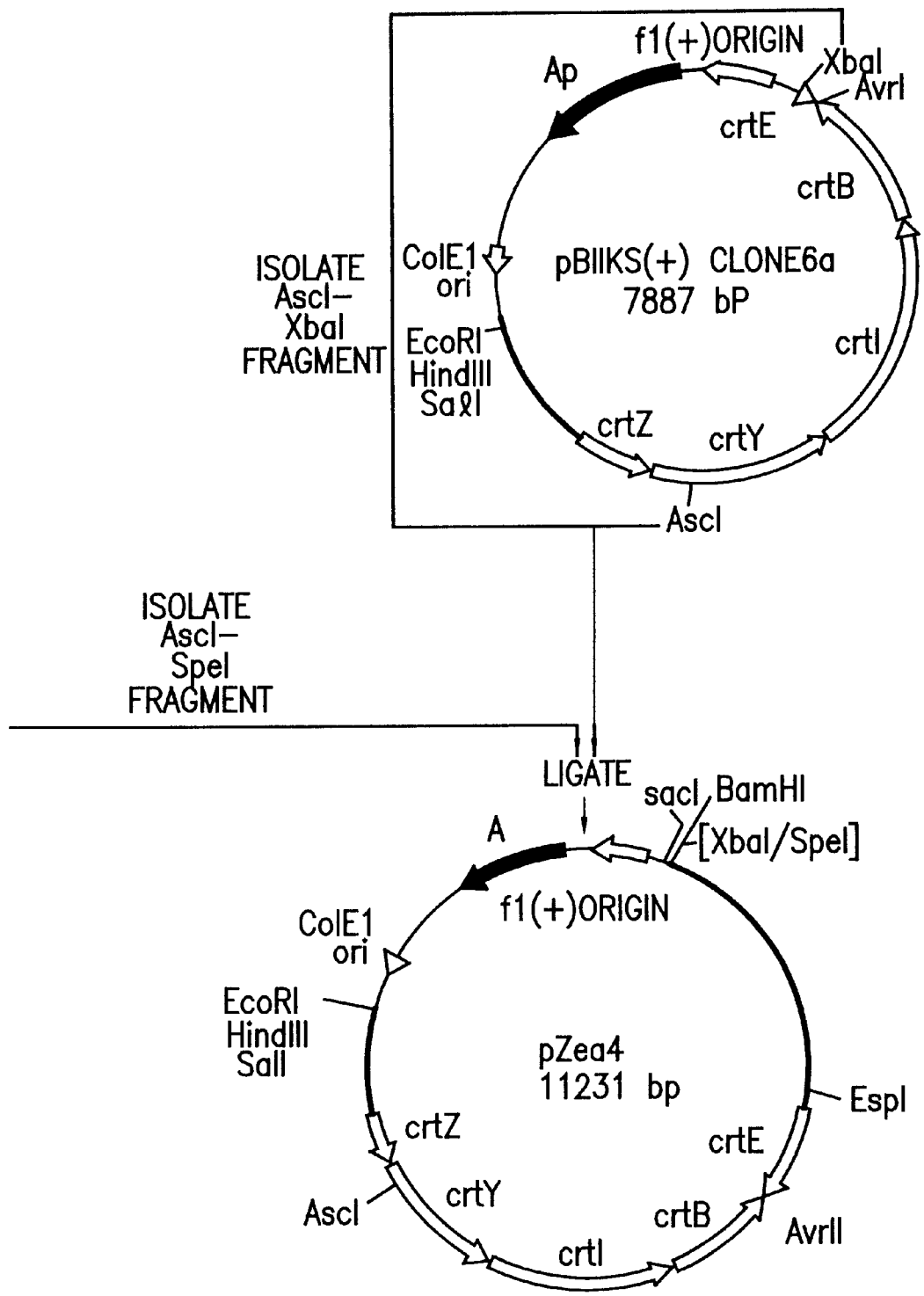

Plasmid pBIIKS(+)-clone59-2 was obtained by subcloning the HindIII/BamHI fragment of pBIIKS(+)-clone 2 into the HindIII/BamHI sites of pBIIKS(+)-clone59. The resulting plasmid pBIIKS(+)-clone59-2 carries the complete ORF's of the crtE, crtB, crtI and crtY gene and should lead to the production of b-carotene. pLyco was obtained by deleting the KpnI/KpnI fragment, coding for approx. one half (N-terminus) of the crtY gene, from the plasmid pBIIKS(+)-clone59-2. *E. coli* cells transformed with pLyco, and therefore having a truncated non-functional crtY gene, should produce lycopene, the precursor of b-carotene. pZea4 was constructed by ligation of the AscI-SpeI fragment of pBIIKS(+)-clone59-2, containing the crtE, crtB, crtI and most of the crtY gene with the AscI/XbaI fragment of clone 6a, containing the crtZ gene and sequences to complete the truncated crtY gene mentioned above. pZea4 has therefore all five ORF's of the zeaxanthin biosynthesis pathway. *E. coli* cells transformed with this latter plasmid should therefore produce zeaxanthin. For the detection of the carotenoid produced, transformants were grown for 43 hours in shake flasks and then subjected to carotenoid analysis as described in the methods section. FIG. 16 summarizes the construction of the plasmids described above.

As expected the pLyco carrying *E. coli* cells produced lycopene, those carrying pBIIKS(+)-clone59-2 produced b-carotene (all-E,9-Z,13-Z) and the cells having the pZea4 construct produced zeaxanthin. This confirms that we have cloned all the necessary genes of Flavobacterium sp. R1534 for the synthesis of zeaxanthin or their precursors (phytoene, lycopene and b-carotene). The production levels obtained are shown in table 1.

TABLE 1

| plasmid | host | zeaxanthin | b-carotene | lycopene |
|---------|------|------------|------------|----------|
| pLyco | *E. coli* JM109 | ND | ND | 0.05% |
| pBIIKS(+)-clone59-2 | " | ND | 0.03% | ND |
| pZea4 | " | 0.033% | 0.0009% | ND |

Table 1: Carotenoid content of *E. coli* transformants, carrying the plasmids pLyco, pBIIKS(+)-clone59-2 and pZea4, after 43 hours of culture in shake flasks. The values indicated show the carotenoid content in % of the total dry cell mass (200 ml). ND=not detectable.

EXAMPLES 5

Carotenoid Production in *B. subtilis*

In a first approach to produce carotenoids in *B. subtilis*, we cloned the carotenoid biosynthesis genes of Flavobacterium into the Gram (+)/(−) shuttle vectors p602/22, a derivative of p602/20 [LeGrice, S. F. J., s.a.]. The assembling of the final construct p602-CARVEG-E, begins with a triple ligation of fragments PvuII-AvrII of pZea4 (del654–3028) and the AvrII-EcoRI fragment from plasmid pBIIKS(+)-clone6a, into the EcoRI and ScaI sites of the vector p602/22. The plasmid pZea4(del654–3028) had been obtained by digesting pZea4 with SacI and EspI. The protruding and recessed ends were made blunt with Klenow enzyme and religated.

Figure 17A:
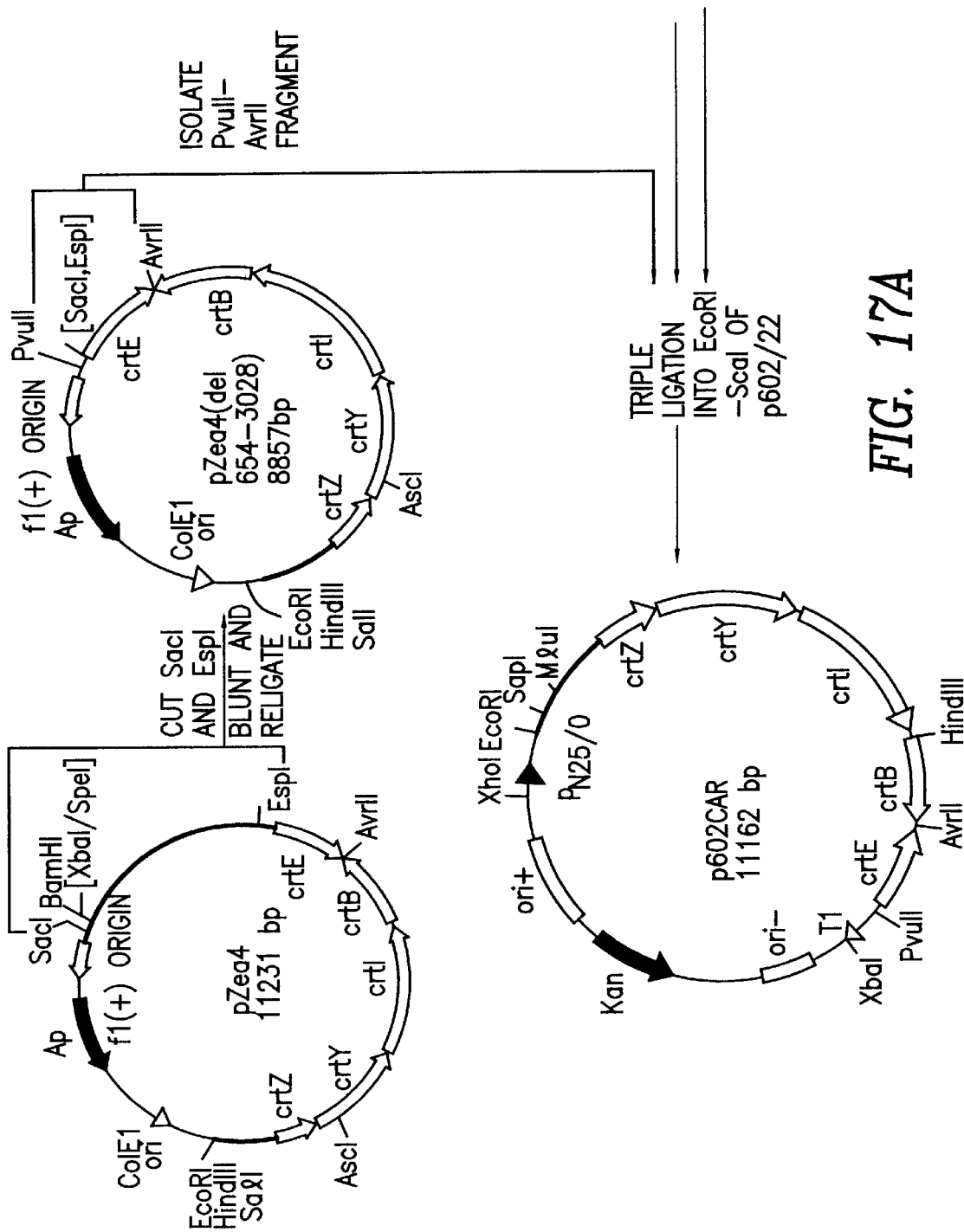
FIGS. 17A and 17B: Construction of plasmid p602CAR.
Figure 17B:
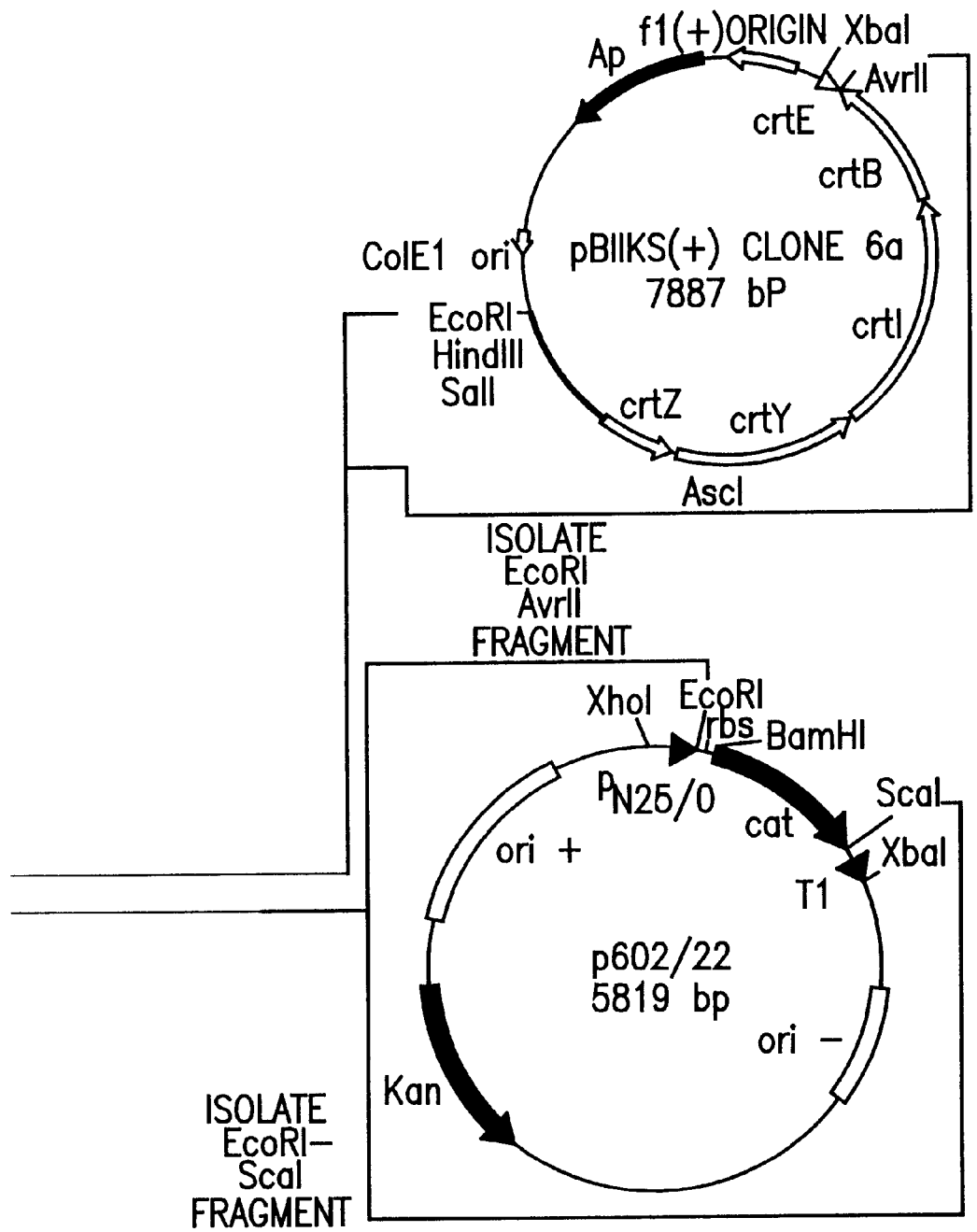
Figure 18A:
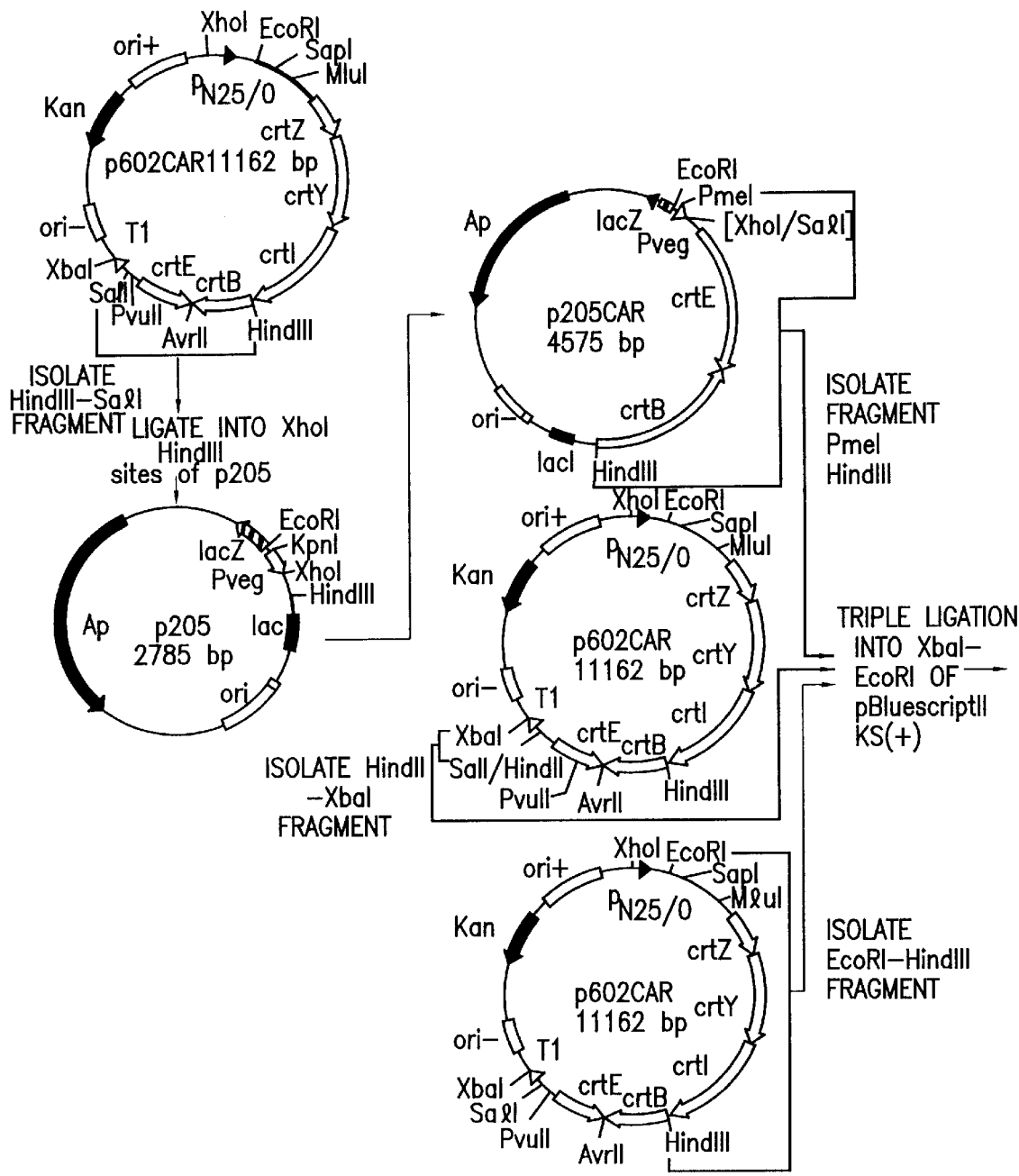
FIGS. 18A and 18B: Construction of plasmids pBIIKS (+)-CARVEG-E and p602 CARVEG-E.
Figure 18B:
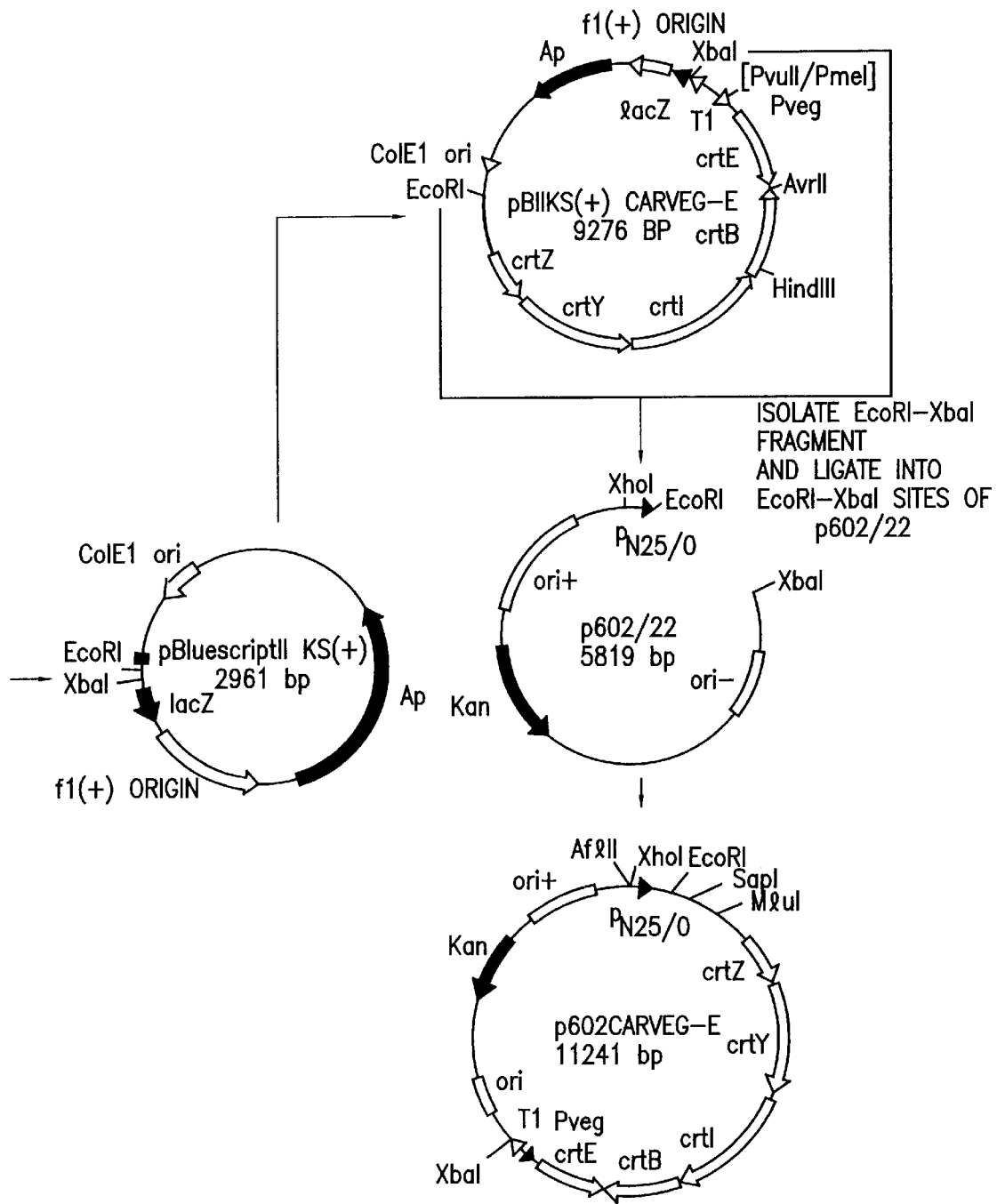

Construct pZea4(del654–3028) lacks most of the sequence upstream of crtE gene, which are not needed for the carotenoid biosynthesis. The plasmid p602-CAR has approx. 6.7 kb of genomic Flavobacterium R1534 DNA containing besides all five carotenoid genes (approx. 4.9 kb), additional genomic DNA of 1.2 kb, located upstream of the crtZ translation start site and further 200 bp, located upstream of crtE transcription start. The crtZ, crtY, crtI and crtB genes were cloned downstream of the P$_{N25/O}$ promoter, a regulatable E. coli bacteriophage T5 promoter derivative, fused to a lac operator element, which is functional in B. subtilis [LeGrice, S. F. J., supra]. It is obvious that in the p602CAR construct, the distance of over 1200 bp between the P$_{N25/O}$ promoter and the transcription start site of crtZ is not optimal and will be improved at a later stage. An outline of the p602CAR construction is shown in FIG. 17. To ensure transcription of the crtE gene in B. subtilis, the vegI promoter [Moran et al., Mol. Gen. Genet. 186, 339–346 (1982); LeGrice et al., Mol. Gen. Genet. 204, 229–236 (1986)] was introduced upstream of this gene, resulting in the plasmid construct p602-CARVEG-E. The vegl promoter, which originates from siteI of the veg promoter complex described by [LeGrice et al., supra] has been shown to be functional in E. coli [Moran et al., supra]. To obtain this new construct, the plasmid p602CAR was digested with SalI and HindIII, and the fragment containing the complete crtE gene and most of the crtB coding sequence, was subcloned into the XhoI and HindIII sites of plasmid p205. The resulting plasmid p205CAR contains the crtE gene just downstream of the PvegI promoter. To reconstitute the carotenoid gene cluster of Flavobacterium sp. the following three pieces were isolated: PmeI/HindIII fragment of p205CAR, the HincII/XbaI fragment and the EcoRI/HindIII fragment of p602CAR and ligated into the EcoRI and XbaI sites of pBluescriptIIKS(+), resulting in the construct pBIIKS(+)-CARVEG-E. Isolation of the EcoRI-XbaI fragment of this latter plasmid and ligation into the EcoRI and XbaI sites of p602/22 gives a plasmid similar to p602CAR but having the crtE gene driven by the PvegI promoter. All the construction steps to get the plasmid p602CARVEG-E are outlined in FIG. 18. E. coli TG1 cells transformed with this plasmid synthesized zeaxanthin. In contrast B. subtilis strain 1012 transformed with the same constructs did not produce any carotenoids. Analysis of several zeaxanthin negative B. subtilis transformants always revealed, that the transformed plasmids had undergone severe deletions. This instability could be due to the large size of the constructs.

In order to obtain a stable construct in B. subtilis, the carotenoid genes were cloned into the Gram (+)/(−) shuttle vector pHP13 constructed by [Haima et al., supra]. The stability problems were thought to be omitted by 1) reducing the size of the cloned insert which carries the carotenoid genes and 2) reversing the orientation of the crtE gene and thus only requiring one promoter for the expression of all five genes, instead of two, like in the previous constructs. Furthermore, the ability of cells transformed by such a plasmid carrying the synthetic Flavobacterium carotenoid operon (SFCO), to produce carotenoids, would answer the question if a modular approach is feasible.

Figure 19A:
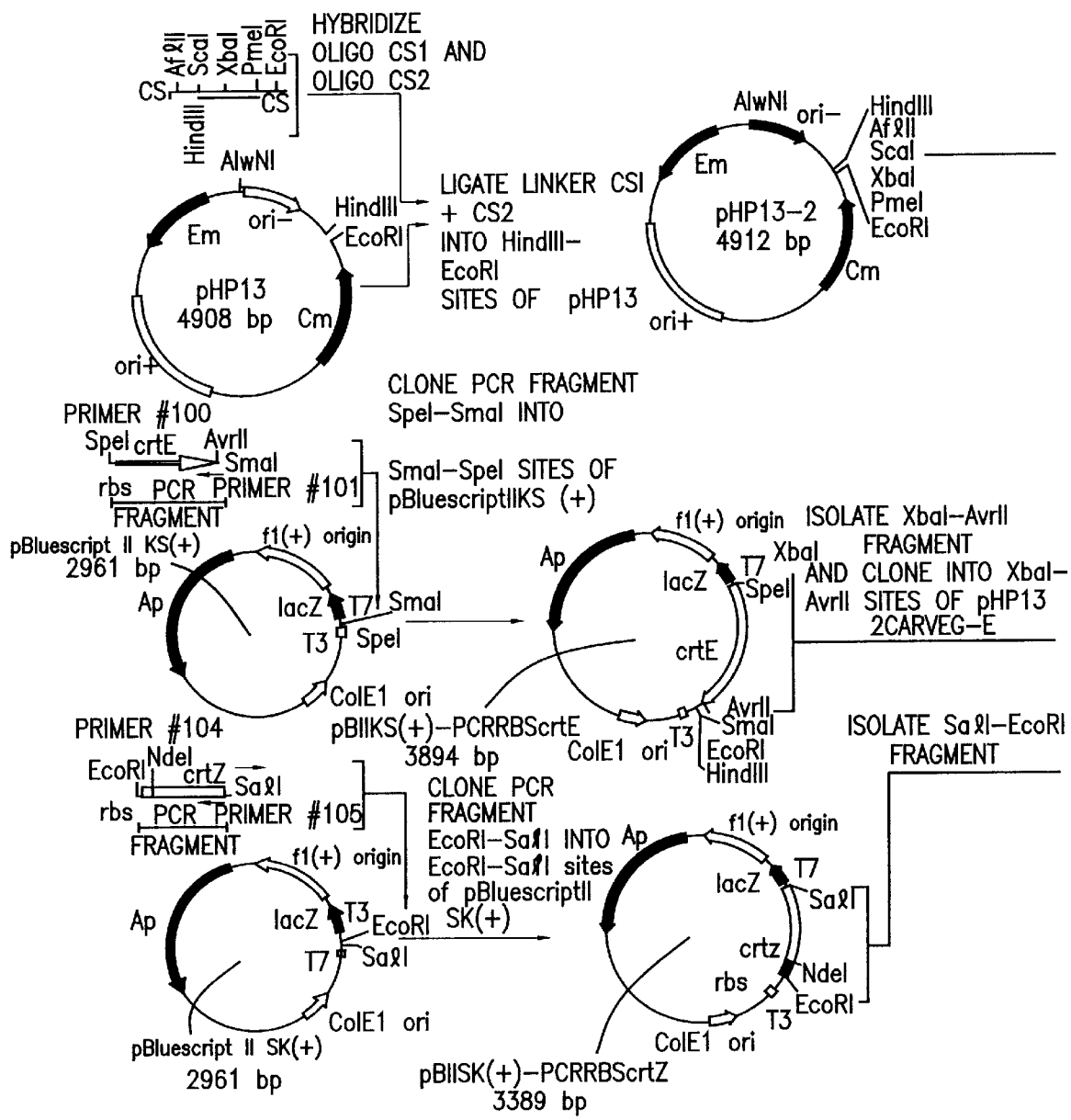
FIGS. 19A and 19B: Construction of plasmids pHP13-2CARZYIB-EINV and pHP13-2PN25ZYIB-EINV.
Figure 19B:
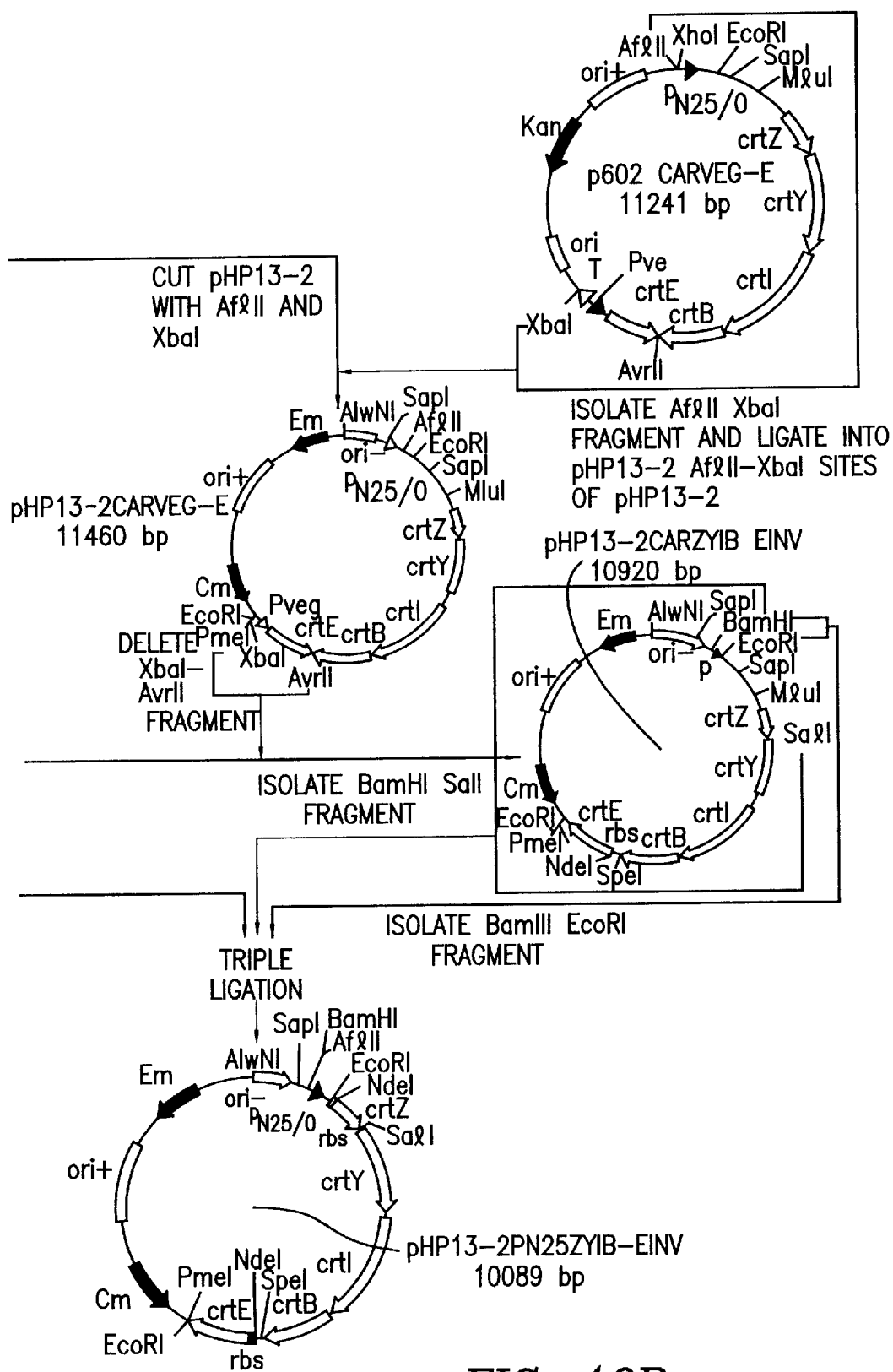
Figure 20A:
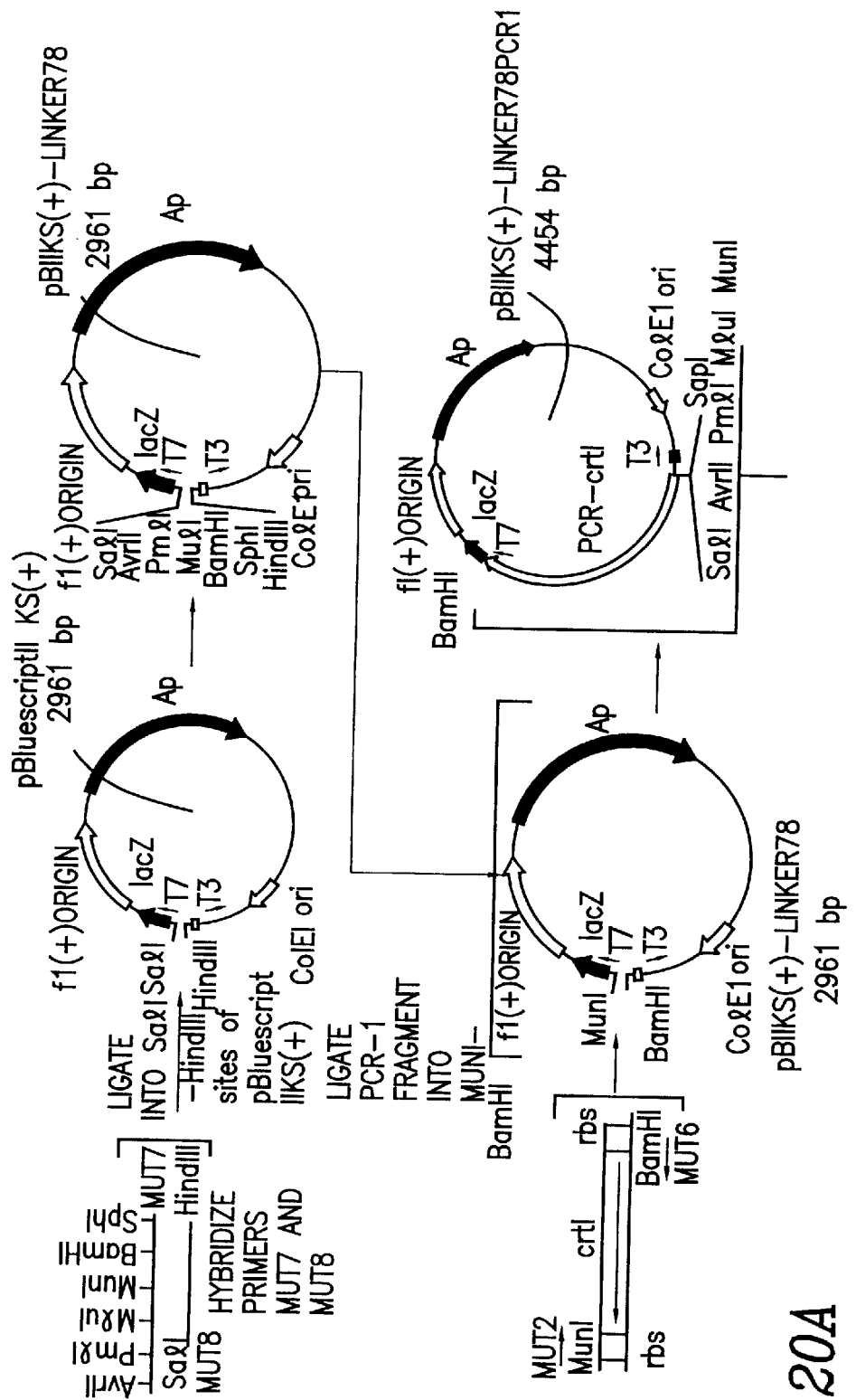
FIGS. 20A to 20G: Construction of plasmid pXI12-ZYIB-EINVMUTRBS2C.
Figure 20B:
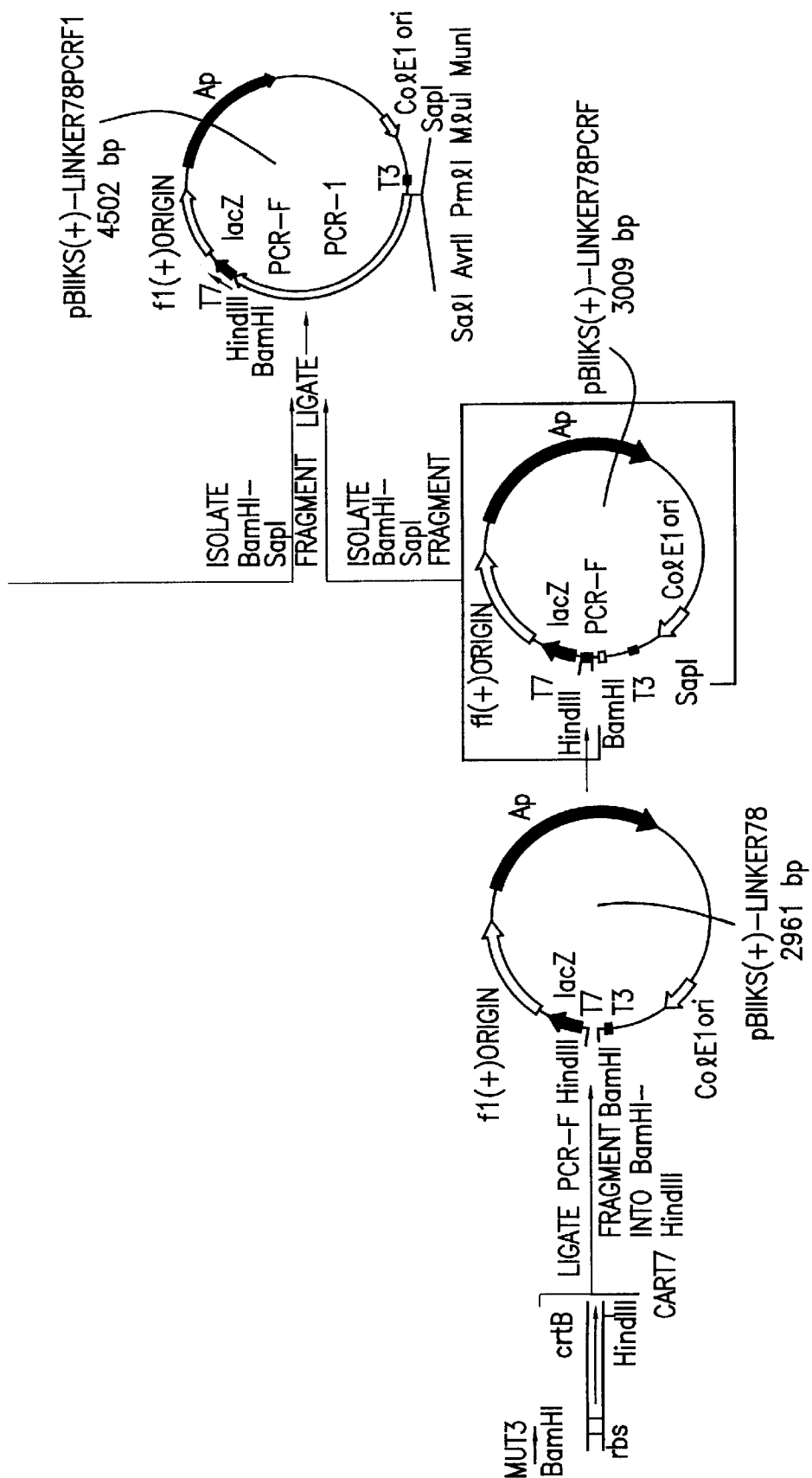
Figure 20C:
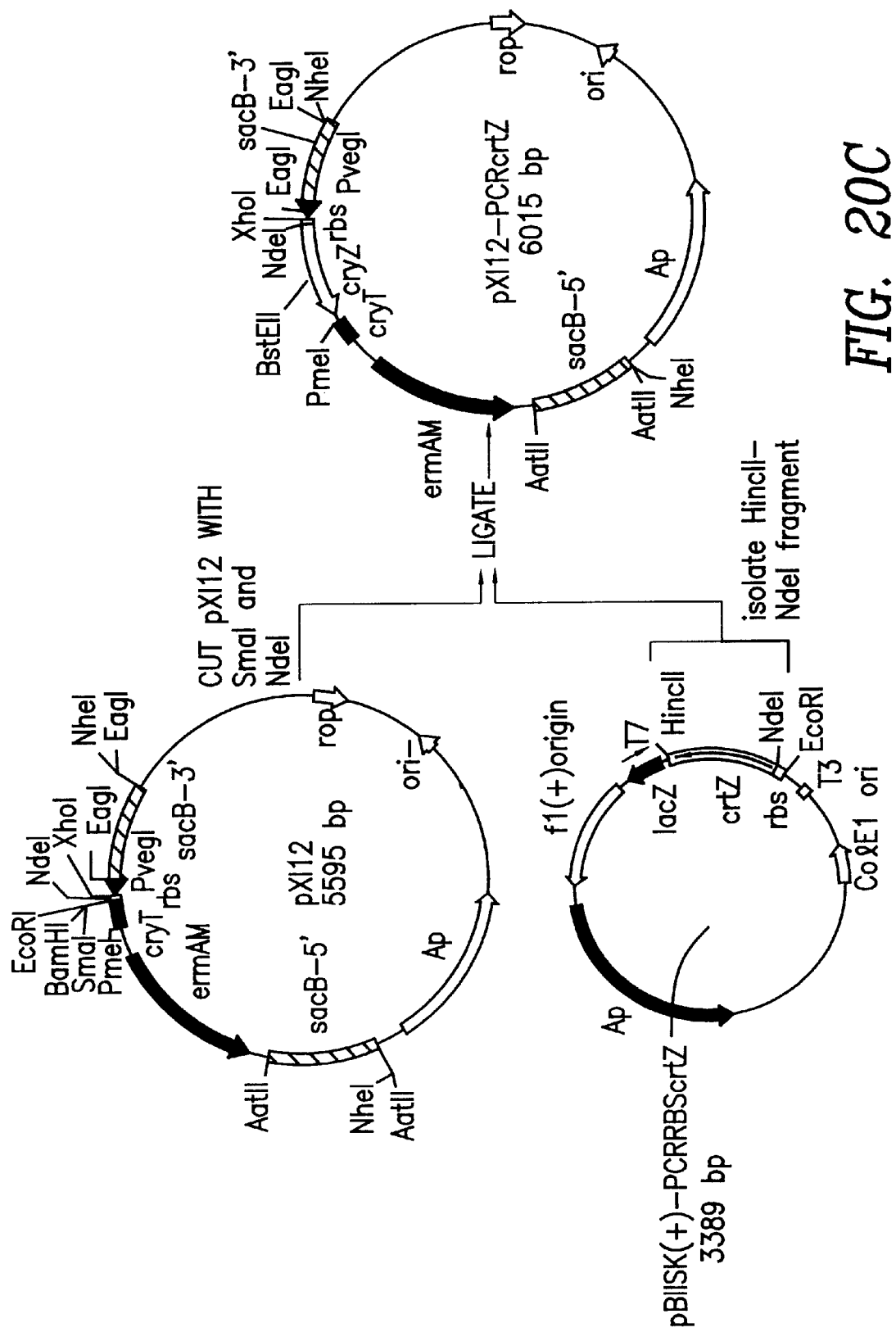
Figure 20D:
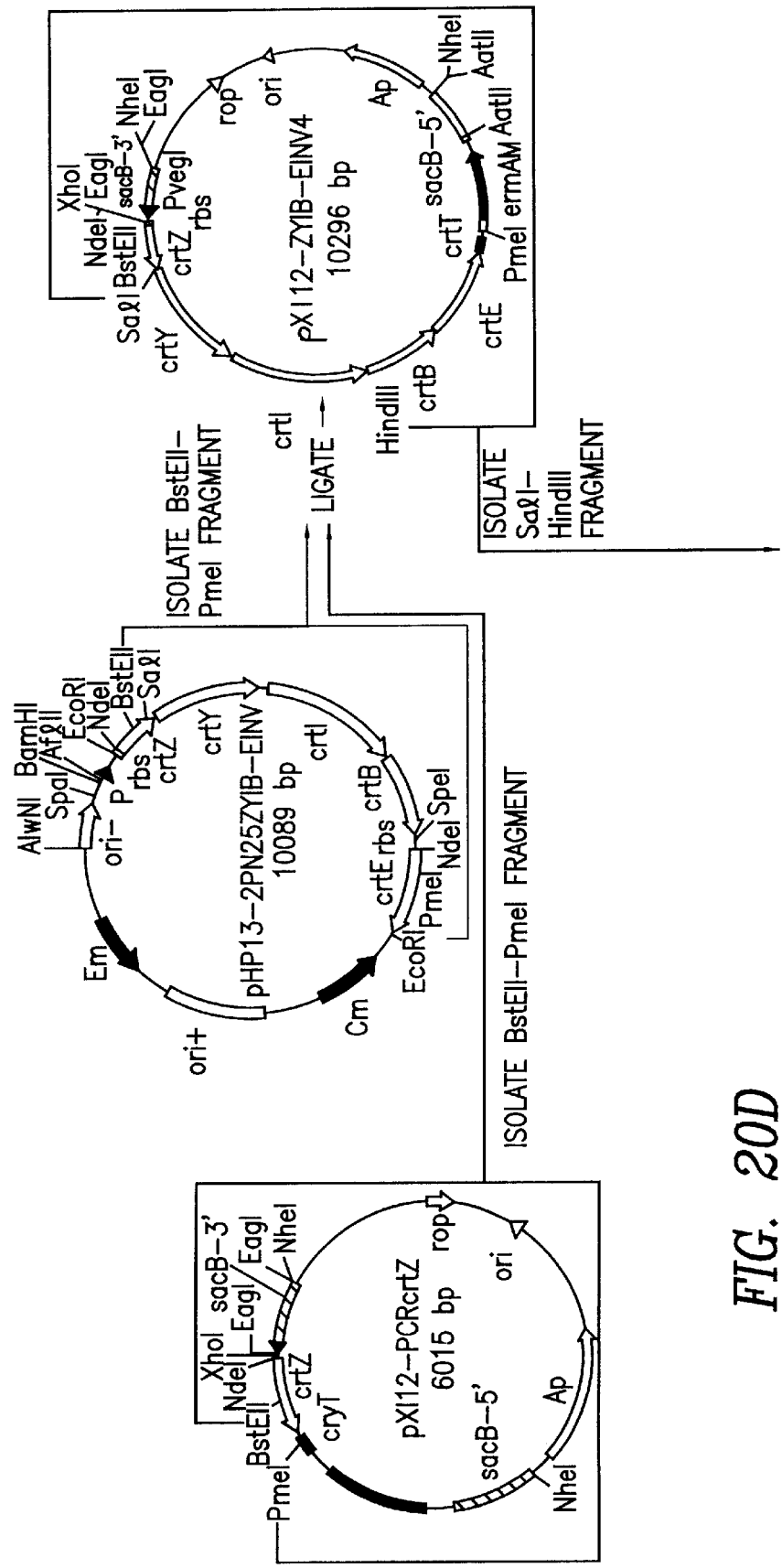
Figure 20E:
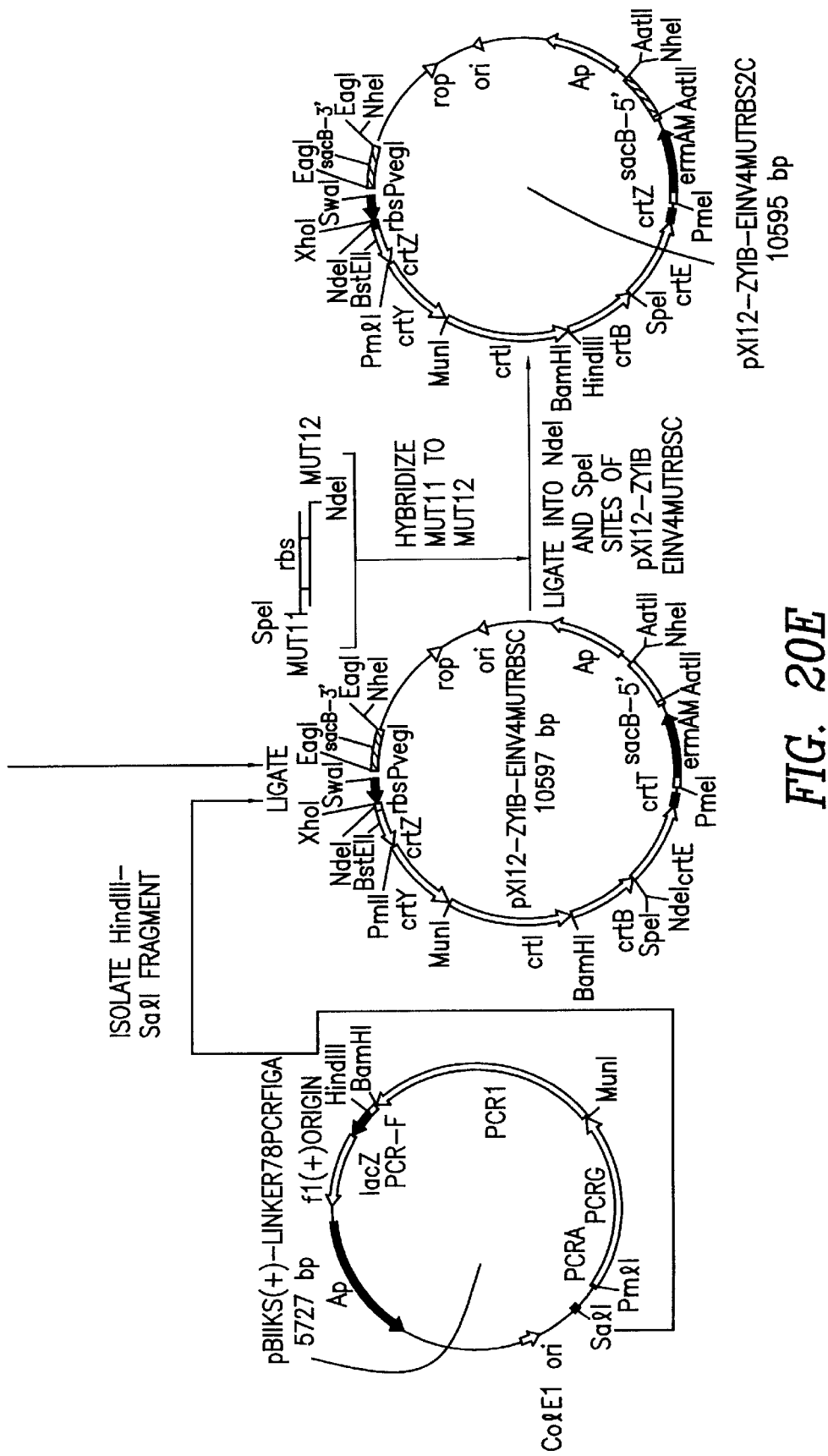
Figure 20F:
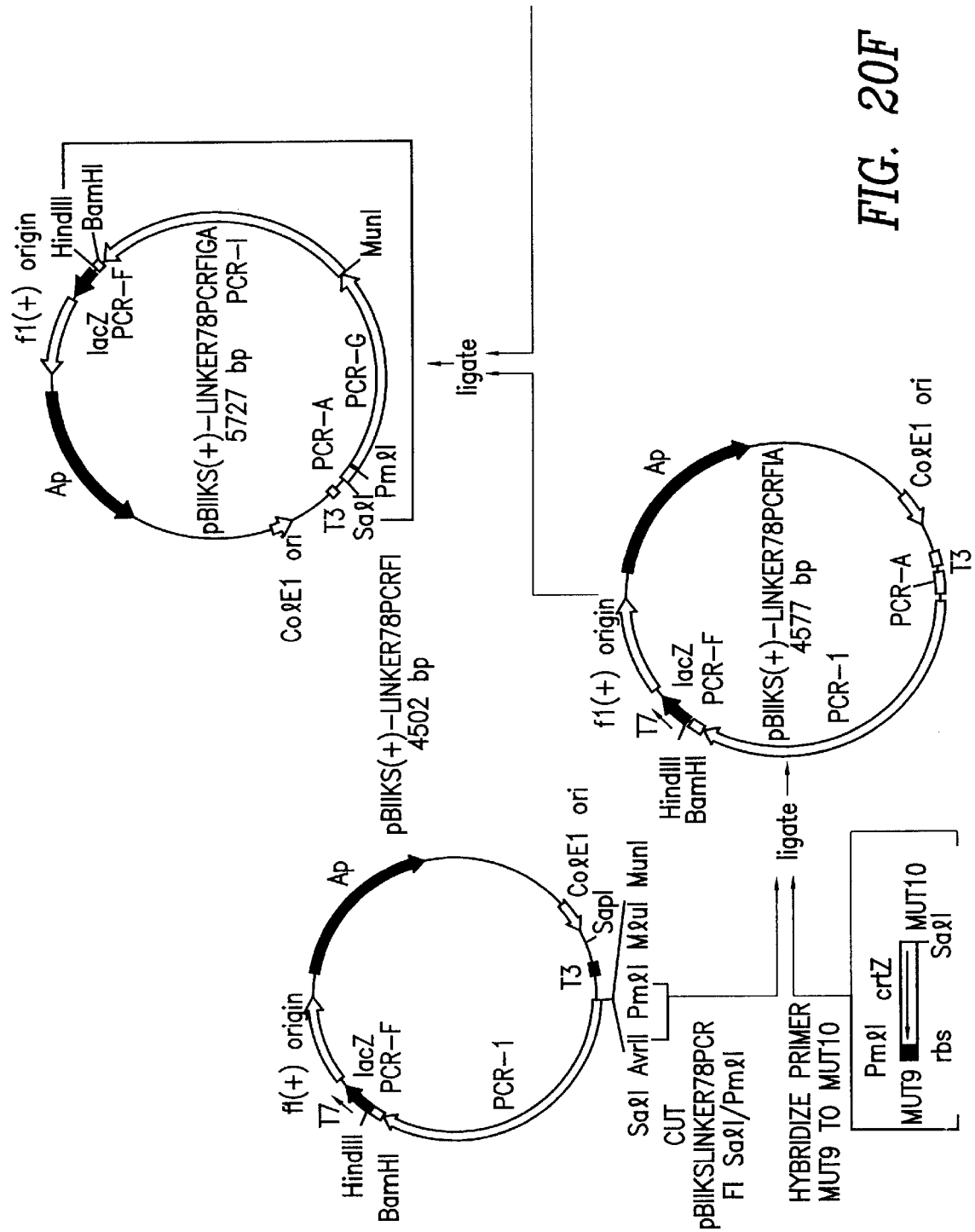
Figure 20G:
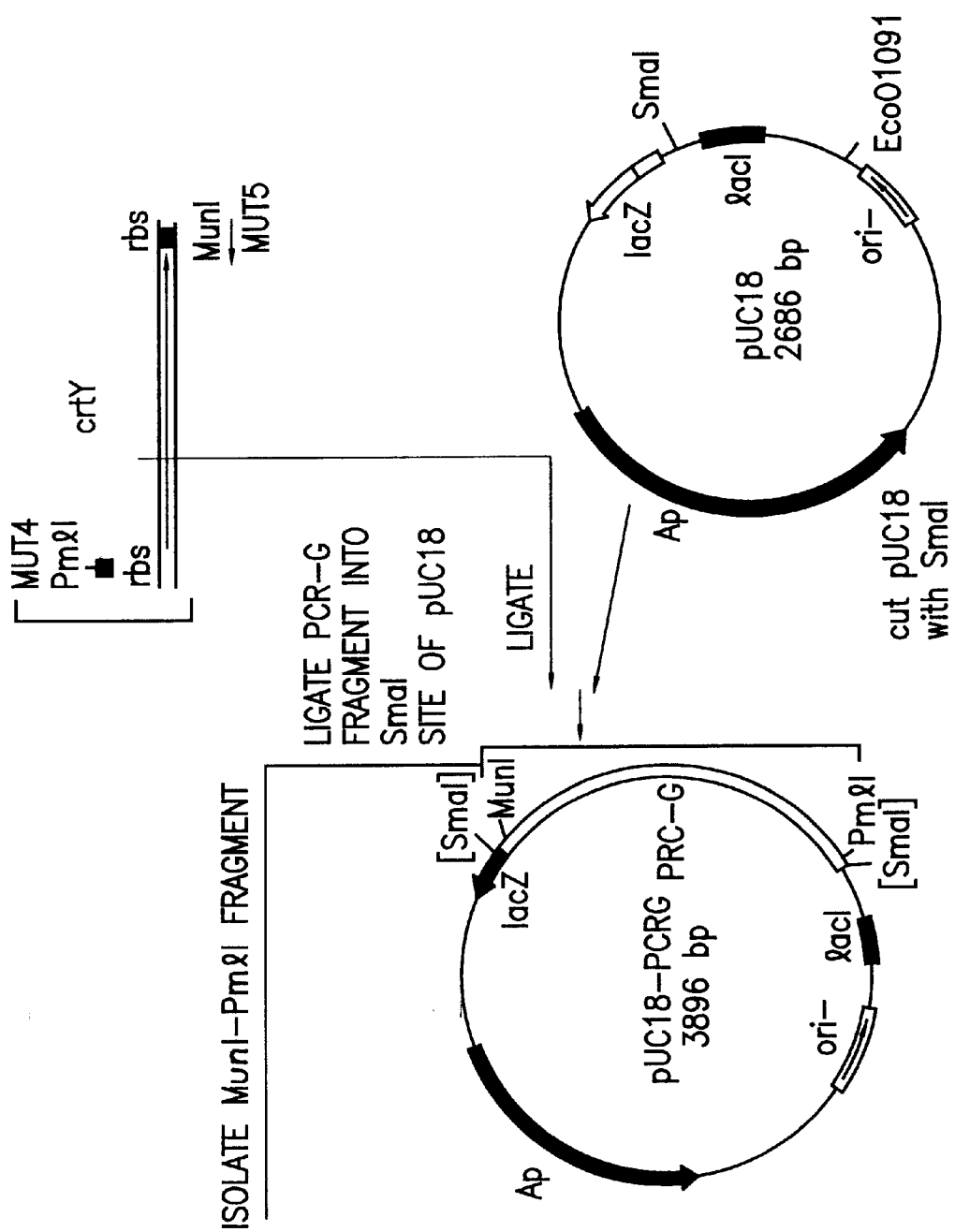

FIG. 19 summarizes all the construction steps and intermediate plasmids made to get the final construct pHP13-2PNZYIB-EINV. Briefly: To facilitate the following constructions, a vector pHP13-2 was made, by introducing a synthetic linker obtained with primer CS1 and CS2, between the HindIII and EcoRI sites of the shuttle vector pHP13. The intermediate construct pHP13-2CARVEG-E was constructed by subcloning the AflII-XbaI fragment of p602CARVEG-E into the AflII and XbaI sites of pHP13-2. The next step consisted in the inversion of crtE gene, by removing XbaI and AvrII fragment containing the original crtE gene and replacing it with the XbaI-AvrII fragment of plasmid pBIIKS(+)-PCRRBScrtE. The resulting plasmid was named pHP13-2CARZYIB-EINV and represented the first construction with a functional SFCO. The intermediate construct pBIIKS(+)-PCRRBScrtE mentioned above, was obtained by digesting the PCR product generated with primers #100 and #101 with SpeI and SmaI and ligating into the SpeI and SmaI sites of pBluescriptIIKS(+).

In order to get the crtZ transcription start close to the promoter P$_{N25/O}$ a triple ligation was done with the BamHI-SalI fragment of pHP13-2CARZYIB-EINV (contains four of the five carotenoid genes), the BamHI-EcoRI fragment of the same plasmid containing the P$_{N25/O}$ promoter and the EcoRI-SalI fragment of pBIIKS(+)-PCRRBScrtZ, having most of the crtZ gene preceded by a synthetic RBS. The aforementioned plasmid pBIISK(+)-PCRRBScrtZ was obtained by digesting the PCR product amplified with primers #104 and #105 with EcoRI and SalI and ligating into the EcoRI and SalI sites of pBluescriptIISK(+). In the resulting vector pHP13-2PN25ZYIB-EINV, the SFCO is driven by the bacteriophage T5 promoter P$_{N25/O}$, which should be constitutively expressed, due to the absence of a functional lac repressor in the construct [Peschke and Beuk, J. Mol. Biol. 186, 547–555 (1985)]. E. coli TG1 cells transformed with this construct produced zeaxanthin. Nevertheless, when this plasmid was transformed into B. subtilis, no carotenoid production could be detected. Analysis of the plasmids of these transformants showed severe deletions, pointing towards instability problems, similar to the observations made with the aforementioned plasmids.

EXAMPLES 6

Chromosome Integration Constructs

Due to the instability observed with the previous constructs we decided to integrate the carotenoid biosynthesis genes of Flavobacterium sp. into the genome of B. subtilis using the integration/expression vector pXI12. This vector allows the constitutive expression of whole operons after integration into the levan-sucrase gene (sacB) of the B. subtilis genome. The constitutive expression is driven by the vegI promoter and results in medium level expression. The plasmid pXI12-ZYIB-EINV4 containing the synthetic Flavobacterium carotenoid operon (SFCO) was constructed as follows: the NdeI-HincII fragment of pBIISK(+)-PCRRBScrtZ was cloned into the NdeI and SmaI sites of pXI12 and the resulting plasmid was named pXI12-PCRcrtZ. In the next step, the BstEII-PmeI fragment of pHP13-2PN25ZYIB-EINV was ligated to the BstEII-PmeI fragment of pXI12-PCRcrtZ (see FIG. 20).

Figure 21A:
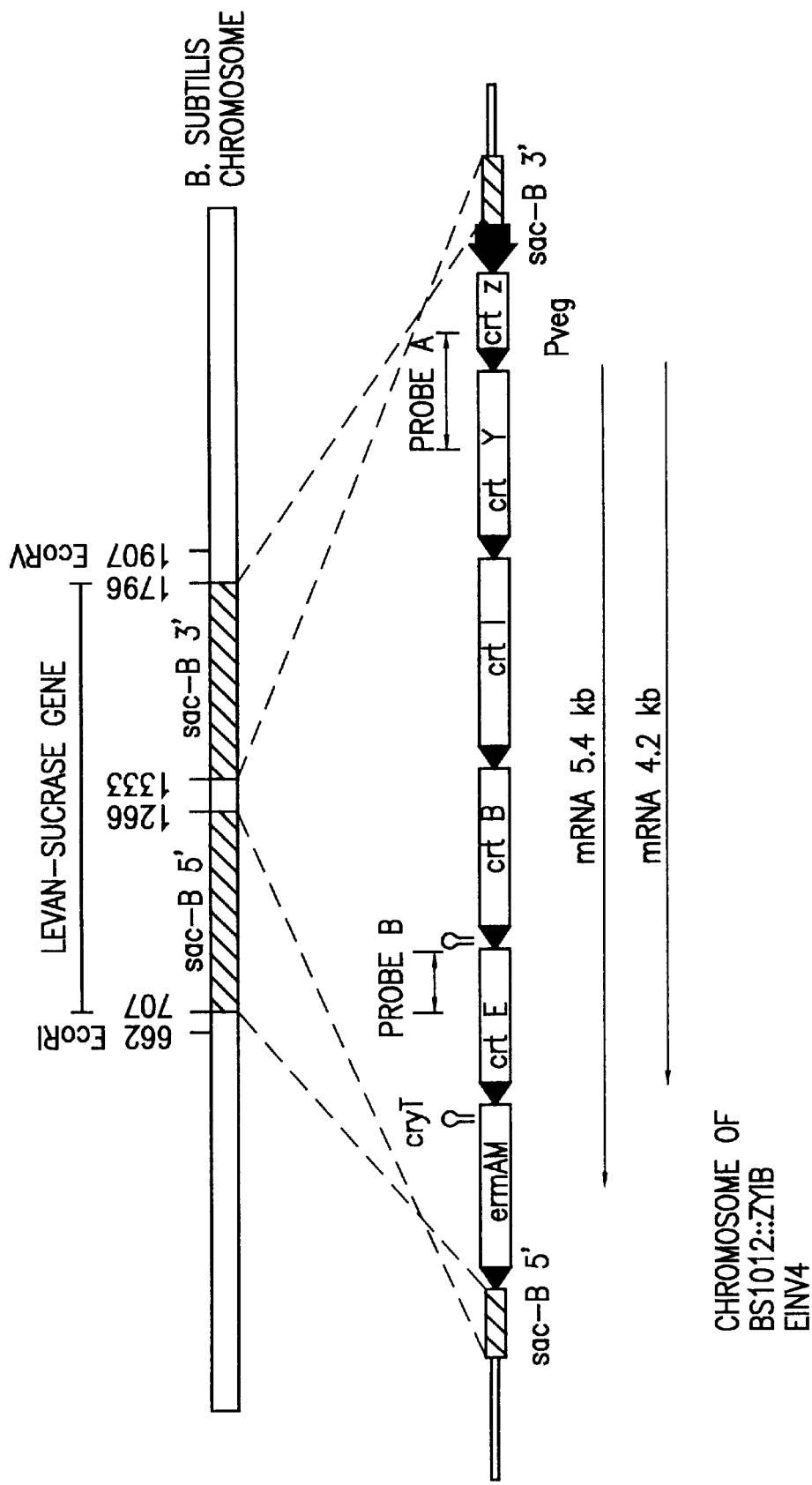
FIG. 21A: Schematic representation of a reciprocal integration of plasmid pXI12-ZYIB-EINV4 into the levan-sucrase gene of *B-subtilis*.
Figure 21B:
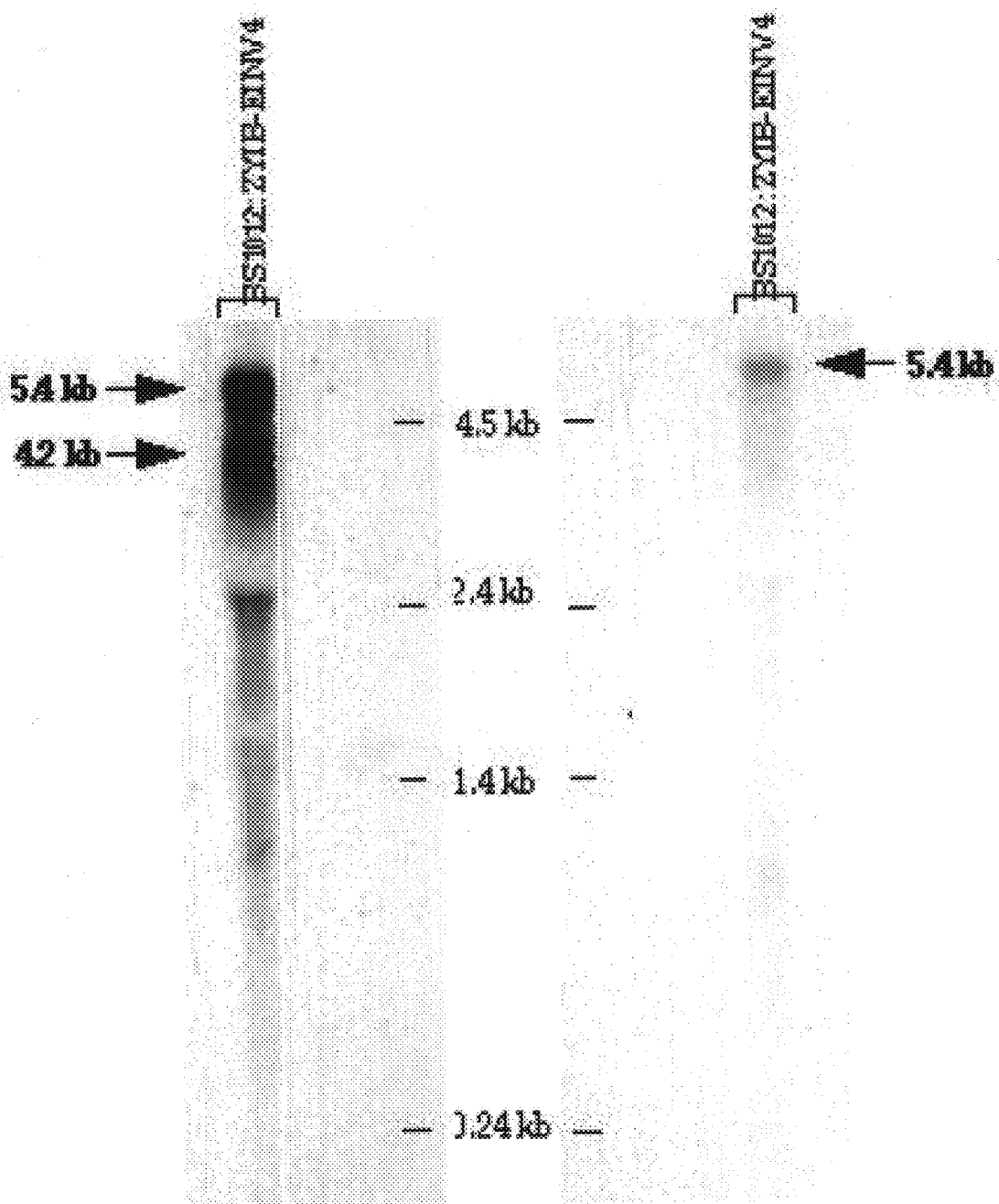
FIG. 21B: Northern blot obtained with probe A (PCR fragment which was obtained with CAR 51 and CAR 76 and hybridizes to the 3' end of crtZ and the 5' end or crty). Panel C: Northern blot obtained with probe B (BamHI-XhoI fragment isolated from plasmid pBIIKS(+)-crtE/2 and hybridizing to the 5' part of the crtE gene).

B. subtilis transformed with the resulting construct pXI12-ZYIB-EINV4 can integrate the CAR genes either via a Campbell type reaction or via a reciprocal recombination. One transformant, BS1012::ZYIB-EINV4, having a reciprocal recombination of the carotenoid biosynthesis genes into the levan-sucrase gene was further analyzed (FIG. 21). Although this strain did not synthesize carotenoids, RNA analysis by Northern blots showed the presence of specific polycistronic mRNA's of 5.4 kb and 4.2 kb when hybridized to probe A (see FIG. 21, panel B). Whereas the larger mRNA has the expected message size, the origin of the shorter mRNA was unclear. Hybridization of the same Northern blot to probe B only detected the large mRNA fragment, pointing towards a premature termination of the transcription at the end of the crtB gene. The presence of a termination signal at this location would make sense, since in the original operon organisation in the Flavobacterium sp. R1534 genome, the crtE and the crtB genes are facing each other. With this constellation a transcription termination signal at the 5' end of crtB would make sense, in order to avoid the synthesis of anti-sense RNA which could interfere with the mRNA transcript of the crtE gene. Since this region has been changed considerably with respect to the wild type situation, the sequences constituting this terminator may also have been altered resulting in a "leaky" terminator.

Western blot analysis using antisera against the different crt enzymes of the carotenoid pathway, pointed towards the possibility that the ribosomal binding sites might be responsible for the lack of carotenoid synthesis. Out of the five genes introduced only the product of crtZ, the β-carotene hydroxylase was detectable. This is the only gene preceded by a RBS site, originating from the pXI12 vector, known to be functional in B. subtilis. Base pairing interactions between a mRNA's Shine-Dalgarno sequence [Shine and Delagarno, supra] and the 16S rRNA, which permits the ribosome to select the proper initiation site, have been proposed by [McLaughlin et al., J. Biol. Chem. 256, 11283–11291 (1981)] to be much more stable in Gram-positive organisms (B. subtilis) than in Gram-negative organisms (E. coli). In order to obtain highly stable complexes we exchanged the RBS sites of the Gram-negative Flavobacterium sp., preceding each of the genes crtY, crtI, crtB and crtE, with synthetic RBS's which were designed complementary to the 3' end of the B. subtilis 16S rRNA (see Table 2). This exchange should allow an effective translation initiation of the different carotenoid genes in B. subtilis. The strategy chosen to construct this pXI12-ZYIB-EINV4MUTRBS2C, containing all four altered sites is summarized in FIG. 20. In order to facilitate the further cloning steps in pBluescriptIIKS(+), additional restriction sites were introduced using the linker obtained with primer MUT7 and MUT8, cloned between the SalI and HindIII sites of said vector.

The new resulting construct pBIIKS(+)-LINKER78 had the following restriction sites introduced: AvrII, PmlI, MulI, MunI, BamHI and SphI. The general approach chosen to create the synthetic RBS's upstream of the different carotenoid genes, was done using a combination of PCR based mutagenesis, where the genes were reconstructed using defined primers carrying the modified RBS sites, or using synthetic linkers having such sequences. Reconstitution of the RBS preceding the crtI and crtB genes was done by amplifying the crtI gene with the primers MUT2 and MUT6, which include the appropriate altered RBS sites. The PCR-I fragment obtained was digested with MunI and BamHI and ligated into the MunI and BamHI sites of pBIIKS(+)-LINKER78. The resulting intermediate construct was named pBIIKS(+)-LINKER78PCRI. Reconstitution of the RBS preceding the crtB gene was done using a small PCR fragment obtained with primer MUT3, carrying the altered RBS site upstream of crtB, and primer CAR17.

The amplified PCR-F fragment was digested with BamHI and HindIII and sub cloned into the BamHI and HindIII sites of pBIIKS(+)-LINKER78, resulting in the construct pBIIKS (+)-LINKER78PCRF. The PCR-I fragment was cut out of pBIIKS(+)-LINKER78PCRI with BamHI and SapI and ligated into the BamHI and SapI sites of pBIIKS(+)-LINKER78PCRF. The resulting plasmid pBIIKS(+)-LINKER78PCRFI has the PCR-I fragment fused to the PCR-F fragment. This construct was cut with SalI and PmlI and a synthetic linker obtained by annealing of primer MUT9 and MUT10 was introduced. This latter step was done to facilitate the upcoming replacement of the original Flavobacterium RBS in the above mentioned construct. The resulting plasmid was named pBIIKS(+)-LINKER78PCRFIA. Assembling of the synthetic RBS's preceding the crtY and crtI genes was done by PCR, using primers MUT1 and MUT5.

The amplified fragment PCR-G was made blunt end before cloning into the SmaI site of pUC18, resulting in construct pUC18-PCR-G. The next step was the cloning of the PCR-G fragment between the PCR-A and PCR-I fragments. For this purpose the PCR-G was isolated from pUC18-PCR-G by digesting with MunI and PmlI and ligated into the MunI and PmlI sites of pBIIKS(+)-LINKER78PCRFIA. This construct contains all four fragments, PCR-F, PCR-I, PCR-G and PCR-A, assembled adjacent to each other and containing three of the four artificial RBS sites (crtY, crtI and crtB). The exchange of the Flavobacterium RBS's preceding the genes crtY, crtI and crtB by synthetic ones, was done by replacing the HindIII-SalI fragment of plasmid pXI12-ZYIB-EINV4 with the HindIII-SalI fragment of plasmid pBIIKS(+)-LINKER78PCRFIGA.

The resulting plasmid pXI12-ZYIB-EINV4 MUTRBSC was subsequently transformed into E. coli TG1 cells and B. subtilis 1012. The production of zeaxanthin by these cells confirmed that the PCR amplified genes where functional. The B. subtilis strain obtained was named BS1012::SFCO1. The last Flavobacterium RBS to be exchanged was the one preceding the crtE gene. This was done using a linker obtained using primer MUT11 and MUT12. The wild type RBS was removed from pXI12-ZYIB-EINV4MUTRBS with NdeI and SpeI and the above mentioned linker was inserted. In the construct pXI12-ZYIB-EINV4MUTRBS2C all Flavobacterium RBS's have been replaced by synthetic RBS's of the consensus sequence AAAGGAGG-7-8 N-ATG (see table 2). E. coli TG1 cells transformed with this construct showed that also this last RBS replacement had not interferred

TABLE 2

| mRNA | | nucleotide sequence | |
|---|---|---|---|
| crtZ | | AAAGGAGGGUUUCAU<u>AUG</u>AGC | [SEQ ID NO: 19] |
| crtY | | AAAGGAGGACACGUG<u>AUG</u>AGC | [SEQ ID NO: 20] |
| crtI | | AAAGGAGGCAAUUGAG<u>AUG</u>AGU | [SEQ ID NO: 21] |
| crtB | | AAAGGAGGAUCCAAUC<u>AUG</u>ACC | [SEQ ID NO: 22] |
| crtE | | AAAGGAGGGUUUCUU<u>AUG</u>ACG | [SEQ ID NO: 23] |
| B. subtilis | 16S rRNA | 3'-UCUUUCCUCCACUAG | [SEQ ID NO: 24] |
| E. coli | 16S rRNA | 3'-AUUCCUCCACUAG | [SEQ ID NO: 25] |

Table 2: Nucleotide sequences of the synthetic ribosome binding sites in the constructs pXI12-ZYIB-EINV4MUTRBS2C, pXI12-ZYIB-EINV4MUTRB S2CCAT and pXI12-ZYIB -EINV4 MUTRBS2CNEO. Nucleotides of the Shine-Dalgarno sequence preceding the individual carotenoid genes which are complementary to the 3' ends of the 16S rRNA of B. subtilis are shown in bold. The 3' ends of the 16S rRNA of E. coli is also shown as comparison. The underlined AUG is the translation start site of the mentioned gene. with the ability to produce zeaxanthin. All the regions containing the newly introduced synthetic RBS's were confirmed by sequencing. B. subtilis cells were transformed with plasmid pXI12-ZYIB-EINV4MUTRBS2 and one transformant having integrated the SFCO by reciprocal recombination, into the levan-sucrase gene of the chromosome, was selected. This strain was named BS1012::SFCO2.

Analysis of the carotenoid production of this strain show that the amounts zeaxanthin produced is approx. 40% of the zeaxanthin produced by E. coli cells transformed with the plasmid used to get the B. subtilis transformant. Similar was the observation when comparing the BS1012::SFCO1 strain with its E. coli counter part (30%). Although the E. coli cells have 18 times more carotenoid genes, the carotenoid production is only a factor of 2–3 times higher. More drastic was the difference observed in the carotenoid contents, between E. coli cells carrying the pZea4 construct in about 200 copies and the E. coli carrying the plasmid pXI12-ZYIB-EINV4MUTRBS2C in 18 copies. The first transformant produced 48× more zeaxanthin than the latter one. This difference seen can not only be attributed to the roughly 11 times more carotenoid biosynthesis genes present in these transformants. Contributing to this difference is probably also the suboptimal performance of the newly constructed SFCO, in which the overlapping genes of the wild type Flavobacterium operon were separated to introduce the synthetic RBS's. This could have resulted in a lower translation efficiency of the rebuild synthetic operon (e.g., due to elimination of putative translational coupling effects, present in the wild type operon).

Figure 22:
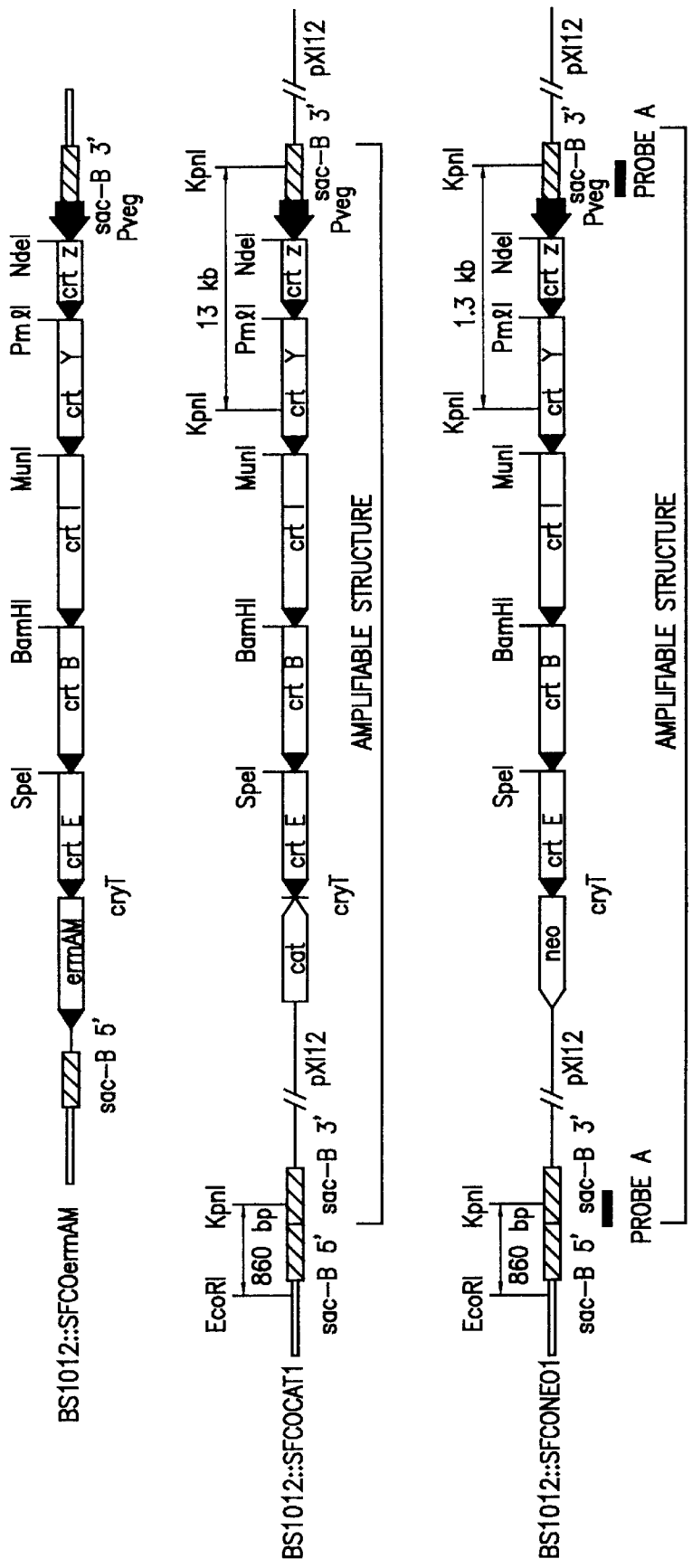
FIG. 22: Schematic representation of the integration sites of three transformed *Bacillus subtilis* strains: BS1012::SFCO, BS1012::SFCOCAT1 and BA1012::SFCONEO1. Amplification of the synthetic Flavobacterium carotenoid operon (SFCO) can only be obtained in those strains having amplifiable structures. Probe A was used to determine the copy number of the integrated SFCO. Erythromycine resistance gene (ermAM), chloramphenicol resistance gene (cat), neomycine resistance gene (neo), terminator of the cryT gene of *B. subtilis* (cryT), levan-sucrase gene (sac-B 5' and sac-B 3'), plasmid sequences of pXI12 (pXI12), promoter originating from site I of the veg promoter complex (Pveg1).

In order to increase the carotenoid production, two new constructs were made, pXI12-ZYIB-EINV4MUTRBS2CNEO and pXI12-ZYIB-EINV4MUTRBS2CCAT, which after the integration of the SFCO into the levan-sucrase site of the chromosome, generate strains with an amplifiable structure as described by [Janniere et al., Gene 40, 47–55 (1985)]. Plasmid pXI12-ZYIB-EINV4MUTRBS2CNEO has been deposited on May 25, 1995 at the DSM-Deutsche Sammlung von Mikroorganismen und Zellkulturen GmbH (Germany) under accession No. DSM 10013. Such amplifiable structures, when linked to a resistance marker (e.g., chloramphenicol, neomycin, tetracycline), can be amplified to 20–50 copies per chromosome. The amplifiable structure consist of the SFCO, the resistance gene and the pXI12 sequence, flanked by direct repeats of the sac-B 3' gene (see FIG. 22). New strains having elevated numbers of the SFCO could now be obtained by selecting for transformants with increased level of resistance to the antibiotic.

To construct plasmid pXI12-ZYIB-EINV4MUTRBS2CNEO, the neomycin resistance gene was isolated from plasmid pBEST501 with PstI and SmaI and subcloned into the PstI and EcoO1091 sites of the pUC18 vector. The resulting construct was named pUC18-Neo. To get the final construct, the PmeI-AatII fragment of plasmid pXI12-ZYIB-EINV4MUTRBS2C was replaced with the SmaI-AatII fragment of pUC18-Neo, containing the neomycin resistance gene. Plasmid pXI12-ZYIB-EINV4MUTRBS2CCAT was obtained as follows: the chloramphenicol resistance gene of pC194 was isolated by PCR using the primer pair cat3 and cat4. The fragment was digested with EcoRI and AatII and subcloned into the EcoRI and AatII sites of pUC18. The resulting plasmid was named pUC18-CAT.

Figure 23A:
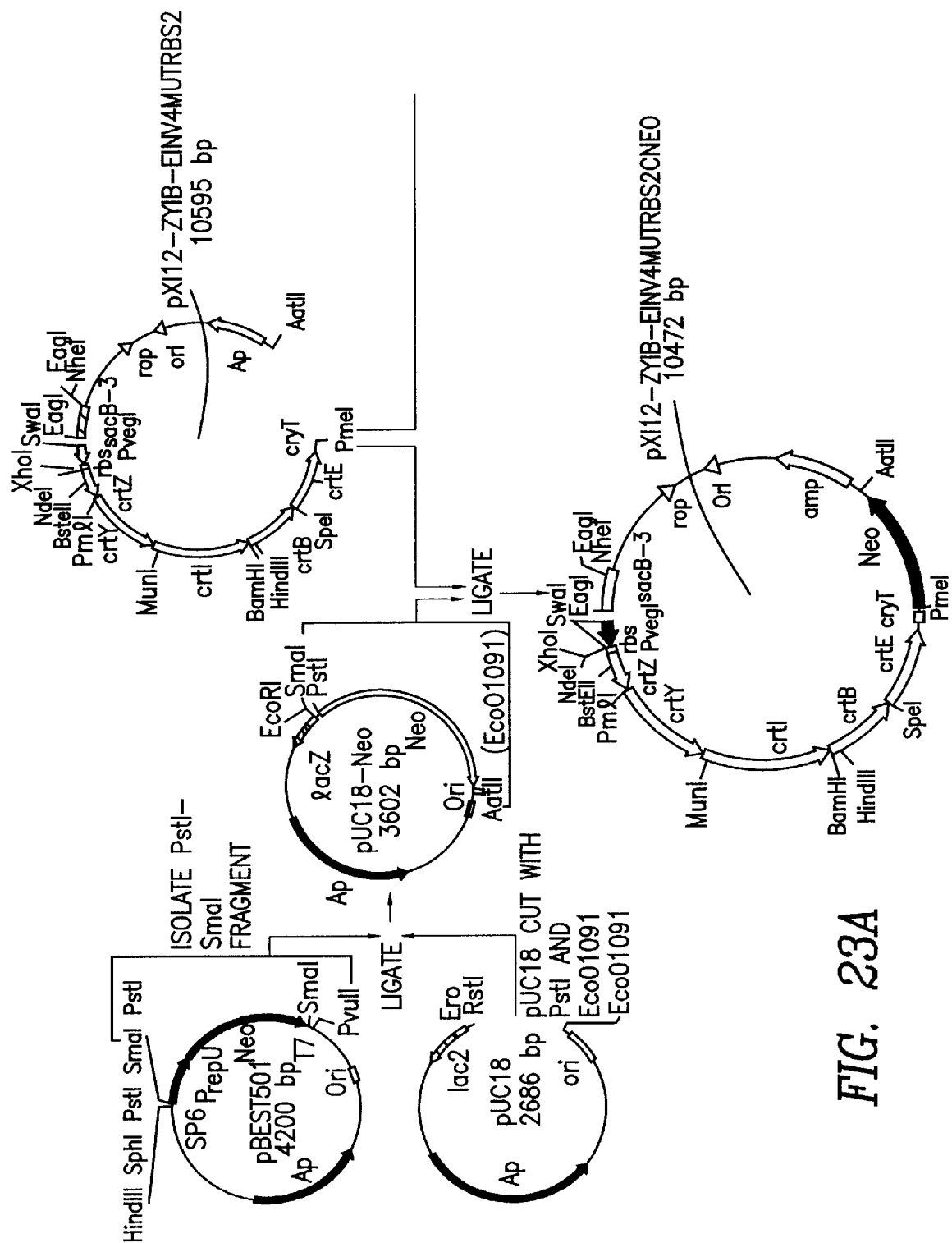
FIGS. 23A and 23B: Construction of plasmids pXI12-ZYIB-EINV4MUTRBS2CNEO and pXI12-ZYIB-EINV4MUTRB S2CCAT.
Figure 23B:
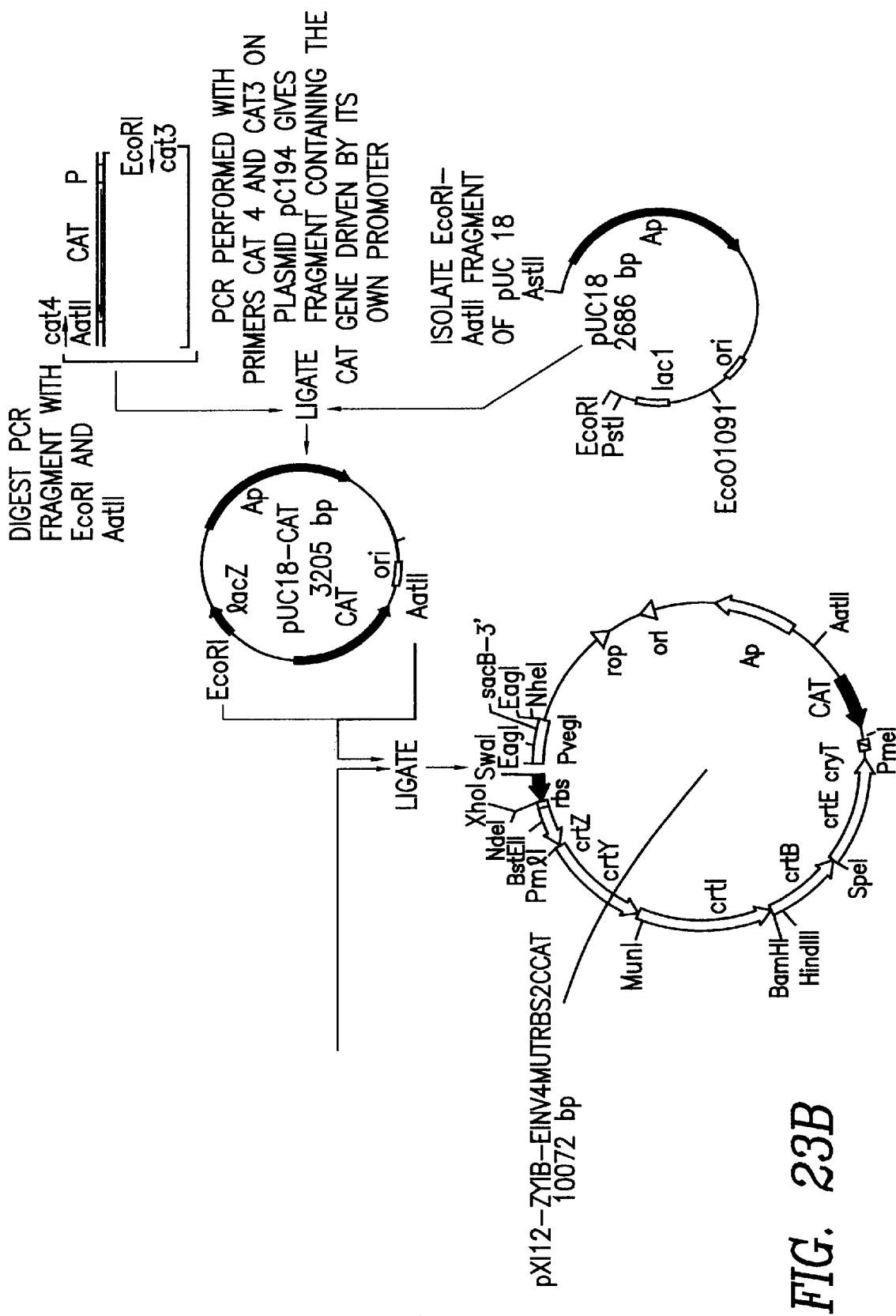

The final vector was obtained by replacing the PmeI-AatII fragment of pXI12-ZYIB-EINV4MUTRBS2C with the EcoRI-AatII fragment of pUC18-CAT, carrying the chloramphenicol resistance gene. FIG. 23 summarizes the different steps to obtain aforementioned constructs. Both plasmids were transformed into B. subtilis strain 1012, and transformants resulting from a Campbell-type integration were selected. Two strains BS1012::SFCONEO1 and BS1012::SFCOCAT1 were chosen for further amplification. Individual colonies of both strains were independently amplified by growing them in different concentrations of antibiotics as described in the methods section. For the cat gene carrying strain, the chloramphenicol concentrations were 60, 80, 120 and 150 mg/ml. For the neo gene carrying strain, the neomycin concentrations were 160 and 180 mg/ml. In both strains only strains with minor amplifications of the SFCO's were obtained. In daughter strains generated from strain BS1012::SFCONEO1, the resistance to higher neomycin concentrations correlated with the increase in the number of SFCO's in the chromosome and with higher levels of carotenoids produced by these cells. A different result was obtained with daughter strains obtained from strain BS1012::SFCOCAT1. In these strains an increase up to 150 μg chloramphenicol/ml resulted, as expected, in a higher number of SFCO copies in the chromosome.

EXAMPLE 7

Construction of CrtW Containing Plasmids and Use for Carotenoid Production

Polymerase chain reaction based gene synthesis. The nucleotide sequence of the artificial crtW gene, encoding the β-carotene β-4-oxygenase of Alcaligenes strain PC-1, was obtained by back translating the amino acid sequence outlined in Misawa, 1995, supra, using the BackTranslate program of the GCG Wisconsin Sequence Analysis Package, Version 8.0 (Genetics Computer Group, Madison, Wis., USA) and a codon frequency reference table of E. coli (supplied by the Bach Translate Program). The synthetic gene consisting of 726 nucleotides was constructed basically according to the method described by [Ye, 1992]. The sequence of the 12 oligonucleotides (crtW1–crtW12) required for the synthesis are shown in FIG. 25. Briefly, the long oligonucleotides were designed to have short overlaps of 15–20 bases, serving as primers for the extension of the oligonucleotides. After four cycles a few copies of the full length gene should be present which is then amplified by the two terminal oligonucleotides crtW15 and crtW26. The sequences for these two short oligonucleotides are for the forward primer crtW15 (5'-TATATCTAGAcat atgTCCGGTCGTAAA CCGG-3') [SEQ ID NO: 26] and for the reverse primer crtW26 (5'-TATAgaattccacgtgTCA AGCACGACCACCGGTTTTAC G-3') [SEQ ID NO: 27], where the sequences matching the DNA templates are underlined. Small cap letters show the introduced restriction sites (NdeI for the forward primer and EcoRI and PmlI for the reverse primer) for the latter cloning into the pALTER-Ex2 expression vector.

Polymerase chain reaction. All twelve long oligonucleotides (crtW1–crtW12; 7 nM each) and both terminal primers (crtW15 and crtW26; 0.1 mM each) were mixed and added to a PCR reaction mix containing Expand™ High Fidelity polymerase (Boehringer, Mannheim) (3.5 units) and dNTP's (100 mM each). The PCR reaction was run for 30 cycles with the following profile: 94° C. for 1 min, 50° C. for 2 min and 72° C. for 3 min. The PCR reaction was separated on a 1% agarose gel, and the band of approx. 700 bp was excised and purified using the glass beads method (Geneclean Kit, Bio101, Vista, Calif., USA). The fragment was subsequentely cloned into the SmaI site of plasmid pUC18, using the Sure-Clone Kit (Pharmacia, Uppsala, Sweden). The sequence of the resulting crtW synthetic gene was verified by sequencing with the Sequenase Kit Version 1.0 (United States Biochemical, Cleveland, Ohio, USA). The crtW gene constructed by this method was found to contain minor errors, which were subsequently corrected by site-directed mutagenesis.

Figure 26:
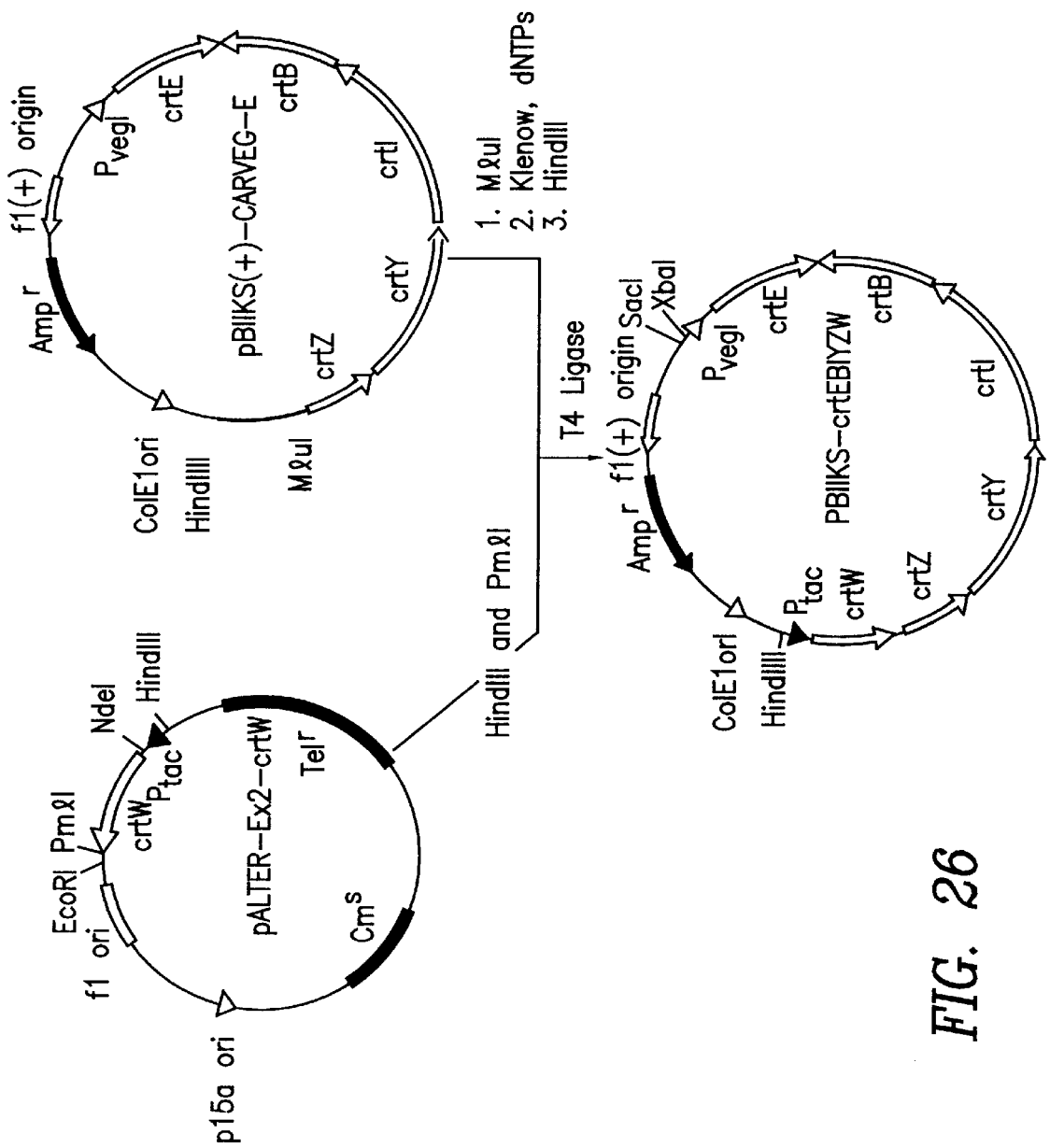
FIG. 26: Construction of plasmid pBIIKS-crtEBIYZW. The HindIII-Pm1I fragment of pALTER-Ex2-crtW, carrying the synthetic crtW gene, was cloned into the HindII and MluI (blunt) sites. PvegI and Ptac are the promoters used for the transcription of the two opera. The ColE1 replication origin of this plasmid is compatible with the p15A origin present in the pALTER-Ex2 constructs.

Construction of plasmids. Plasmid pBIIKS(+)-CARVEG-E (see also Example 5) (FIG. 26) contains the carotenoid biosynthesis genes (crtE, crtB, crtY, crtI and crtZ) of the Gram(−) bacterium Flavobacterium sp. strain R1534 WT [Pasamontes, 1995 supra] cloned into a modified pBluescript II KS(+) vector (Stratagene, La Jolla, USA) carrying site I of the B. subtilis veg promoter [LeGrice, 1986 supra]. This constitutive promoter has been shown to be functional in E. coli.

Figure 27:
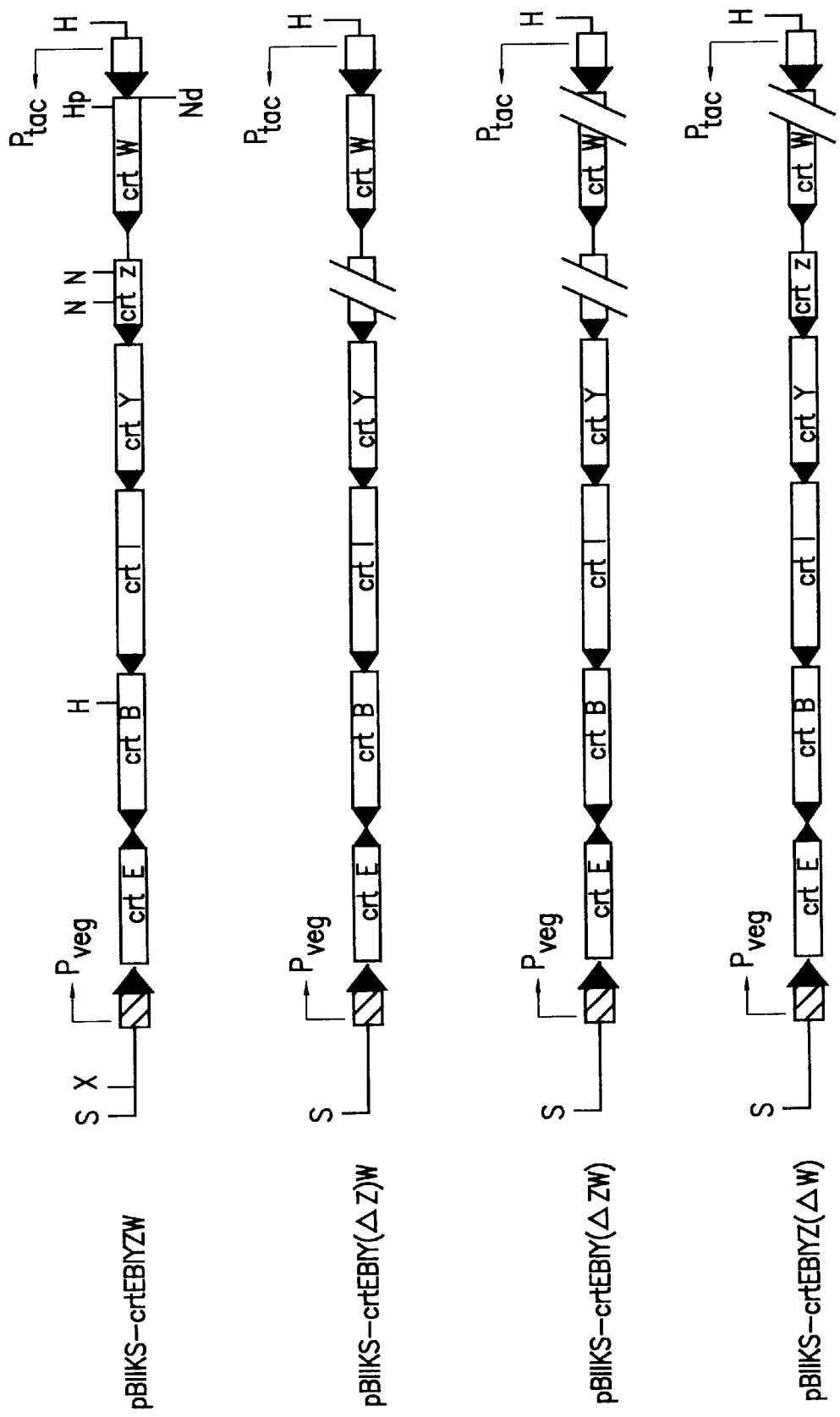
FIG. 27: Relevant inserts of all plasmids constructed in Example 7. Disrupted genes are shown by //. Restriction sites: S=SacI, X=XbaI, H=HindIII, N=NsiI, Hp=HpaI, Nd=NdeI.
Figure 28:
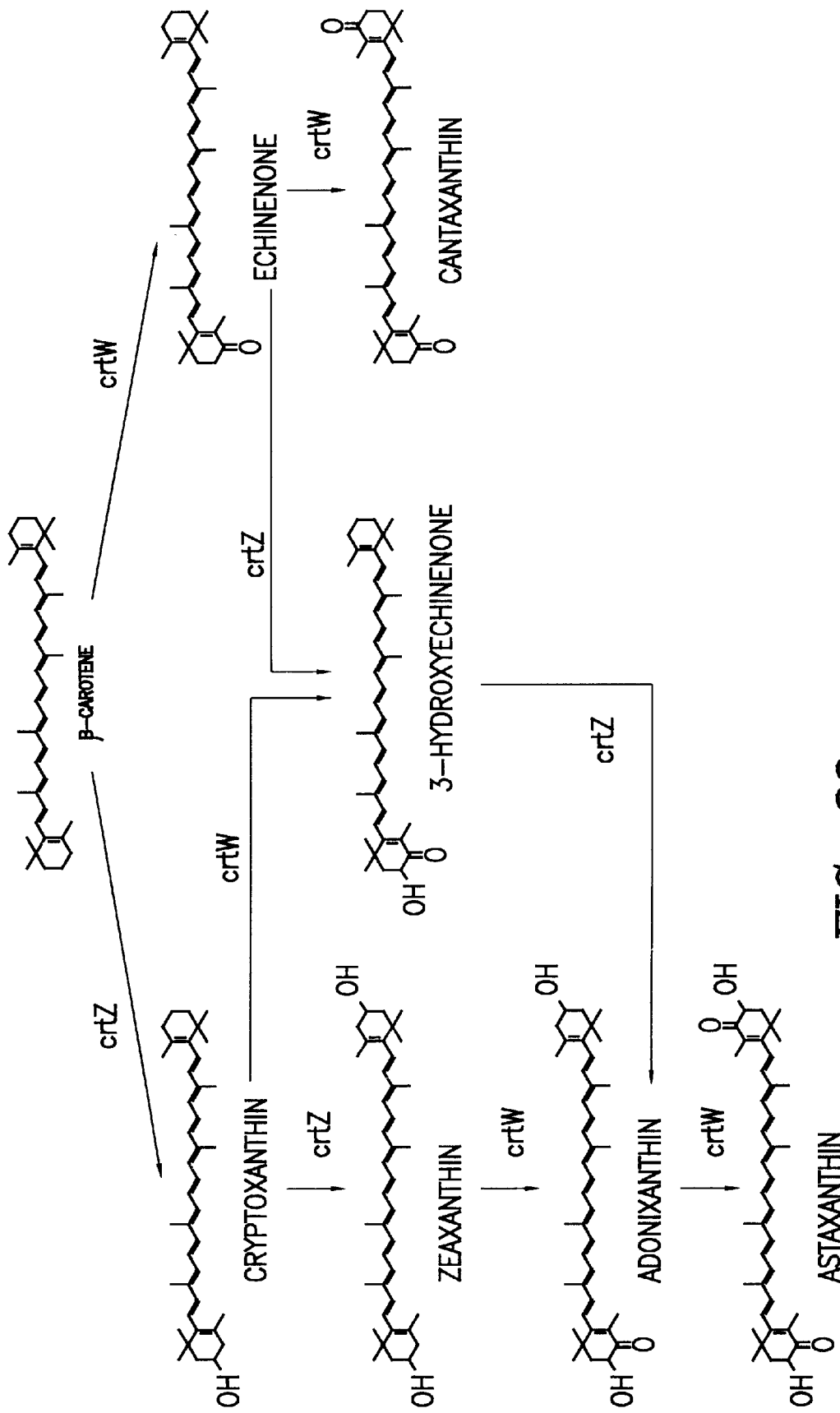
FIG. 28: Reaction products (carotenoids) obtained from β-carotene by the process of the present invention.

Transformants of E. coli strain TG1 carrying plasmid pBIIKS(+)-CARVEG-E synthesise zeaxanthin. Plasmid pALTER-Ex2-crtW was constructed by cloning the NdeI-EcoRI restricted fragment of the synthetic crtW gene into the corresponding sites of plasmid pALTER-Ex2 (Promega, Madison, Wis.). Plasmid pALTER-Ex2 is a low copy plasmid with the p15a origin of replication, which allows it to be maintained with ColE1 vectors in the same host. Plasmid pBIIKS-crtEBIYZW (FIG. 26) was obtained by cloning the HindIII-PmlI fragment of pALTER-Ex2-crtW into the HindIII and the blunt end made MluI site obtained by a fill in reaction with Klenow enzyme, as described elsewhere in [Sambrook, 1989 supra]. Inactivation of the crtZ gene was done by deleting a 285 bp NsiI-NsiI fragment, followed by a fill in reaction and religation, resulting in plasmid pBIIKS-crtEBIY[DZ]W. Plasmid pBIIKS-crtEBIY[DZW] carrying the non-functional genes crtW and crtZ, was constructed by digesting the plasmid pBIIKS-crtEBIY[DZ]W with NdeI and HpaI, and subsequent self religation of the plasmid after filling in the sites with Klenow enzyme. E. coli transformed with this plasmid had a yellow-orange colour due to the accumulation of b-carotene. Plasmid pBIIKS-crtEBIYZ[DW] has a truncated crtW gene obtained by deleting the NdeI-HpaI fragment in plasmid pBIIKS-crtEBIYZW as outlined above. Plasmids pALTER-Ex2-crtEBIY[DZW] and pALTER-Ex2-crtEBIYZ[DW], were obtained by isolating the BamHI-XbaI fragment from pBIIKS-crtEBIY [DZW] and pBIIKS-crtEBIYZ[DW], respectively and cloning them into the BamHI and XbaI sites of pALTER-Ex2. The plasmid pBIIKS-crtW was constructed by digesting pBIIKS-crtEBIYZW with NsiI and SacI, and self-religating the plasmid after recessing the DNA overhangs with Klenow enzyme. FIG. 27 compiles the relevant inserts of all the plasmids used in this paper.

Carotenoid analysis. E. coli TG-1 transformants carrying the different plasmid constructs were grown for 20 hours in Luria-Broth medium supplemented with antibiotics (ampicillin 100 μg/ml, tetracyclin 12.5 mg/ml) in shake flasks at 37° C. and 220 rpm. Carotenoids were extracted from the cells with acetone. The acetone was removed in vacuo and the residue was re dissolved in toluene. The coloured solutions were subjected to high-performance liquid chromatography (HPLC) analysis which was performed on a Hewlett-Packard series 1050 instrument. The carotenoids were separated on a silica column Nucleosil Si-100, 200×4 mm, 3 m. The solvent system included two solvents: hexane (A) and hexane/THF, 1:1 (B). A linear gradient was applied running from 13 to 50% (B) within 15 minutes. The flow rate was 1.5 ml/min. Peaks were detected at 450 nm by a photo diode array detector. The individual carotenoid pigments were identified by their absorption spectra and typical retention times as compared to reference samples of chemically pure carotenoids, prepared by chemical synthesis and characterised by NMR, MS and UV-Spectra. HPLC analysis of the pigments isolated from E. coli cells transformed with plasmid pBIIKS-crtEBIYZW, carrying besides the carotenoid biosynthesis genes of Flavobacterium sp. strain R1534, also the crtW gene encoding the b-carotene ketolase of Alcaligenes PC-1 [Misawa, 1995 supra] gave the following major peaks identified as: b-cryptoxanthin, astaxanthin, adonixanthin and zeaxanthin, based on the retention times and on the comparison of the absorbance spectra to given reference samples of chemically pure carotenoids. The relative amount (area percent) of the accumulated pigment in the E. coli transformant carrying pBIIKS-crtEBIYZW is shown in Table 3.["CRX": cryptoxanthin; "ASX": astaxanthin; "ADX": adonixanthin; "ZXN": zeaxanthin; "ECM": echinenone; "MECH": 3-hydroxyechinenone, "CXN": cantaxanthin]. The Σ of the peak areas of all identified carotenoids was defined as 100%. Numbers shown in Table 3 represent the average value of four independent cultures for each transformant. In contrast to the aforementioned results, E. coli transformants carrying the same genes but on two plasmids namely, pBIIKS-crtEBIYZ[ΔW] and pALTER-Ex2-crtW, showed a drastical drop in adonixanthin and a complete lack of astaxanthin pigments (Table 3), whereas the relative amount of zeaxanthin (%) had increased. Echinenone, hydroxyechinenone and canthaxanthin levels remained unchanged compared to the transformants carrying all the crt genes on the same plasmid (pBIIKS-crtEBIYZW). Plasmid pBIIKS-crtEBIYZ [ΔW] is a high copy plasmid carrying the functional genes of crtE, crtB, crtY, crtI, crtZ of Flavobacterium sp. strain R1534 and a truncated, non-functional version of the crtW gene, whereas the functional copy of the crtW gene is located on the low copy plasmid pALTER-Ex2-crtW. To analyze the effect of overexpression of the crtW gene with respect to the crtZ gene, E. coli cells were co-transformed with plasmid pBIIKS-crtW carrying the crtW gene on the high copy plasmid pBIIKS-crtW and the low copy construct pALTER-Ex2-crtEBIYZ[ΔW], encoding the Flavobacterium crt genes. Pigment analysis of these transformants by HPLC monitored the presence of b-carotene, cryptoxanthin, astaxanthin, adonixanthin, zeaxanthin, 3-hydroxyechinenone and minute traces of echinenone and canthaxanthin (Table 3).

Transformants harbouring the crtW gene on the low copy plasmid pALTER-Ex2-crtW and the genes crtE, crtB, crtY and crtI on the high copy plasmid pBIIKS-crtEBIY[ΔZW] expressed only minor amounts of canthaxanthin (6%) but high levels of echinenone (94%), whereas cells carrying the crtW gene on the high copy plasmid pBIIKS-crtW and the other crt genes on the low copy construct pALTER-Ex2-crtEBIY[ΔZW], had 78.6% and 21.4% of echinenone and canthaxanthin, respectively (Table 3).

TABLE 3

| plasmids | CRX | ASX | ADX | ZXN | ECH | HECH | CXN |
|---|---|---|---|---|---|---|---|
| pBIIKS-crtEBIYZW | 1.1 | 2.0 | 44.2 | 52.4 | <1 | <1 | <1 |
| pBIIKS-crtEBIYZ[ΔW] + pALTER-Ex2-crtW | 2.2 | — | 25.4 | 72.4 | <1 | <1 | <1 |
| pBIIKS-crtEBIY[ΔZ]W | — | — | — | — | 66.5 | — | 33.5 |
| pBIIKS-crtEBIY[ΔZW] + pALTER-Ex2-crtW | — | — | — | — | 94 | — | 6 |
| pALTER-Ex2-crtEBIY[ΔZW] + pBIIKS-crtW | | | | | 78.6 | | 21.4 |

SEQUENCE LISTING (1) GENERAL INFORMATION:

(iii) NUMBER OF SEQUENCES: 47

(2) INFORMATION FOR SEQ ID NO: 1:

(i) SEQUENCE CHARACTERISTICS:
      (A) LENGTH: 295 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO: 1:

```
Met Thr Pro Lys Gln Gln Phe Pro Leu Arg Asp Leu Val Glu Ile Arg
 1               5                  10                  15

Leu Ala Gln Ile Ser Gly Gln Phe Gly Val Val Ser Ala Pro Leu Gly
            20                  25                  30

Ala Ala Met Ser Asp Ala Ala Leu Ser Pro Gly Lys Arg Phe Arg Ala
            35                  40                  45

Val Leu Met Leu Met Val Ala Glu Ser Ser Gly Gly Val Cys Asp Ala
 50                  55                  60

Met Val Asp Ala Ala Cys Ala Val Glu Met Val His Ala Ala Ser Leu
 65                  70                  75                  80

Ile Phe Asp Asp Met Pro Cys Met Asp Asp Ala Arg Thr Arg Arg Gly
            85                  90                  95

Gln Pro Ala Thr His Val Ala His Gly Glu Gly Arg Ala Val Leu Ala
            100                 105                 110

Gly Ile Ala Leu Ile Thr Glu Ala Met Arg Ile Leu Gly Glu Ala Arg
            115                 120                 125

Gly Ala Thr Pro Asp Gln Arg Ala Arg Leu Val Ala Ser Met Ser Arg
            130                 135                 140

Ala Met Gly Pro Val Gly Leu Cys Ala Gly Gln Asp Leu Asp Leu His
145                 150                 155                 160

Ala Pro Lys Asp Ala Ala Gly Ile Glu Arg Glu Gln Asp Leu Lys Thr
                165                 170                 175

Gly Val Leu Phe Val Ala Gly Leu Glu Met Leu Ser Ile Ile Lys Gly
            180                 185                 190
```

```
Leu Asp Lys Ala Glu Thr Glu Gln Leu Met Ala Phe Gly Arg Gln Leu
            195                 200                 205

Gly Arg Val Phe Gln Ser Tyr Asp Asp Leu Leu Asp Val Ile Gly Asp
        210                 215                 220

Lys Ala Ser Thr Gly Lys Asp Thr Ala Arg Asp Thr Ala Ala Pro Gly
225                 230                 235                 240

Pro Lys Gly Gly Leu Met Ala Val Gly Gln Met Gly Asp Val Ala Gln
                245                 250                 255

His Tyr Arg Ala Ser Arg Ala Gln Leu Asp Glu Leu Met Arg Thr Arg
            260                 265                 270

Leu Phe Arg Gly Gly Gln Ile Ala Asp Leu Leu Ala Arg Val Leu Pro
            275                 280                 285

His Asp Ile Arg Arg Ser Ala
        290                 295

(2) INFORMATION FOR SEQ ID NO: 2:

(i) SEQUENCE CHARACTERISTICS:
        (A) LENGTH: 888 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 2:

ATGACGCCCA AGCAGCAATT CCCCCTACGC GATCTGGTCG AGATCAGGCT GGCGCAGATC      60

TCGGGCCAGT TCGGCGTGGT CTCGGCCCCG CTCGGCGCGG CCATGAGCGA TGCCGCCCTG     120

TCCCCCGGCA AACGCTTTCG CGCCGTGCTG ATGCTGATGG TCGCCGAAAG CTCGGGCGGG     180

GTCTGCGATG CGATGGTCGA TGCCGCCTGC GCGGTCGAGA TGGTCCATGC CGCATCGCTG     240

ATCTTCGACG ACATGCCCTG CATGGACGAT GCCAGGACCC GTCGCGGTCA GCCCGCCACC     300

CATGTCGCCC ATGGCGAGGG CGCGCGGTG CTTGCGGGCA TCGCCCTGAT CACCGAGGCC      360

ATGCGGATTT TGGGCGAGGC GCGCGGCGCG ACGCCGGATC AGCGCGCAAG GCTGGTCGCA     420

TCCATGTCGC GCGCGATGGG ACCGGTGGGG CTGTGCGCAG GCAGGATCT GGACCTGCAC      480

GCCCCCAAGG ACGCCGCCGG GATCGAACGT GAACAGGACC TCAAGACCGG CGTGCTGTTC     540

GTCGCGGGCC TCGAGATGCT GTCCATTATT AAGGGTCTGG ACAAGGCCGA GACCGAGCAG     600

CTCATGGCCT TCGGCGTCA GCTTGGTCGG GTCTTCCAGT CCTATGACGA CCTGCTGGAC      660

GTGATCGGCG ACAAGGCCAG CACCGGCAAG GATACGGCGC GCGACACCGC CGCCCCCGGC     720

CCAAAGGGCG GCCTGATGGC GGTCGGACAG ATGGGCGACG TGGCGCAGCA TTACCGCGCC     780

AGCCGCGCGC AACTGGACGA GCTGATGCGC ACCCGGCTGT TCCGCGGGGG GCAGATCGCG     840

GACCTGCTGG CCCGCGTGCT GCCGCATGAC ATCCGCCGCA GCGCCTAG                  888

(2) INFORMATION FOR SEQ ID NO: 3:

(i) SEQUENCE CHARACTERISTICS:
        (A) LENGTH: 303 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 3:

Met Thr Asp Leu Thr Ala Thr Ser Glu Ala Ala Ile Ala Gln Gly Ser
1               5                   10                  15
```

```
Gln Ser Phe Ala Gln Ala Ala Lys Leu Met Pro Pro Gly Ile Arg Glu
            20                  25                  30

Asp Thr Val Met Leu Tyr Ala Trp Cys Arg His Ala Asp Asp Val Ile
            35                  40                  45

Asp Gly Gln Val Met Gly Ser Ala Pro Glu Ala Gly Gly Asp Pro Gln
            50                  55                  60

Ala Arg Leu Gly Ala Leu Arg Ala Asp Thr Leu Ala Ala Leu His Glu
65                  70                  75                  80

Asp Gly Pro Met Ser Pro Pro Phe Ala Leu Arg Gln Val Ala Arg
                    85                  90                  95

Arg His Asp Phe Pro Asp Leu Trp Pro Met Asp Leu Ile Glu Gly Phe
                    100                 105                 110

Ala Met Asp Val Ala Asp Arg Glu Tyr Arg Ser Leu Asp Asp Val Leu
                    115                 120                 125

Glu Tyr Ser Tyr His Val Ala Gly Val Val Gly Val Met Met Ala Arg
                    130                 135                 140

Val Met Gly Val Gln Asp Asp Ala Val Leu Asp Arg Ala Cys Asp Leu
145                 150                 155                 160

Gly Leu Ala Phe Gln Leu Thr Asn Ile Ala Arg Asp Val Ile Asp Asp
                    165                 170                 175

Ala Ala Ile Gly Arg Cys Tyr Leu Pro Ala Asp Trp Leu Ala Glu Ala
                    180                 185                 190

Gly Ala Thr Val Glu Gly Pro Val Pro Ser Asp Ala Leu Tyr Ser Val
                    195                 200                 205

Ile Ile Arg Leu Leu Asp Ala Ala Glu Pro Tyr Tyr Ala Ser Ala Arg
210                 215                 220

Gln Gly Leu Pro His Leu Pro Pro Arg Cys Ala Trp Ser Ile Ala Ala
225                 230                 235                 240

Ala Leu Arg Ile Tyr Arg Ala Ile Gly Thr Arg Ile Arg Gln Gly Gly
                    245                 250                 255

Pro Glu Ala Tyr Arg Gln Arg Ile Ser Thr Ser Lys Ala Ala Lys Ile
                    260                 265                 270

Gly Leu Leu Ala Arg Gly Gly Leu Asp Ala Ala Ser Arg Leu Arg
                    275                 280                 285

Gly Gly Glu Ile Ser Arg Asp Gly Leu Trp Thr Arg Pro Arg Ala
                    290                 295                 300
```

(2) INFORMATION FOR SEQ ID NO: 4:

(i) SEQUENCE CHARACTERISTICS:
        (A) LENGTH: 908 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 4:

```
ATGACCGATC TGACGGCGAC TTCCGAAGCG GCCATCGCGC AGGGTTCGCA AAGCTTCGCG     60

CAGGCGGCCA AGCTGATGCC GCCCGGCATC CGCGAGGATA CGGTCATGCT CTATGCCTGG    120

TGCAGGCATG CGGATGACGT GATCGACGGG CAGGTGATGG GTTCTGCCCC CGAGGCGGGC    180

GGCGACCCAC AGGCGCGGCT GGGGGCGCTG CGCGCCGACA CGCTGGCCGC GCTGCACGAG    240

GACGGCCCGA TGTCGCCGCC CTTCGCGGCG CTGCGCCAGG TCGCCCGGCG GCATGATTTC    300

CCGGACCTTT GGCCGATGGA CCTGATCGAG GGTTTCGCGA TGGATGTCGC GGATCGCGAA    360
```

-continued

```
TACCGCAGCC TGGATGACGT GCTGGAATAT TCCTACCACG TCGCGGGGGT CGTGGGCGTG      420

ATGATGGCGC GGGTGATGGG CGTGCAGGAC GATGCGGTGC TGGATCGCGC CTGCGATCTG      480

GGCCTTGCGT TCCAGCTGAC GAACATCGCT CGCGACGTGA TCGACGATGC CGCCATCGGG      540

CGCTGCTATC TGCCTGCCGA CTGGCTGGCC GAGGCGGGGG CGACGGTTGA GGGTCCGGTG      600

CCTTCGGACG CGCTCTATTC CGTCATCATC CGCCTGCTTG ACGCGGCCGA GCCCTATTAT      660

GCCTCGGCGC GGCAGGGGCT TCCGCATCTG CCGCCGCGCT GCGCGTGGTC GATCGCCGCC      720

GCGCTGCGTA TCTATCGCGC AATCGGGACG CGCATCCGGC AGGGTGGCCC CGAGGCCTAT      780

CGCCAGCGGA TCAGCACGTC GAAGGCTGCC AAGATCGGGC TTCTGGCGCG CGGAGGCTTG      840

GACGCGGCCG CATCGCGCCT GCGCGGCGGC GAAATCAGCC GCGACGGCCT GTGGACCCGA      900

CCGCGCGC                                                              908
```

(2) INFORMATION FOR SEQ ID NO: 5:

(i) SEQUENCE CHARACTERISTICS:
      (A) LENGTH: 494 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO: 5:

```
Met Ser Ser Ala Ile Val Ile Gly Ala Gly Phe Gly Gly Leu Ala Leu
1               5                   10                  15

Ala Ile Arg Leu Gln Ser Ala Gly Ile Ala Thr Thr Ile Val Glu Ala
            20                  25                  30

Arg Asp Lys Pro Gly Gly Arg Ala Tyr Val Trp Asn Asp Gln Gly His
        35                  40                  45

Val Phe Asp Ala Gly Pro Thr Val Val Thr Asp Pro Asp Ser Leu Arg
    50                  55                  60

Glu Leu Trp Ala Leu Ser Gly Gln Pro Met Glu Arg Asp Val Thr Leu
65                  70                  75                  80

Leu Pro Val Ser Pro Phe Tyr Arg Leu Thr Trp Ala Asp Gly Arg Ser
                85                  90                  95

Phe Glu Tyr Val Asn Asp Asp Glu Leu Ile Arg Gln Val Ala Ser
            100                 105                 110

Phe Asn Pro Ala Asp Val Asp Gly Tyr Arg Arg Phe His Asp Tyr Ala
        115                 120                 125

Glu Glu Val Tyr Arg Glu Gly Tyr Leu Lys Leu Gly Thr Thr Pro Phe
    130                 135                 140

Leu Lys Leu Gly Gln Met Leu Asn Ala Ala Pro Ala Leu Met Arg Leu
145                 150                 155                 160

Gln Ala Tyr Arg Ser Val His Ser Met Val Ala Arg Phe Ile Gln Asp
                165                 170                 175

Pro His Leu Arg Gln Ala Phe Ser Phe His Thr Leu Leu Val Gly Gly
            180                 185                 190

Asn Pro Phe Ser Thr Ser Ser Ile Tyr Ala Leu Ile His Ala Leu Glu
        195                 200                 205

Arg Arg Gly Gly Val Trp Phe Ala Lys Gly Gly Thr Asn Gln Leu Val
    210                 215                 220

Ala Gly Met Val Ala Leu Phe Glu Arg Leu Gly Gly Thr Leu Leu Leu
225                 230                 235                 240
```

-continued

```
Asn Ala Arg Val Thr Arg Ile Asp Thr Glu Gly Asp Arg Ala Thr Gly
                245                 250                 255

Val Thr Leu Leu Asp Gly Arg Gln Leu Arg Ala Asp Thr Val Ala Ser
            260                 265                 270

Asn Gly Asp Val Met His Ser Tyr Arg Asp Leu Leu Gly His Thr Arg
        275                 280                 285

Arg Gly Arg Thr Lys Ala Ala Ile Leu Asn Arg Gln Arg Trp Ser Met
    290                 295                 300

Ser Leu Phe Val Leu His Phe Gly Leu Ser Lys Arg Pro Glu Asn Leu
305                 310                 315                 320

Ala His His Ser Val Ile Phe Gly Pro Arg Tyr Lys Gly Leu Val Asn
                325                 330                 335

Glu Ile Phe Asn Gly Pro Arg Leu Pro Asp Asp Phe Ser Met Tyr Leu
            340                 345                 350

His Ser Pro Cys Val Thr Asp Pro Ser Leu Ala Pro Glu Gly Met Ser
        355                 360                 365

Thr His Tyr Val Leu Ala Pro Val Pro His Leu Gly Arg Ala Asp Val
    370                 375                 380

Asp Trp Glu Ala Glu Ala Pro Gly Tyr Ala Glu Arg Ile Phe Glu Glu
385                 390                 395                 400

Leu Glu Arg Arg Ala Ile Pro Asp Leu Arg Lys His Leu Thr Val Ser
                405                 410                 415

Arg Ile Phe Ser Pro Ala Asp Phe Ser Thr Glu Leu Ser Ala His His
            420                 425                 430

Gly Ser Ala Phe Ser Val Glu Pro Ile Leu Thr Gln Ser Ala Trp Phe
        435                 440                 445

Arg Pro His Asn Arg Asp Arg Ala Ile Pro Asn Phe Tyr Ile Val Gly
    450                 455                 460

Ala Gly Thr His Pro Gly Ala Gly Ile Pro Gly Val Val Gly Ser Ala
465                 470                 475                 480

Lys Ala Thr Ala Gln Val Met Leu Ser Asp Leu Ala Val Ala
                485                 490
```

(2) INFORMATION FOR SEQ ID NO: 6:

(i) SEQUENCE CHARACTERISTICS:
        (A) LENGTH: 1482 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 6:

```
ATGAGTTCCG CCATCGTCAT CGGCGCAGGT TTCGGCGGGC TTGCGCTTGC CATCCGCCTG      60

CAATCGGCCG GCATCGCGAC CACCATCGTC GAGGCCCGCG ACAAGCCCGG CGGCCGCGCC     120

TATGTCTGGA ACGATCAGGG CCACGTCTTC GATGCAGGCC CGACGGTCGT GACCGACCCC     180

GACAGCCTGC GAGAGCTGTG GGCCCTCAGC GGCCAACCGA TGGAGCGTGA CGTGACGCTG     240

CTGCCGGTCT CGCCCTTCTA CCGGCTGACA TGGGCGGACG GCCGCAGCTT CGAATACGTG     300

AACGACGACG ACGAGCTGAT CCGCCAGGTC GCCTCCTTCA ATCCCGCCGA TGTCGATGGC     360

TATCGCCGCT TCCACGATTA CGCCGAGGAG GTCTATCGCG AGGGGTATCT GAAGCTGGGG     420

ACCACGCCCT TCCTGAAGCT GGGCCAGATG CTGAACGCCG CGCCGGCGCT GATGCGCCTG     480

CAGGCATACC GCTCGGTCCA GCATGGTGTG GCGCGCTTCA TCCAGGACCC GCATCTGCGG     540
```

-continued

```
CAGGCCTTCT CGTTCCACAC GCTGCTGGTC GGCGGGAACC CGTTTTCGAC CAGCTCGATC      600

TATGCGCTGA TCCATGCGCT GGAACGGCGC GGCGGCGTCT GGTTCGCCAA GGGCGGCACC      660

AACCAGCTGG TCGCGGGCAT GGTCGCCCTG TTCGAGCGTC TTGGCGGCAC GCTGCTGCTG      720

AATGCCCGCG TCACGCGGAT CGACACCGAG GGCGATCGCG CCACGGGCGT CACGCTGCTG      780

GACGGGCGGC AGTTGCGCGC GGATACGGTG GCCAGCAACG GCGACGTGAT GCACAGCTAT      840

CGCGACCTGC TGGGCCATAC CCGCCGCGGG CGCACCAAGG CCGCGATCCT GAACCGGCAG      900

CGCTGGTCGA TGTCGCTGTT CGTGCTGCAT TTCGGCCTGT CCAAGCGCCC CGAGAACCTG      960

GCCCACCACA GCGTCATCTT CGGCCCGCGC TACAAGGGGC TGGTGAACGA GATCTTCAAC     1020

GGGCCACGCC TGCCGGACGA TTTCTCGATG TATCTGCATT CGCCCTGCGT GACCGATCCC     1080

AGCCTGGCCC CCGAGGGGAT GTCCACGCAT TACGTCCTTG CGCCCGTTCC GCATCTGGGC     1140

CGCGCCGATG TCGATTGGGA AGCCGAGGCC CCGGGCTATG CCGAGCGCAT CTTCGAGGAA     1200

CTGGAGCGCC GCGCCATCCC CGACCTGCGC AAGCACCTGA CCGTCAGCCG CATCTTCAGC     1260

CCCGCCGATT TCAGCACCGA ACTGTCGGCC CATCACGGCA GCGCCTTCTC GGTCGAGCCG     1320

ATCCTGACGC AATCCGCCTG GTTCCGCCCG CATAACCGCG ACCGCGCGAT CCCGAACTTC     1380

TACATCGTGG GGCGGGCAC GCATCCGGGT GCGGGCATCC CGGGTGTCGT TGGCAGCGCC     1440

AAGGCCACGG CGCAGGTCAT GCTGTCGGAC CTGGCCGTCG CA                       1482
```

(2) INFORMATION FOR SEQ ID NO: 7:

(i) SEQUENCE CHARACTERISTICS:
        (A) LENGTH: 382 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 7:

```
Met Ser His Asp Leu Leu Ile Ala Gly Ala Gly Leu Ser Gly Ala Leu
1               5                   10                  15

Ile Ala Leu Ala Val Arg Asp Arg Arg Pro Asp Ala Arg Ile Val Met
                20                  25                  30

Leu Asp Ala Arg Ser Gly Pro Ser Asp Gln His Thr Trp Ser Cys His
            35                  40                  45

Asp Thr Asp Leu Ser Pro Glu Trp Leu Ala Arg Leu Ser Pro Ile Arg
50                  55                  60

Arg Gly Glu Trp Thr Asp Gln Glu Val Ala Phe Pro Asp His Ser Arg
65                  70                  75                  80

Arg Leu Thr Thr Gly Tyr Gly Ser Ile Glu Ala Gly Ala Leu Ile Gly
                85                  90                  95

Leu Leu Gln Gly Val Asp Leu Arg Trp Asn Thr His Val Ala Thr Leu
            100                 105                 110

Asp Asp Thr Gly Ala Thr Leu Thr Asp Gly Ser Arg Ile Glu Ala Ala
        115                 120                 125

Cys Val Ile Asp Ala Arg Gly Ala Val Glu Thr Pro His Leu Thr Val
    130                 135                 140

Gly Phe Gln Lys Phe Val Gly Val Glu Ile Glu Thr Asp Ala Pro His
145                 150                 155                 160

Gly Val Glu Arg Pro Met Ile Met Asp Ala Thr Val Pro Gln Met Asp
                165                 170                 175

Gly Tyr Arg Phe Ile Tyr Leu Leu Pro Phe Ser Pro Thr Arg Ile Leu
```

```
                180                  185                  190
Ile Glu Asp Thr Arg Tyr Ser Asp Gly Gly Asp Leu Asp Asp Gly Ala
            195                  200                  205

Leu Ala Gln Ala Ser Leu Asp Tyr Ala Ala Arg Arg Gly Trp Thr Gly
        210                  215                  220

Gln Glu Met Arg Arg Glu Arg Gly Ile Leu Pro Ile Ala Leu Ala His
225                  230                  235                  240

Asp Ala Ile Gly Phe Trp Arg Asp His Ala Gln Gly Ala Val Pro Val
                245                  250                  255

Gly Leu Gly Ala Gly Leu Phe His Pro Val Thr Gly Tyr Ser Leu Pro
            260                  265                  270

Tyr Ala Ala Gln Val Ala Asp Ala Ile Ala Ala Arg Asp Leu Thr Thr
        275                  280                  285

Ala Ser Ala Arg Arg Ala Val Arg Gly Trp Ala Ile Asp Arg Ala Asp
290                  295                  300

Arg Asp Arg Phe Leu Arg Leu Leu Asn Arg Met Leu Phe Arg Gly Cys
305                  310                  315                  320

Pro Pro Asp Arg Arg Tyr Arg Leu Leu Gln Arg Phe Tyr Arg Leu Pro
                325                  330                  335

Gln Pro Leu Ile Glu Arg Phe Tyr Ala Gly Arg Leu Thr Leu Ala Asp
            340                  345                  350

Arg Leu Arg Ile Val Thr Gly Arg Pro Pro Ile Pro Leu Ser Gln Ala
        355                  360                  365

Val Arg Cys Leu Pro Glu Arg Pro Leu Leu Gln Glu Arg Ala
370                  375                  380
```

(2) INFORMATION FOR SEQ ID NO: 8:

(i) SEQUENCE CHARACTERISTICS:
        (A) LENGTH: 1149 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 8:

```
ATGAGCCATG ATCTGCTGAT CGCGGGCGCG GGGCTGTCCG GTGCGCTGAT CGCGCTTGCC    60
GTTCGCGACC GCAGACCGGA TGCGCGCATC GTGATGCTCG ACGCGCGGTC CGGCCCCTCG   120
GACCAGCACA CCTGGTCCTG CCACGACACG GATCTTTCGC CCGAATGGCT GGCGCGCCTG   180
TCGCCCATTC GTCGCGGCGA ATGGACGGAT CAGGAGGTCG CGTTTCCCGA CCATTCGCGC   240
CGCCTGACGA CAGGCTATGG CTCGATCGAG GCGGGCGCGC TGATCGGGCT GCTGCAGGGT   300
GTCGATCTGC GGTGGAATAC GCATGTCGCG ACGCTGGACG ATACCGGCGC GACGCTGACG   360
GACGGCTCGC GGATCGAGGC TGCCTGCGTG ATCGACGCCC GTGGTGCCGT CGAGACCCCG   420
CACCTGACCG TGGGTTTCCA GAAATTCGTG GGCGTCGAGA TCGAGACCGA CGCCCCCCAT   480
GGCGTCGAGC GCCCGATGAT CATGGACGCG ACCGTTCCGC AGATGGACGG GTACCGCTTC   540
ATCTATCTGC TGCCCTTCAG TCCCACCCGC ATCCTGATCG AGGATACGCG CTACAGCGAC   600
GGCGGCGATC TGGACGATGG CGCGCTGGCG CAGGCGTCGC TGGACTATGC CGCCAGGCGG   660
GGCTGGACCG GCAGGAGAT GCGGCGCGAA AGGGGCATCC TGCCCATCGC GCTGGCCCAT   720
GACGCCATAG GCTTCTGGCG CGACCACGCG CAGGGGCGG TGCCGGTTGG CTGGGGGCA   780
GGGCTGTTCC ACCCCGTCAC CGGATATTCG CTGCCCTATG CCGCGCAGGT CGCGGATGCC   840
```

```
ATCGCGGCGC GCGACCTGAC GACCGCGTCC GCCCGTCGCG CGGTGCGCGG CTGGGCCATC      900

GATCGCGCGG ATCGCGACCG CTTCCTGCGG CTGCTGAACC GGATGCTGTT CCGCGGCTGC      960

CCGCCCGACC GTCGCTATCG CCTGCTGCAG CGGTTCTACC GCCTGCCGCA GCCGCTGATC     1020

GAGCGCTTCT ATGCCGGGCG CCTGACATTG GCCGACCGGC TTCGCATCGT CACCGGACGC     1080

CCGCCCATTC CGCTGTCGCA GGCCGTGCGC TGCCTGCCCG AACGCCCCCT GCTGCAGGAG     1140

AGAGCATGA                                                             1149
```

(2) INFORMATION FOR SEQ ID NO: 9:

(i) SEQUENCE CHARACTERISTICS:
        (A) LENGTH: 169 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 9:

```
Met Ser Thr Trp Ala Ala Ile Leu Thr Val Ile Leu Thr Val Ala Ala
  1               5                  10                  15

Met Glu Leu Thr Ala Tyr Ser Val His Arg Trp Ile Met His Gly Pro
                 20                  25                  30

Leu Gly Trp Gly Trp His Lys Ser His His Asp Glu Asp His Asp His
             35                  40                  45

Ala Leu Glu Lys Asn Asp Leu Tyr Gly Val Ile Phe Ala Val Ile Ser
         50                  55                  60

Ile Val Leu Phe Ala Ile Gly Ala Met Gly Ser Asp Leu Ala Trp Trp
 65                  70                  75                  80

Leu Ala Val Gly Val Thr Cys Tyr Gly Leu Ile Tyr Tyr Phe Leu His
                 85                  90                  95

Asp Gly Leu Val His Gly Arg Trp Pro Phe Arg Tyr Val Pro Lys Arg
                100                 105                 110

Gly Tyr Leu Arg Arg Val Tyr Gln Ala His Arg Met His His Ala Val
            115                 120                 125

His Gly Arg Glu Asn Cys Val Ser Phe Gly Phe Ile Trp Ala Pro Ser
        130                 135                 140

Val Asp Ser Leu Lys Ala Glu Leu Lys Arg Ser Gly Ala Leu Leu Lys
145                 150                 155                 160

Asp Arg Glu Gly Ala Asp Arg Asn Thr
                165
```

(2) INFORMATION FOR SEQ ID NO: 10:

(i) SEQUENCE CHARACTERISTICS:
        (A) LENGTH: 506 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 10:

```
ATGAGCACTT GGGCCGCAAT CCTGACCGTC ATCCTGACCG TCGCCGCGAT GGAGCTGACG       60

GCCTACTCCG TCCATCGGTG GATCATGCAT GGCCCCCTGG GCTGGGGCTG GCATAAATCG      120

CACCACGACG AGGATCACGA CCACGCGCTC GAGAAGAACG ACCTCTATGG CGTCATCTTC      180

GCGGTAATCT CGATCGTGCT GTTCGCGATC GGCGCGATGG GGTCGGATCT GGCCTGGTGG      240
```

-continued

```
CTGGCGGTGG GGGTCACCTG CTACGGGCTG ATCTACTATT TCCTGCATGA CGGCTTGGTG      300

CATGGGCGCT GGCCGTTCCG CTATGTCCCC AAGCGCGGCT ATCTTCGTCG CGTCTACCAG      360

GCACACAGGA TGCATCACGC GGTCCATGGC CGCGAGAACT GCGTCAGCTT CGGTTTCATC      420

TGGGCGCCCT CGGTCGACAG CCTCAAGGCA GAGCTGAAAC GCTCGGGCGC GCTGCTGAAG      480

GACCGCGAAG GGGCGGATCG CAATAC                                          506
```

(2) INFORMATION FOR SEQ ID NO: 11:

(i) SEQUENCE CHARACTERISTICS:
        (A) LENGTH: 726 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 11:

```
ATGTCCGGTC GTAAACCGGG TACCACCGGT GACACCATCG TTAACCTGGG TCTGACCGCT       60

GCTATCCTGC TGTGCTGGCT GGTTCTGCAC GCTTTCACCC TGTGGCTGCT GGACGCTGCT      120

GCTCACCCGC TGCTGGCTGT TCTGTGCCTG GCTGGTCTGA CCTGGCTGTC CGTTGGTCTG      180

TTCATCATCG CTCACGACGC TATGCACGGT TCCGTTGTTC CGGGTCGTCC GCGGGCTAAC      240

GCTGCTATCG GTCAGCTGGC TCTGTGGCTG TACGCTGGTT CTCCTGGCC GAAACTGATC       300

GCTAAACACA TGACCCACCA CCGTCACGCT GGTACCGACA ACGACCCGGA CTTCGGTCAC      360

GGTGGTCCGG TTCGTTGGTA CGGTTCCTTC GTTTCCACCT ACTTCGGTTG GCGTGAAGGT      420

CTGCTGCTGC CGGTTATCGT TACCACCTAC GCTCTGATCC TGGGTGACCG TTGGATGTAC      480

GTTATCTTCT GGCCGGTTCC GGCTGTTCTG GCTTCCATCC AGATCTTCGT TTTCGGTACC      540

TGGCTGCCGC ACCGTCCGGG TCACGACGAC TTCCCGGACC GTCACAACGC TCGTTCCACC      600

GGTATCGGTG ACCCGCTGTC CCTGCTGACC TGCTTCCACT TCGGTGGTTA CCACCACGAA      660

CACCACCTGC ACCCGCACGT TCCGTGGTGG CGTCTGCCGC GTACCCGTAA AACCGGTGGT      720

CGTGCT                                                                726
```

(2) INFORMATION FOR SEQ ID NO:12:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:12:

```
CCTGGATGAC GTGCTGGAAT ATTCC                                            25
```

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:13:

CAAGGCCCAG ATCGCAGGCG                                                   20

(2) INFORMATION FOR SEQ ID NO:14:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:14:

ACGAAGGCAC CGATGACGCC CA                                                22

(2) INFORMATION FOR SEQ ID NO:15:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:15:

CGGACCTGGC CGTCGCATGA CCGATC                                            26

(2) INFORMATION FOR SEQ ID NO:16:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:16:

CGGATCGCAA TACATGAGCC ATG                                               23

(2) INFORMATION FOR SEQ ID NO:17:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:17:

CTGCAGGAGA GAGCATGAGT TCCG                                  24

(2) INFORMATION FOR SEQ ID NO:18:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:18:

GCAAGGGGCC GGCATGAGCA CTT                                   23

(2) INFORMATION FOR SEQ ID NO:19:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: mRNA (iii) HYPOTHETICAL: NO (iv) ANTI-SENSE: NO (xi) SEQUENCE DESCRIPTION: SEQ ID NO:19:

AAAGGAGGGU UUCAUAUGAG C                                     21

(2) INFORMATION FOR SEQ ID NO:20:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: mRNA (iii) HYPOTHETICAL: NO (iv) ANTI-SENSE: NO (xi) SEQUENCE DESCRIPTION: SEQ ID NO:20:

AAAGGAGGAC ACGUGAUGAG C                                     21

(2) INFORMATION FOR SEQ ID NO:21:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: mRNA (iii) HYPOTHETICAL: NO (iv) ANTI-SENSE: NO (xi) SEQUENCE DESCRIPTION: SEQ ID NO:21:

```
AAAGGAGGCA AUUGAGAUGA GU                                                   22

(2) INFORMATION FOR SEQ ID NO:22:

(i) SEQUENCE CHARACTERISTICS:
          (A) LENGTH: 22 base pairs
          (B) TYPE: nucleic acid
          (C) STRANDEDNESS: single
          (D) TOPOLOGY: linear (ii) MOLECULE TYPE: mRNA (iii) HYPOTHETICAL: NO (iv) ANTI-SENSE: NO (xi) SEQUENCE DESCRIPTION: SEQ ID NO:22:

AAAGGAGGAU CCAAUCAUGA CC                                                   22

(2) INFORMATION FOR SEQ ID NO:23:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: mRNA (iii) HYPOTHETICAL: NO (iv) ANTI-SENSE: NO (xi) SEQUENCE DESCRIPTION: SEQ ID NO:23:

AAAGGAGGGU UUCUUAUGAC G                                                    21

(2) INFORMATION FOR SEQ ID NO:24:

(i) SEQUENCE CHARACTERISTICS:
          (A) LENGTH: 15 base pairs
          (B) TYPE: nucleic acid
          (C) STRANDEDNESS: single
          (D) TOPOLOGY: linear (ii) MOLECULE TYPE: mRNA (iii) HYPOTHETICAL: NO (iv) ANTI-SENSE: NO (xi) SEQUENCE DESCRIPTION: SEQ ID NO:24:

GAUCACCUCC UUUCU                                                           15

(2) INFORMATION FOR SEQ ID NO:25:

(i) SEQUENCE CHARACTERISTICS:
          (A) LENGTH: 13 base pairs
          (B) TYPE: nucleic acid
          (C) STRANDEDNESS: single
          (D) TOPOLOGY: linear (ii) MOLECULE TYPE: mRNA (iii) HYPOTHETICAL: NO (iv) ANTI-SENSE: NO (xi) SEQUENCE DESCRIPTION: SEQ ID NO:25:

GAUCACCUCC UUA                                                             13
```

(2) INFORMATION FOR SEQ ID NO:26:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:26:

TATATCTAGA CATATGTCCG GTCGTAAACC GG        32

(2) INFORMATION FOR SEQ ID NO:27:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:27:

TATAGAATTC CACGTGTCAA GCACGACCAC CGGTTTTACG        40

(2) INFORMATION FOR SEQ ID NO:28:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:28:

TATATACTAG TAAGAGGACA AATTACATAT GACGCCCAAG CAGCAGCAAT TC        52

(2) INFORMATION FOR SEQ ID NO:29:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:29:

TATATACCCG GGTCAGCCGC GACGGCCTGT GG        32

(2) INFORMATION FOR SEQ ID NO:30:

(i) SEQUENCE CHARACTERISTICS:

(A) LENGTH: 50 base pairs
            (B) TYPE: nucleic acid
            (C) STRANDEDNESS: single
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:30:

TATATGAATT CAAGAGGAGA AATTACATAT GAGCACTTGG GCCGCAATCC                50

(2) INFORMATION FOR SEQ ID NO:31:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:31:

GTTTCAGCTC TGCCTTGAGG C                                              21

(2) INFORMATION FOR SEQ ID NO:32:

(i) SEQUENCE CHARACTERISTICS:
            (A) LENGTH: 62 base pairs
            (B) TYPE: nucleic acid
            (C) STRANDEDNESS: single
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:32:

GCGAAGGGGC GGATCGCAAT ACGTGAAAGG AGGACACGTG ATGAGCCATG ATCTGCTGAT    60

CG                                                                    62

(2) INFORMATION FOR SEQ ID NO:33:

(i) SEQUENCE CHARACTERISTICS:
            (A) LENGTH: 63 base pairs
            (B) TYPE: nucleic acid
            (C) STRANDEDNESS: single
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:33:

GCCCCCTGCT GCAGGAGAGA GCTTGAAAGG AGGCAATTGA GATGAGTTCC GCCATCGTCA    60

TCG                                                                   63

(2) INFORMATION FOR SEQ ID NO:34:

```
    (i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:34:

GGTCATGCTG TCGGACCTGG CCGTCGCTTG AAAGGAGGAT CCAATCATGA CCGATCTGAC    60

GGCGACTTCC                                                          70

(2) INFORMATION FOR SEQ ID NO:35:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:35:

ATATATCTCA ATTGCCTCCT TTCAAGCTCT CTCCTGCAGC AGGG                     44

(2) INFORMATION FOR SEQ ID NO:36:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:36:

ATGATTGGAT CCTCCTTTCA AGCGACGGCC AGGTCCGACA GC                       42

(2) INFORMATION FOR SEQ ID NO:37:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:37:

CAGAACCCAT CACCTGCCCG TC                                             22

(2) INFORMATION FOR SEQ ID NO:38:

(i) SEQUENCE CHARACTERISTICS:
```

```
        (A) LENGTH: 27 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:38:

CGCGAATTCT CGCCGGCAAT AGTTACC                                              27

(2) INFORMATION FOR SEQ ID NO:39:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:39:

GTCACATGCA TGCATGTTAC GAGCTCATAA GCATGTGACG TCTTCAACTA ACGGGGCAGG         60

(2) INFORMATION FOR SEQ ID NO:40:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:40:

AGCTTGGATC CTTAAGTACT CTAGAGTTTA AACG                                     34

(2) INFORMATION FOR SEQ ID NO:41:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:41:

AATTCGTTTA AACTCTAGAG TACTTAAGGA TCCA                                     34

(2) INFORMATION FOR SEQ ID NO:42:

(i) SEQUENCE CHARACTERISTICS:
        (A) LENGTH: 46 base pairs
        (B) TYPE: nucleic acid
        (C) STRANDEDNESS: single
```

(D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:42:

TCGACCCTAG GCACGTGACG CGTCAATTGG ATCCGCATGC AAGCTT                    46

(2) INFORMATION FOR SEQ ID NO:43:

(i) SEQUENCE CHARACTERISTICS:
            (A) LENGTH: 46 base pairs
            (B) TYPE: nucleic acid
            (C) STRANDEDNESS: single
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:43:

GATCAAGCTT GCATGCGGAT CCAATTGACG CGTCACGTGC CTAGGG                    46

(2) INFORMATION FOR SEQ ID NO:44:

(i) SEQUENCE CHARACTERISTICS:
            (A) LENGTH: 84 base pairs
            (B) TYPE: nucleic acid
            (C) STRANDEDNESS: single
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:44:

GTGTCCTCCT TTCACGTATT GCGATCCGCC CCTTCGCGGT CCTTCAGCAG CGCGCCCGAG     60

CGTTTCAGCT CTGCCTTGAG GCTG                                           84

(2) INFORMATION FOR SEQ ID NO:45:

(i) SEQUENCE CHARACTERISTICS:
            (A) LENGTH: 88 base pairs
            (B) TYPE: nucleic acid
            (C) STRANDEDNESS: single
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:45:

TCGACAGCCT CAAGGCAGAG CTGAAACGCT CGGGCGCGCT GCTGAAGGAC CGCGAAGGGG     60

CGGATCGCAA TACGTGAAAG GAGGACAC                                       88

(2) INFORMATION FOR SEQ ID NO:46:

(i) SEQUENCE CHARACTERISTICS:
            (A) LENGTH: 17 base pairs
            (B) TYPE: nucleic acid (C) STRANDEDNESS: single
           (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:46:

TAAGAAACCC TCCTTTA                                                    17

(2) INFORMATION FOR SEQ ID NO:47:

(i) SEQUENCE CHARACTERISTICS:
           (A) LENGTH: 19 base pairs
           (B) TYPE: nucleic acid
           (C) STRANDEDNESS: single
           (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:47:

CTAGTAAAGG AGGCTTTCT                                                  19

We claim:

1. A polynucleotide comprising a DNA sequence which encodes the geranylgeranyl pyrophosphate (GGPP) synthase of Flavobacterium sp. R1534 (crtE), said polynucleotide being substantially free of other polynucleotides of Flavobacterium sp. R1534.

2. The polynucleotide of claim 1 wherein said GGPP synthase has the amino acid sequence of FIG. 8 [SEQ ID NO: 1].

3. The polynucleotide of claim 2 wherein said DNA sequence comprises residues 2521–3408 of FIG. 7 [SEQ ID NO: 2].

4. A polynucleotide comprising a DNA sequence which encodes the prephytoene synthase of Flavobacterium sp. R1534 (crtB), said polynucleotide being substantially free of other polynucleotides of Flavobacterium sp. R1534.

5. The polynucleotide of claim 4 wherein said prephytoene synthase has the amino acid sequence of FIG. 9 [SEQ ID NO: 3].

6. The polynucleotide of claim 5 wherein said DNA sequence comprises residues 4316–3405 of FIG. 7 [SEQ ID NO: 4].

7. A polynucleotide comprising a DNA sequence which encodes the phytoene desaturase of Flavobacterium sp. R1534 (crtI), said polynucleotide being substantially free of other polynucleotides of Flavobacterium sp. R1534.

8. The polynucleotide of claim 4 wherein said phytoene desaturase has the amino acid sequence of FIG. 10 [SEQ ID NO: 5].

9. The polynucleotide of claim 8 wherein said DNA sequence comprises residues 4313–5797 of FIG. 7 [SEQ ID NO: 6].

10. A polynucleotide comprising a DNA sequence which encodes the lycopene cyclase of Flavobacterium sp. R1534 (crtY), said polynucleotide being substantially free of other polynucleotides of Flavobacterium sp. R1534.

11. The polynucleotide of claim 10 wherein said lycopene cyclase has the amino acid sequence of FIG. 11 [SEQ ID NO: 7].

12. The polynucleotide of claim 11 wherein said DNA sequence comprises residues 5794–6942 of FIG. 7 [SEQ ID NO: 8].

13. A polynucleotide comprising a DNA sequence which encodes the β-carotene hydroxylase of Flavobacterium sp. R1534 (crtZ), said polynucleotide being substantially free of other polynucleotides of Flavobacterium sp. R1534.

14. The polynucleotide of claim 13 wherein said β-carotene hydroxylase has the amino acid sequence of FIG. 12 [SEQ ID NO: 9].

15. The polynucleotide of claim 14 wherein said DNA sequence comprises residues 6939–7448 of FIG. 7 [SEQ ID NO: 10].

16. A polynucleotide which comprises the following DNA sequences:

a) a DNA sequence which encodes the GGPP synthase of Flavobacterium sp. R1534 (crtE),
   b) a DNA sequence which encodes the prephytoene synthase of Flavobacterium sp. R1534 (crtB), and
   c) a DNA sequence which encodes the phytoene desaturase of Flavobacterium sp. R1534 (crtI);
   said polynucleotide being substantially free of other polynucleotides of Flavobacterium sp. R1534.

17. The polynucleotide of claim 16 wherein:
   a) the GGPP synthase has the amino acid sequence of FIG. 8 [SEQ ID NO: 1],
   b) the prephytoene synthase has the amino acid sequence of FIG. 9 [SEQ ID NO: 3], and
   c) the phytoene desaturase has the amino acid sequence of FIG. 10 [SEQ ID NO: 5].

18. The polynucleotide of claim 17 wherein:
   a) the DNA sequence encoding the GGPP synthase comprises residues 2521–3408 of FIG. 7 [SEQ ID NO: 2],
   b) the DNA sequence encoding the prephytoene synthase comprises residues 4316–3405 of FIG. 7 [SEQ ID NO: 4], and c) the DNA sequence encoding the phytoene desaturase comprises residues 4313–5797 of FIG. 7 [SEQ ID NO: 6].

19. A polynucleotide which comprises the following DNA sequences:
   a) a DNA sequence which encodes the GGPP synthase of Flavobacterium sp. R1534 (crtE),
   b) a DNA sequence which encodes the prephytoene synthase of Flavobacterium sp. R1534 (crtB),
   c) a DNA sequence which encodes the phytoene desaturase of Flavobacterium sp. R1534 (crtI), and
   d) a DNA sequence which encodes the lycopene cyclase of Flavobacterium sp. R1534 (crtY);
   said polynucleotide being substantially free of other polynucleotides of Flavobacterium sp. R1534.

20. The polynucleotide of claim 19 wherein:
   a) the GGPP synthase has the amino acid sequence of FIG. 8 [SEQ ID NO: 1],
   b) the prephytoene synthase has the amino acid sequence of FIG. 9 [SEQ ID NO: 3],
   c) the phytoene desaturase has the amino acid sequence of FIG. 10 [SEQ ID NO: 5], and
   d) the lycopene cyclase has the amino acid sequence of FIG. 11 [SEQ ID NO: 7].

21. The polynucleotide of claim 20 wherein:
   a) the DNA sequence encoding the GGPP synthase comprises residues 2521–3408 of FIG. 7 [SEQ ID NO: 2],
   b) the DNA sequence encoding the prephytoene synthase comprises residues 4316–3405 of FIG. 7 [SEQ ID NO: 4],
   c) the DNA sequence encoding the phytoene desaturase comprises residues 4313–5797 of FIG. 7 [SEQ ID NO: 6], and
   d) the DNA sequence encoding the lycopene cyclase comprises residues 5794–6942 of FIG. 7 [SEQ ID NO: 8].

22. A polynucleotide which comprises the following DNA sequences:
   a) a DNA sequence which encodes the GGPP synthase of Flavobacterium sp. R1534 (crtE),
   b) a DNA sequence which encodes the prephytoene synthase of Flavobacterium sp. R1534 (crtB),
   c) a DNA sequence which encodes the phytoene desaturase of Flavobacterium sp. R1534 (crtI),
   d) a DNA sequence which encodes the lycopene cyclase of Flavobacterium sp. R1534 (crtY), and
   e) a DNA sequence which encodes the β-carotene hydroxylase of Flavobacterium sp. R1534 (crtZ);
   said polynucleotide being substantially free of other polynucleotides of Flavobacterium sp. R1534.

23. The polynucleotide of claim 22 wherein:
   a) the GGPP synthase has the amino acid sequence of FIG. 8 [SEQ ID NO: 1],
   b) the prephytoene synthase has the amino acid sequence of FIG. 9 [SEQ ID NO: 9],
   c) the phytoene desaturase has the amino acid sequence of FIG. 10 [SEQ ID NO: 10],
   d) the lycopene cyclase has the amino acid sequence of FIG. 11 [SEQ ID NO: 7], and
   e) the β-carotene hydroxylase has the amino acid sequence of FIG. 12 [SEQ ID NO: 9].

24. The polynucleotide of claim 23 wherein:
   a) the DNA sequence encoding the GGPP synthase comprises residues 2521–3408 of FIG. 7 [SEQ ID NO: 2],
   b) the DNA sequence encoding the prephytoene synthase comprises residues 4316–3405 of FIG. 7 [SEQ ID NO: 4],
   c) the DNA sequence encoding the phytoene desaturase comprises residues 4313–5797 of FIG. 7 [SEQ ID NO: 6],
   d) the DNA sequence encoding the lycopene cyclase comprises residues 5794–6942 of FIG. 7 [SEQ ID NO: 8], and
   e) the DNA sequence encoding the β-carotene hydroxylase comprises residues 6939–7448 of FIG. 7 [SEQ ID NO: 10].

25. The polynucleotide of claim 19 which further comprises a DNA sequence which encodes the β-carotene β4-oxygenase of Alcaligenes strain PC-1 (crt W).

26. The polynucleotide of claim 20 which further comprises a DNA sequence which encodes the β-carotene β4-oxygenase of Alcaligenes strain PC-1 (crt W).

27. The polynucleotide of claim 21 which further comprises a DNA sequence which encodes the β-carotene β4-oxygenase of Alcaligenes strain PC-1 (crt W).

28. The polynucleotide of claim 22 which further comprises a DNA sequence which encodes the β-carotene β4-oxygenase of Alcaligenes strain PC-1 (crt W).

29. The polynucleotide of claim 23 which further comprises a DNA sequence which encodes the β-carotene β4-oxygenase of Alcaligenes strain PC-1 (crt W).

30. The polynucleotide of claim 24 which further comprises a DNA sequence which encodes the β-carotene β4-oxygenase of Alcaligenes strain PC-1 (crt W).

31. An expression vector comprising a polynucleotide and a regulatory sequence, wherein said polynucleotide comprises a DNA sequence which encodes the GGPP synthase of Flavobacterium sp. R1534 (crtE).

32. The expression vector of claim 31 wherein the DNA sequence encodes a GGPP synthase which has the amino acid sequence of FIG. 8 [SEQ ID NO: 1].

33. The expression vector of claim 32 wherein the DNA sequence comprises residues 2521–3408 of FIG. 7 [SEQ ID NO: 2].

34. An expression vector comprising a polynucleotide and a regulatory sequence, wherein said polynucleotide comprises a DNA sequence which encodes the prephytoene synthase of Flavobacterium sp. R1534 (crtB).

35. The expression vector of claim 34 wherein DNA sequence encodes a prephytoene synthase having the amino acid sequence of FIG. 9 [SEQ ID NO: 3].

36. The expression vector of claim 35 wherein the DNA sequence comprises residues 4316–3405 of FIG. 7 [SEQ ID NO: 4].

37. An expression vector comprising a polynucleotide and a regulatory sequence, wherein said polynucleotide comprises a DNA sequence which encodes the phytoene desaturase of Flavobacterium sp. R1534 (crtI).

38. The expression vector of claim 37 wherein the DNA sequence encodes a phytoene desaturase having the amino acid sequence of FIG. 10 [SEQ ID NO: 5].

39. The expression vector of claim 38 wherein the the DNA sequence comprises residues 4313–5797 of FIG. 7 [SEQ ID NO: 6].

40. An expression vector comprising a polynucleotide and a regulatory sequence, wherein said polynucleotide comprises a DNA sequence which encodes the lycopene cyclase of Flavobacterium sp. R1534 (crtY).

41. The expression vector of claim 40 wherein the DNA sequence encodes a lycopene cyclase having the amino acid sequence of FIG. 11 [SEQ ID NO: 7].

42. The expression vector of claim 41 wherein the DNA sequence comprises residues 5794–6942 of FIG. 7 [SEQ ID NO: 8].

43. An expression vector comprising a polynucleotide and a regulatory sequence, wherein said polynucleotide comprises a DNA sequence which encodes the β-carotene hydroxylase of Flavobacterium sp. R1534 (crtZ).

44. The expression vector of claim 43 wherein the DNA sequence encodes a β-carotene hydroxylase having the amino acid sequence of FIG. 12 [SEQ ID NO: 9].

45. The expression vector of claim 44 wherein the DNA sequence comprises residues 6939–7448 of FIG. 7 [SEQ ID NO: 10].

46. An expression vector comprising a polynucleotide and a regulatory sequence, wherein said polynucleotide comprises the following DNA sequences:
   a) a DNA sequence which encodes the GGPP synthase of Flavobacterium sp. R1534 (crtE),
   b) a DNA sequence which encodes the prephytoene synthase of Flavobacterium sp. R1534 (crtB), and
   c) a DNA sequence which encodes the phytoene desaturase of Flavobacterium sp. R1534 (crtI).

47. The expression vector of claim 46 wherein:
   a) the GGPP synthase has the amino acid sequence of FIG. 8 [SEQ ID NO: 1],
   b) the prephytoene synthase has the amino acid sequence of FIG. 9 [SEQ ID NO: 3], and
   c) the phytoene desaturase has the amino acid sequence of FIG. 10 [SEQ ID NO: 5].

48. The expression vector of claim 47 wherein:
   a) the DNA sequence encoding the GGPP synthase comprises bases 2521–3408 of FIG. 7 [SEQ ID NO: 2],
   b) the DNA sequence encoding the prephytoene synthase comprises bases 4316–3405 of FIG. 7 [SEQ ID NO: 4], and
   c) the DNA sequence encoding the phytoene desaturase comprises bases 4313–5797 of FIG. 7 [SEQ ID NO: 6].

49. An expression vector comprising a polynucleotide and a regulatory sequence, wherein said polynucleotide comprises the following DNA sequences:
   a) a DNA sequence which encodes the GGPP synthase of Flavobacterium sp. R1534 (crtE),
   b) a DNA sequence which encodes the prephytoene synthase of Flavobacterium sp. R1534 (crtB),
   c) a DNA sequence which encodes the phytoene desaturase of Flavobacterium sp. R1534 (crtI), and
   d) a DNA sequence which encodes the lycopene cyclase of Flavobacterium sp. R1534 (crtY).

50. The expression vector of claim 49 wherein:
   a) the GGPP synthase has the amino acid sequence of FIG. 8 [SEQ ID NO: 1],
   b) the prephytoene synthase has the amino acid sequence of FIG. 9 [SEQ ID NO: 3],
   c) the phytoene desaturase has the amino acid sequence of FIG. 10 [SEQ ID NO: 5], and
   d) the lycopene cyclase has the amino acid sequence of FIG. 11 [SEQ ID NO: 7].

51. The expression vector of claim 50 wherein:
   a) the DNA sequence encoding the GGPP synthase comprises bases 2521–3408 of FIG. 7 [SEQ ID NO: 2],
   b) the DNA sequence encoding the prephytoene synthase comprises bases 4316–3405 of FIG. 7 [SEQ ID NO: 4],
   c) the DNA sequence encoding the phytoene desaturase comprises bases 4313–5797 of FIG. 7 [SEQ ID NO: 6], and
   d) the DNA sequence encoding the lycopene cyclase comprises bases 5794–6942 of FIG. 7 [SEQ ID NO: 8].

52. An expression vector comprising a polynucleotide and a regulatory sequence, wherein said polynucleotide comprises the following DNA sequences:
   a) a DNA sequence which encodes the GGPP synthase of Flavobacterium sp. R1534 (crtE),
   b) a DNA sequence which encodes the prephytoene synthase of Flavobacterium sp. R1534 (crtB),
   c) a DNA sequence which encodes the phytoene desaturase of Flavobacterium sp. R1534 (crtI),
   d) a DNA sequence which encodes the lycopene cyclase of Flavobacterium sp. R1534 (crtY), and
   e) a DNA sequence which encodes the β-carotene hydroxylase of Flavobacterium sp. R1534 (crtZ).

53. The expression vector of claim 52 wherein:
   a) the GGPP synthase has the amino acid sequence of FIG. 8 [SEQ ID NO: 1],
   b) the prephytoene synthase has the amino acid sequence of FIG. 9 [SEQ ID NO: 3],
   c) the phytoene desaturase has the amino acid sequence of FIG. 10 [SEQ ID NO: 5],
   d) the lycopene cyclase has the amino acid sequence of FIG. 11 [SEQ ID NO: 7], and
   e) the β-carotene hydroxylase has the amino acid sequence of FIG. 12 [SEQ ID NO: 9].

54. The expression vector of claim 53 wherein:
   a) the DNA sequence encoding the GGPP synthase comprises bases 2521–3408 of FIG. 7 [SEQ ID NO: 2],
   b) the DNA sequence encoding the prephytoene synthase comprises bases 4316–3405 of FIG. 7 [SEQ ID NO: 4],
   c) the DNA sequence encoding the phytoene desaturase comprises bases 4313–5797 of FIG. 7 [SEQ ID NO: 6],
   d) the DNA sequence encoding the lycopene cyclase comprises bases 5794–6942 of FIG. 7 [SEQ ID NO: 8], and
   e) the DNA sequence encoding the β-carotene hydroxylase comprises bases 6939–7448 of FIG. 7 [SEQ ID NO: 10].

55. A recombinant cell comprising a host cell transformed by an expression vector wherein said expression vector comprises a polynucleotide and a regulatory sequence, wherein said polynucleotide comprises the following DNA sequences:
   a) a DNA sequence which encodes the GGPP synthase of Flavobacterium sp. R1534 (crtE),
   b) a DNA sequence which encodes the prephytoene synthase of Flavobacterium sp. R1534 (crtB), and
   c) a DNA sequence which encodes the phytoene desaturase of Flavobacterium sp. R1534 (crtI).

56. The recombinant cell of claim 55 wherein:
   a) the GGPP synthase has the amino acid sequence of FIG. 8 [SEQ ID NO: 1],
   b) the prephytoene synthase has the amino acid sequence of FIG. 9 [SEQ ID NO: 3], and
   c) the phytoene desaturase has the amino acid sequence of FIG. 10 [SEQ ID NO: 5].

57. The recombinant cell of claim 56 wherein:
   a) the DNA sequence encoding the GGPP synthase comprises bases 2521–3408 of FIG. 7 [SEQ ID NO: 2],
   b) the DNA sequence encoding the prephytoene synthase comprises bases 4316–3405 of FIG. 7 [SEQ ID NO: 4], and c) the DNA sequence encoding the phytoene desaturase comprises bases 4313–5797 of FIG. 7 [SEQ ID NO: 6].

58. A recombinant cell comprising a host cell transformed by an expression vector wherein said expression vector comprises a polynucleotide and a regulatory sequence, wherein said polynucleotide comprises the following DNA sequences:
   a) a DNA sequence which encodes the GGPP synthase of Flavobacterium sp. R1534 (crtE),
   b) a DNA sequence which encodes the prephytoene synthase of Flavobacterium sp. R1534 (crtB),
   c) a DNA sequence which encodes the phytoene desaturase of Flavobacterium sp. R1534 (crtI), and
   d) a DNA sequence which encodes the lycopene cyclase of Flavobacterium sp. R1534 (crtY).

59. The recombinant cell of claim 58 wherein:
   a) the GGPP synthase has the amino acid sequence of FIG. 8 [SEQ ID NO: 1],
   b) the prephytoene synthase has the amino acid sequence of FIG. 9 [SEQ ID NO: 3],
   c) the phytoene desaturase has the amino acid sequence of FIG. 10 [SEQ ID NO: 5], and
   d) the lycopene cyclase has the amino acid sequence of FIG. 11 [SEQ ID NO: 7].

60. The recombinant cell of claim 59 wherein:
   a) the DNA sequence encoding the GGPP synthase comprises bases 2521–3408 of FIG. 7 [SEQ ID NO: 2],
   b) the DNA sequence encoding the prephytoene synthase comprises bases 4316–3405 of FIG. 7 [SEQ ID NO: 4],
   c) the DNA sequence encoding the phytoene desaturase comprises bases 4313–5797 of FIG. 7 [SEQ ID NO: 6], and
   d) the DNA sequence encoding the lycopene cyclase comprises bases 5794–6942 of FIG. 7 [SEQ ID NO: 8].

61. A recombinant cell comprising a host cell transformed by an expression vector, wherein said expression vector comprises a polynucleotide and a regulatory sequence, wherein said polynucleotide comprises the following DNA sequences:
   a) a DNA sequence which encodes the GGPP synthase of Flavobacterium sp. R1534 (crtE),
   b) a DNA sequence which encodes the prephytoene synthase of Flavobacterium sp. R1534 (crtB),
   c) a DNA sequence which encodes the phytoene desaturase of Flavobacterium sp. R1534 (crtI),
   d) a DNA sequence which encodes the lycopene cyclase of Flavobacterium sp. R1534 (crtY), and
   e) a DNA sequence which encodes the β-carotene hydroxylase of Flavobacterium sp. R1534 (crtZ).

62. The recombinant cell of claim 61 wherein:
   a) the GGPP synthase has the amino acid sequence of FIG. 8 [SEQ ID NO: 1],
   b) the prephytoene synthase has the amino acid sequence of FIG. 9 [SEQ ID NO: 3],
   c) the phytoene desaturase has the amino acid sequence of FIG. 10 [SEQ ID NO: 5],
   d) the lycopene cyclase has the amino acid sequence of FIG. 11 [SEQ ID NO: 7], and
   e) the β-carotene hydroxylase has the amino acid sequence of FIG. 12 [SEQ ID NO: 9].

63. The recombinant cell of claim 62 wherein:
   a) the DNA sequence encoding the GGPP synthase comprises bases 2521–3408 of FIG. 7 [SEQ ID NO: 2],
   b) the DNA sequence encoding the prephytoene synthase comprises bases 4316–3405 of FIG. 7 [SEQ ID NO: 4],
   c) the DNA sequence encoding the phytoene desaturase comprises bases 4313–5797 of FIG. 7 [SEQ ID NO: 6],
   d) the DNA sequence encoding the lycopene cyclase comprises bases 5794–6942 of FIG. 7 [SEQ ID NO: 8], and
   e) the DNA sequence encoding the β-carotene hydroxylase comprises bases 6939–7448 of FIG. 7 [SEQ ID NO: 10].

64. An isolated polynucleotide comprising a DNA sequence set forth as SEQ ID NO:2, or a DNA sequence specifically hybridizable with a complementary strand therewith under conditions of hybridization utilizing 7% sodium dodecyl sulfate (SDS), 1% bovine serum albumin (BSA), 0.5 M $Na_2HPO_4$ pH 7.2 at 65° C., said DNA sequences encode polypeptides having GGPP synthase activity.

65. The polynucleotide of claim 64 which is the DNA sequence having the sequence of SEQ ID NO:2.

66. An isolated polynucleotide comprising a DNA sequence set forth as SEQ ID NO:4, or a DNA sequence specifically hybridizable with a complementary strand therewith under conditions of hybridization utilizing 7% sodium dodecyl sulfate (SDS), 1% bovine serum albumin (BSA), 0.5 M $Na_2HPO_4$ pH 7.2 at 65° C., said DNA sequences encode polypeptides having prephytoene synthase activity.

67. The polynucleotide of claim 66 which is the DNA sequence having the sequence of SEQ ID NO:4.

68. An isolated polynucleotide comprising a DNA sequence set forth as SEQ ID NO:6, or a DNA sequence specifically hybridizable with a complementary strand therewith under conditions of hybridization utilizing 7% sodium dodecyl sulfate (SDS), 1% bovine serum albumin (BSA), 0.5 M $Na_2HPO_4$ pH 7.2 at 65° C., said DNA sequences encode polypeptides having phytoene desaturase activity.

69. The polynucleotide of claim 68 which is the DNA sequence having the sequence of SEQ ID NO:6.

70. An isolated polynucleotide comprising a DNA sequence set forth as SEQ ID NO:8, or a DNA sequence specifically hybridizable with a complementary strand therewith under conditions of hybridization utilizing 7% sodium dodecyl sulfate (SDS), 1% bovine serum albumin (BSA), 0.5 M $Na_2HPO_4$ pH 7.2 at 65° C., said DNA sequences encode polypeptides having lycopene cyclase activity.

71. The polynucleotide of claim 70 which is the DNA sequence having the sequence of SEQ ID NO:8.

72. An isolated polynucleotide comprising a DNA sequence set forth as SEQ ID NO:10, or a DNA sequence specifically hybridizable with a complementary strand therewith under conditions of hybridization utilizing 7% sodium dodecyl sulfate (SDS), 1% bovine serum albumin (BSA), 0.5 M $Na_2HPO_4$ pH 7.2 at 65° C., said DNA sequences encode polypeptides having carotene hydroxylase activity.

73. The polynucleotide of claim 72 which is the DNA sequence having the sequence of SEQ ID NO:10.

* * * * *

UNITED STATES PATENT AND TRADEMARK OFFICE
CERTIFICATE OF CORRECTION

PATENT NO. : 6,087,152
DATED : July 11, 2000
INVENTOR(S) : Hans-Peter Hohmann et al.

It is certified that error appears in the above-identified patent and that said Letters Patent is hereby corrected as shown below:

Title page,
Item [56], FOREIGN PATENT DOCUMENTS, please add -- 595444A Switzerland --.

Signed and Sealed this

Eighth Day of October, 2002

Attest:

Attesting Officer

JAMES E. ROGAN
Director of the United States Patent and Trademark Office